(12) United States Patent
Dunne et al.

(10) Patent No.: US 10,220,165 B2
(45) Date of Patent: Mar. 5, 2019

(54) INHALATOR AND CAPSULE FOR AN INHALATOR

(75) Inventors: Stephen Terence Dunne, Stowmarket (GB); Jens Besseler, Bingen (DE); Jessica Frentzel-Beyme, Gau-Algesheim (DE); Holger Holakovsky, Witten (DE); Heinrich Kladders, Muelheim-Ruhr (DE); Claudius Weiler, Ingelheim (DE); Ole Zumblick, Dortmund (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 999 days.

(21) Appl. No.: 14/119,279

(22) PCT Filed: May 21, 2012

(86) PCT No.: PCT/EP2012/059324
§ 371 (c)(1),
(2), (4) Date: Feb. 27, 2014

(87) PCT Pub. No.: WO2012/163704
PCT Pub. Date: Dec. 6, 2012

(65) Prior Publication Data
US 2014/0182587 A1    Jul. 3, 2014

(30) Foreign Application Priority Data

May 27, 2011  (GB) .................................. 1109087.5
Jan. 13, 2012  (EP) .................................. 12151105

(51) Int. Cl.
*A61M 15/00*    (2006.01)
*B65D 47/28*    (2006.01)
(Continued)

(52) U.S. Cl.
CPC .... *A61M 15/0035* (2014.02); *A61M 15/0025* (2014.02); *A61M 15/0028* (2013.01);
(Continued)

(58) Field of Classification Search
CPC .......... A61M 15/0025; A61M 15/0028; A61M 15/0035; A61M 15/0061; A61M 15/0086;
(Continued)

(56) References Cited

U.S. PATENT DOCUMENTS

| 4,076,848 A | 2/1978 | de Limur |
| 4,889,114 A | 12/1989 | Kladders |

(Continued)

FOREIGN PATENT DOCUMENTS

| EP | 0666085 A1 | 8/1995 |
| FR | 2032436 A2 | 11/1970 |

(Continued)

OTHER PUBLICATIONS

International Search Report, PCT/EP2012/059324, dated Feb. 1, 2013.

*Primary Examiner* — Gregory A Anderson
*Assistant Examiner* — Margaret M Luarca
(74) *Attorney, Agent, or Firm* — Matthew B. Dernier, Esq.

(57) ABSTRACT

The invention relates to a capsule for receiving a preferably powdered pharmaceutical preparation and an inhaler in which, for inhalation, the preparation is expelled from the capsule through at least one hole. A capsule according to the invention comprises as capsule elements a capsule cap and a capsule body, at least one of which comprises at least one prefabricated hole.

Systems according to the invention comprising inhalers and capsules are described, in which the prefabricated hole in the capsule is sealed off in the transporting state of the system (Continued)

and is open in the usage state. The hole is exposed by actuation of a pushing or pulling mechanism. Prior to this the hole is closed off by part of the capsule itself or by a capsule receptacle belonging to the inhaler.

In one embodiment the capsule may be present in two different states, for example in different insertion positions of the capsule elements. In the first state the prefabricated hole is closed off and in the second it is exposed.

Another system according to the invention consists of a capsule body open at the top and an inhaler, the capsule that is open at the top being filled inside the inhaler.

28 Claims, 10 Drawing Sheets

(51) Int. Cl.
*A61J 3/07* (2006.01)
*A61K 9/00* (2006.01)

(52) U.S. Cl.
CPC .... *A61M 15/0043* (2014.02); *A61M 15/0086* (2013.01); *B65D 47/283* (2013.01); *A61J 3/071* (2013.01); *A61K 9/0075* (2013.01); *A61M 15/0071* (2014.02); *A61M 15/0081* (2014.02); *A61M 2202/064* (2013.01)

(58) Field of Classification Search
CPC ........ A61M 2202/064; A61M 15/0043; A61M 15/0081; A61M 15/003; A61J 3/071; A61J 1/03; A61K 9/0075; B65D 47/283; B65D 83/06
USPC .............. 206/528, 530; 220/4.27, 4.28, 4.06
See application file for complete search history.

(56) References Cited

U.S. PATENT DOCUMENTS

| | | | | |
|---|---|---|---|---|
| 5,152,284 A | * | 10/1992 | Valentini | A61M 15/0028 128/203.12 |
| 5,170,801 A | * | 12/1992 | Casper | A61B 5/073 600/582 |
| 5,498,255 A | * | 3/1996 | Wong | A61K 9/0004 424/453 |
| 6,418,926 B1 | * | 7/2002 | Chawla | A61M 15/0028 128/203.15 |
| 7,025,057 B2 | * | 4/2006 | Chawla | A61M 15/0028 128/203.15 |
| 7,249,600 B2 | * | 7/2007 | Chawla | A61M 15/0028 128/203.15 |
| 7,305,986 B1 | * | 12/2007 | Steiner | A61M 15/0028 128/203.12 |
| 7,878,193 B2 | | 2/2011 | Kladders et al. | |
| 9,010,325 B2 | * | 4/2015 | Djupesland | A61M 15/0028 128/203.15 |
| 2004/0131668 A1 | | 7/2004 | Hochrainer et al. | |
| 2004/0173211 A1 | | 9/2004 | Kladders et al. | |
| 2007/0151562 A1 | * | 7/2007 | Jones | A61M 15/0028 128/203.21 |
| 2007/0163581 A1 | | 7/2007 | Braithwaite | |
| 2008/0177246 A1 | * | 7/2008 | Sullivan | A61M 15/0028 604/520 |
| 2009/0194105 A1 | | 8/2009 | Besseler et al. | |
| 2009/0241949 A1 | * | 10/2009 | Smutney | A61M 15/0028 128/203.15 |
| 2009/0308392 A1 | * | 12/2009 | Smutney | A61M 15/0028 128/203.15 |
| 2010/0300439 A1 | * | 12/2010 | Djupesland | A61M 15/0028 128/203.15 |

FOREIGN PATENT DOCUMENTS

| | | |
|---|---|---|
| GB | 1396258 A | 6/1975 |
| WO | 200172605 A1 | 10/2001 |

* cited by examiner

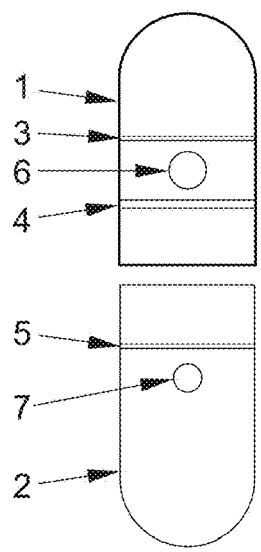
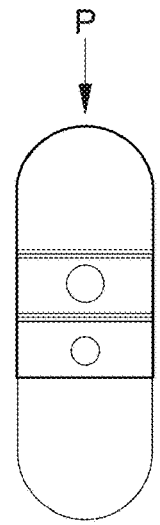
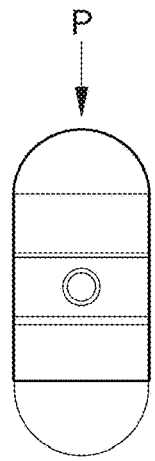
FIG. 1a    FIG. 1b    FIG. 1c
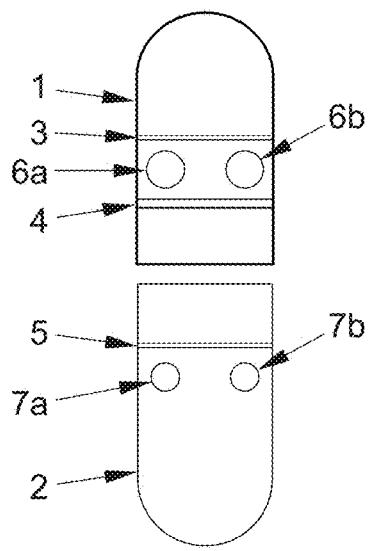
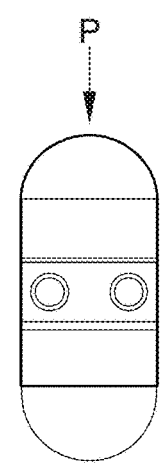
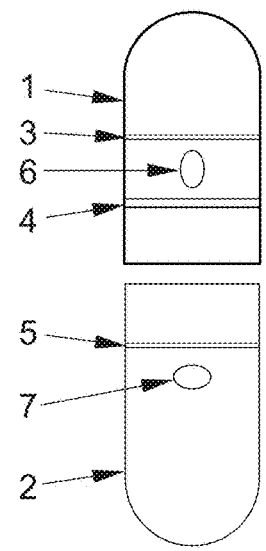
FIG. 2a    FIG. 2b    FIG. 3
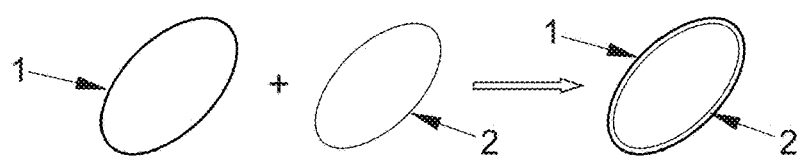
FIG. 4
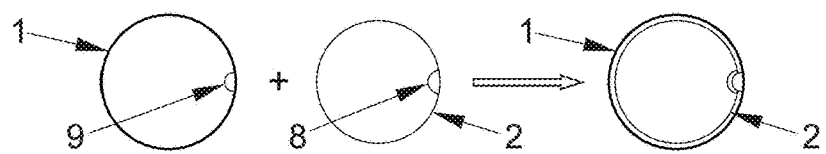
FIG. 5

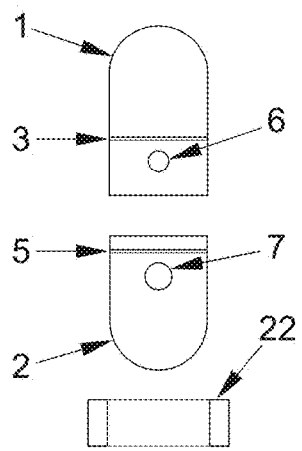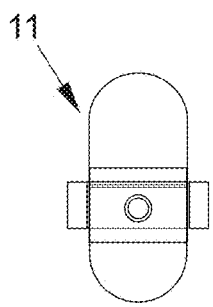
FIG. 11a    FIG. 11b    FIG. 11c
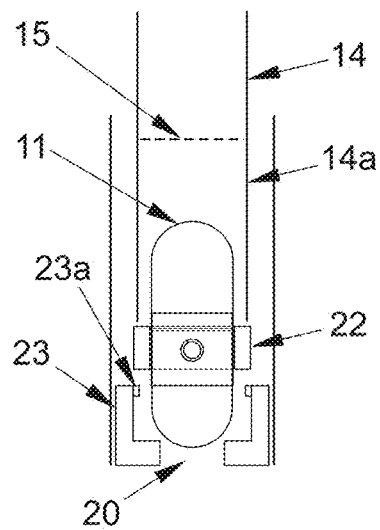
FIG. 12a    FIG. 12b    FIG. 12c
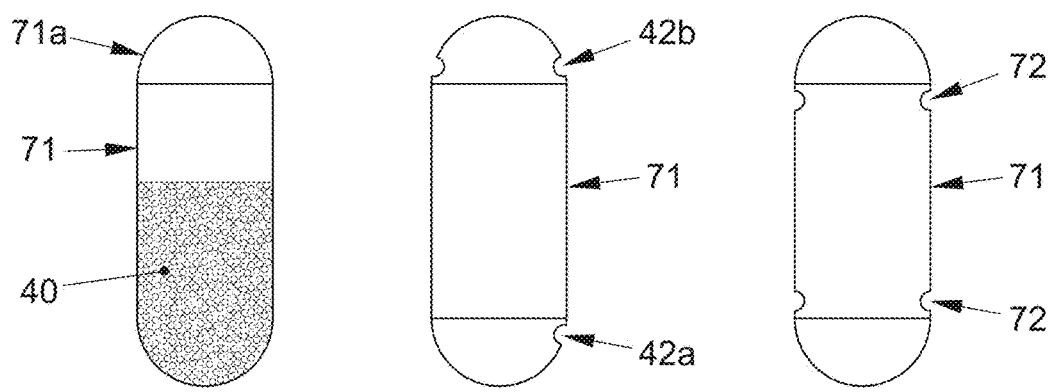
FIG. 13a    FIG. 13b    FIG. 13c

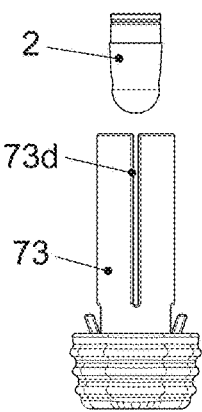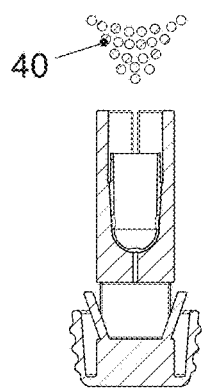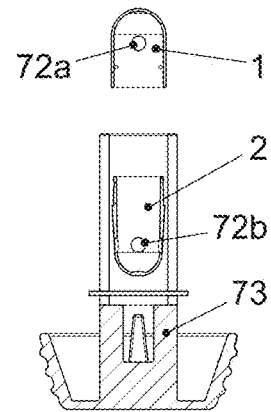
FIG. 16a    FIG. 16b    FIG. 16c
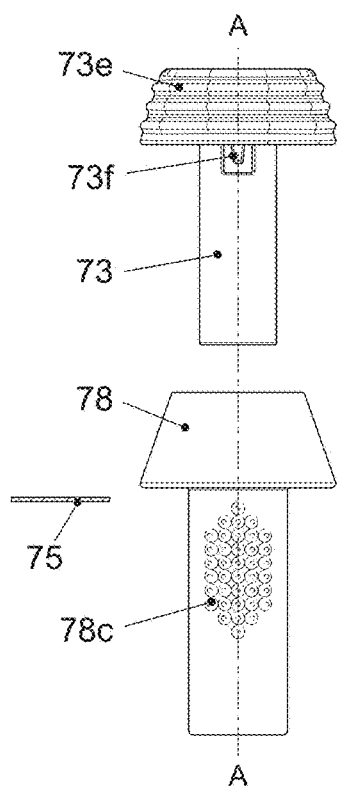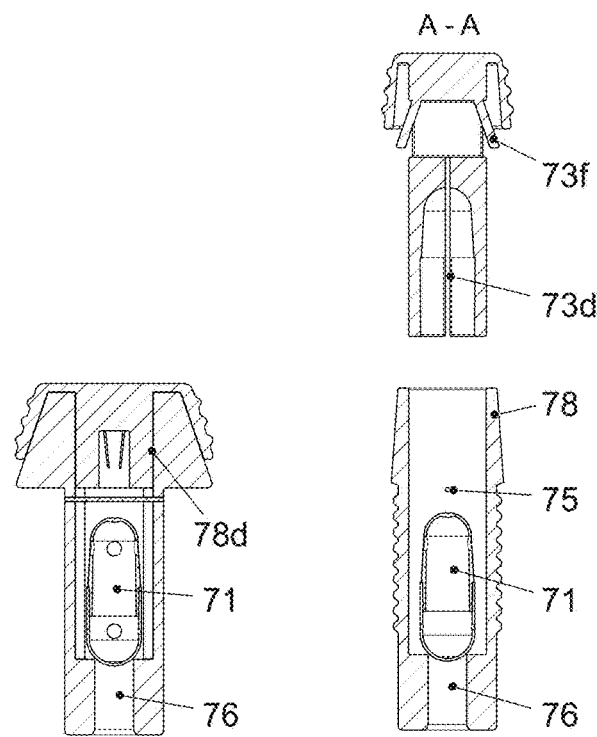
FIG. 16d    FIG. 16e    FIG. 16f

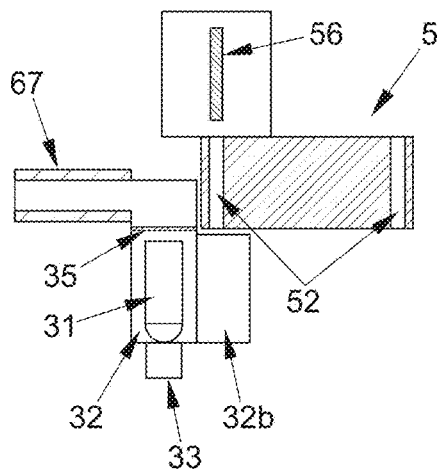
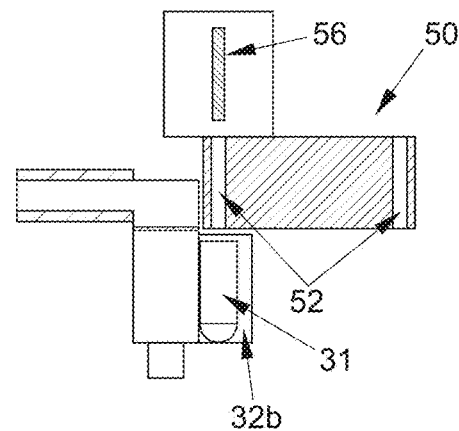
FIG. 22a  FIG. 22b
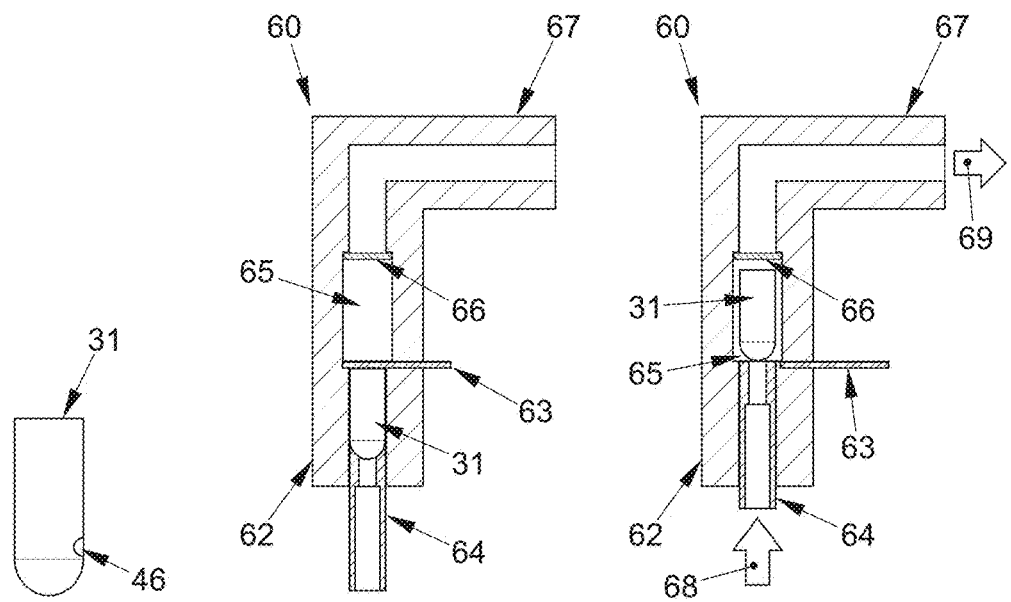
FIG. 23a  FIG. 23b  FIG. 23c

INHALATOR AND CAPSULE FOR AN INHALATOR

This application is the national phase entry under 35 U.S.C. § 371 of International Application No. PCT/EP2012/059324, filed May 21, 2012, which claims priority to EP 12151105.9, filed Jan. 13, 2012, and GB 1109087.5, filed May 27, 2011, the contents of which are hereby incorporated by reference in their entireties.

The present invention relates to a capsule for holding medicinal formulations for use in an inhaler and an associated inhaler. In particular the invention relates to capsules that are filled with a powdered pharmaceutical preparation and to inhalers with which a powdered pharmaceutical preparation is to be provided for inhalation, the powder being contained in a capsule and being expelled from the capsule for inhalation through at least one hole in the capsule wall.

Capsules are known from the prior art that are used in specific medical devices such as powder inhalers. The outer shape of capsules used in inhalers of this kind is often (as in the present specification) that of a closed cylinder with hemispherical ends, the length of the cylinder being greater than its diameter. Such capsules usually consist of two cup-shaped parts, namely a capsule body and a capsule cap which are fitted telescopically into one another. Various materials are known for such capsules. Many capsules used in medicine consist of gelatine or hard gelatine.

WO2000/07572 discloses plastic capsules for use in powder inhalers. The capsules consist of a capsule cap and capsule cap which may be jointed together so as to form a stable sealed cavity of a defined volume. The capsule may comprise latching elements that securely connect the capsule cap to the capsule body. An example of latching elements of this kind are dot-like elevations in the inner casing of the capsule cap, which engage in rather larger dot-shaped depressions on the outer casing of the capsule body. The capsule cap and capsule body both consist of the same water-insoluble, hydrophobic plastics, preferably polyethylene.

WO2006/074982 A2 discloses a closure concept for capsule cap and capsule body by means of which it is possible to join the two parts together temporarily for transporting the capsule to the filling apparatus, by means of a preliminary closure which, unlike the main closure, can be opened non-destructively. The closures are formed in the inner casing of the capsule cap by annularly extending or segment-shaped elevations and matching depressions arranged annularly around the periphery of the outer casing of the capsule body.

Various powder inhalers are known from the prior art, in which the powder is contained in capsules before inhalation. In these devices the capsules are generally opened in some way to give access to the powder for nebulisation: in some devices the capsules are cut open with cutting blades, while in others their interior is brought into communication with air passages in the inhaler by means of hollow needles. In one group of inhalers that particularly form the background to the present invention, holes are pierced in the capsules by means of needle devices.

WO2004/082750 A1 shows an example of such an inhaler in which a capsule is pierced at both ends by two opposing needles. During the inhalation process the capsule rotates about its transverse axis, being driven by air flowing in tangentially. Particles that are driven out of the interior of the capsule by its rotation then travel through the air current to the mouthpiece.

U.S. Pat. No. 5,896,855 shows an inhaler in which a plurality of capsules are stored in a rotatable magazine and are supplied by a selectively motor-controlled mechanism to a spin chamber, where the powder is also expelled from holes at the ends of the capsule by rotation of said capsule. In the magazine, the capsules are held at both ends by needles or stoppers. The capsules are either pierced at their polar ends before they are inserted in the magazine and these holes are closed up by the stoppers in the magazine until the capsule in question is delivered to the spin chamber; or the capsules are pierced by these very needles as the capsules are inserted in the magazine and the piercing needles remain in the holes to form a seal until the capsule in question is delivered to the spin chamber.

WO04/052435 A1 shows different capsule-based powder inhalers in which the nebulisation takes place using the so-called Bernoulli effect. One inhaler shown has a mouthpiece which is of similar configuration to a cap and on which a lower part is fitted which contains a capsule chamber. On the lower housing part is provided a cutting device for opening the capsules. To replace the used capsules with new ones, the mouthpiece is flipped up or a plug-in connection is released which is located between the mouthpiece and lower housing part or between the mouthpiece and a plate inserted in the lower housing part and connected to the capsule chamber. Another inhaler shown has a rotatably mounted, exchangeable or refillable revolver magazine having a plurality of chambers each loaded with a capsule.

Powder inhalers of this kind using the Bernoulli effect constitute the starting point for the invention described here and the mode of operation described hereinafter also applies to the inhalers which are the subject of the present inventions.

In the inhalers under discussion here, the active substance that is to be delivered is stored in a substantially cylindrical capsule and this capsule is inserted in the inhalation chamber of an inhaler. The capsule chamber is adapted to the size of the capsule so that it is also substantially cylindrical in configuration, its length and diameter being somewhat greater than the corresponding dimensions of the capsule. As a result the capsule inserted in the capsule chamber has enough clearance to enable it to perform vibratory movements in both the axial and radial direction, while nevertheless remaining substantially aligned along the chamber axis. The capsule chamber comprises an air inlet in the region of one of its two ends and an air outlet opening in the region of the other end. The air outlet is attached to an inhalation channel which leads to the mouthpiece of the inhaler. As a rule, the capsule chamber, air outlet, inhalation channel and opening in the mouthpiece are arranged along a common axis.

In order to deliver the contents of the capsule, the capsule is first opened normally at two points along the length of the casing. As a rule the openings are located close to the two longitudinal ends of the capsule. If an air current is then generated in the capsule chamber from the air inlet to the air outlet, this leads along the longitudinal axis of the capsule and has two effects: on the one hand, the capsule vibrates, with its preferable direction of movement running along the longitudinal axis as a result of the air current. On the other hand, the air flowing along the two capsule openings generates a negative pressure relative to the capsule interior, so that the powder contained in the capsule is sucked out by the air current and thereby nebulised.

The problem on which the present invention is based is to provide a capsule that is an improvement on the prior art, for use in inhalers, and an improved inhaler. In particular, a system comprising capsule and inhaler is to be provided, in which the reproducibility of the nebulisation, particularly the expulsion of powder from the capsule, is improved. Preferably, a system is to be provided in which irregularities in the opening of the capsules are reduced or minimised.

This problem is solved according to the invention by a capsule for use as a reservoir for a pharmaceutical preparation or medicinal formulation in an inhaler, the capsule comprising two capsule elements open at one end, namely a capsule body and a capsule cap, which can be fitted telescopically into one another through their openings to form a cavity. The capsule body and capsule cap are characterised in that at least one of the two, and preferably both, have at least one prefabricated hole in addition to the opening at one end.

Moreover, the problem according to the invention is solved by an inhaler which comprises a capsule chamber with an air inlet and an air outlet leading in the direction of a mouthpiece, a capsule being adapted to be inserted in the capsule chamber or introduced from a storage magazine or a capsule receptacle into the capsule chamber and the inhaler having a pusher, the actuation of which enables parts of the capsule to be moved relative to one another such that prefabricated holes on the capsule can be exposed.

Moreover, the problem is solved according to the invention by a system which is formed from the above-mentioned capsule and the above-mentioned inhaler.

Moreover the problem is solved according to the invention by a system which is formed from the above-mentioned capsule and an inhaler which comprises a capsule chamber, the capsule being stored, before the inhaler is used, in a capsule receptacle belonging to the inhaler. This capsule receptacle seals off at least one hole and/or all the holes that lead(s) into the cavity of the capsule after the capsule elements have been fitted together. The capsule receptacle is arranged at least partially in the capsule chamber and can be removed from the capsule chamber in such a way that the capsule is left behind in the capsule chamber when the capsule receptacle is removed.

Furthermore, the problem is solved according to the invention by a system which is formed from the above-mentioned capsule and an inhaler, the assembled capsule comprising at least one prefabricated hole and being located in the inhaler in the transporting state of the system. The capsule is at least partly surrounded by a preferably extendable and/or flexible film such that the film closes off the at least one prefabricated hole and/or all the holes in the capsule in the transporting state of the system. The film is connected to a pull strip and/or partly projects beyond the capsule at one end of the capsule. The inhaler has an opening through which the film can be pulled out of the inhaler at its projecting part and/or at its pull strip, the prefabricated holes on the capsule then being exposed.

Moreover, the problem is solved according to the invention by a system which is formed by a capsule open at the top and an inhaler, the capsule being located in a vibration chamber of the inhaler or being adapted to be pushed out of its storage in the inhaler into a vibration chamber.

Moreover, the problem is solved according to the invention by a process for preparing a system of capsule and inhaler, wherein first of all a capsule element that is open at one end is inserted in an annular component and/or a capsule receptacle, is filled with a measured amount of pharmaceutical preparation, the capsule element is closed and the annular component and/or the capsule receptacle assembled with all the other components of the inhaler.

Advantageous further features will be described hereinafter and in detail with reference to the Figures.

One feature of the present invention is that the assembled capsule may be present in two different states: in the first state the at least one prefabricated hole is closed, in the second it is exposed. In the inhaler in which this capsule is inserted, the capsule is switched from the first state into the second, in which the pharmaceutical preparation can then escape from the capsule through the prefabricated hole.

In the system of inhaler and capsule according to the invention, the at least one prefabricated hole in the capsule is sealed off in the transporting state (first state) of the system and is exposed in the state of use (second state). By actuating a push or pull mechanism the hole is exposed. Prior to this the hole is closed off by part of the capsule itself or by a capsule receptacle or the like belonging to the inhaler.

A further feature of the present invention is that the two capsule elements comprise prefabricated holes and, when fitted telescopically into one another, two insertion positions relative to one another (these two insertion positions correspond in their configuration to the so-called first and second states of the capsule): a first insertion position in which the two elements are fitted into one another such that the prefabricated holes are covered and the cavity of the capsule as a whole is closed off, and a second insertion position in which the prefabricated holes in the capsule body and capsule cap overlap with one another, such that the entire capsule has one hole at the place of overlap of the two holes.

Preferably, both capsule elements are cup-shaped: The cavity open at one end which they form is laterally bounded by a surrounding capsule casing and by a closed end relative to the open side. Preferably, the capsule casing forms a cylindrical or elliptically surrounding wall, so that no corners are formed on the inside of the assembled capsule in which, in particular, powdered pharmaceutical preparation could accumulate and thus be left behind when powder is subsequently expelled from the capsule. For the same reason, the undersides of the capsule body and capsule cap and hence both ends of the capsule produced by fitting them together have a convex, particularly substantially hemispherical or ellipsoid shape.

The prefabricated holes in the capsule cap and capsule body are preferably located in the respective casing area, so that when they are fitted together the casing of the other capsule element covers the respective hole until the insertion position in which the two holes are brought into registry is reached.

By the use of the term "prefabricated" for a hole is meant that the hole is produced in the respective capsule element during the capsule manufacturing process at the factory. The hole in the respective capsule element is already present before the individual capsule has been finally assembled. In particular, the hole or holes is or are already present in the capsule elements before the capsule as a whole is inserted in an inhaler.

Preferably, the capsule cap and capsule body are structured, on the sides of the capsule casing region that fit against one another in the assembled state. This structuring is preferably designed to perform different functions. On the one hand, the structures of the capsule cap and capsule body have alternate latching elements. Preferably, when the capsule elements are fitted into one another, this structure causes the capsule cap and the capsule body to latch together in relation to one another in at least two positions, particularly the insertion positions referred to. Latching in the first insertion position ensures that on the one hand the holes in the capsules are not accidentally exposed prematurely, e.g. as a result of vibration during transporting, and a defined process such as pushing the two elements together while applying a defined pressure is needed in order to expose the holes. Moreover, the cooperating latching elements of the capsule cap and capsule body are preferably configured so that after being fitted together up to the first insertion position the two capsule elements can no longer be non-destructively separated from one another. This prevents the capsule from opening accidentally. Preferably, in the contact region between the capsule cap and capsule body, structuring elements are also provided which serve as a guide for the two capsule elements as they are fitted into one another. These structuring elements on the casing regions of the capsule cap and capsule body that are directed towards one another ensure that the two capsule elements can only be fitted into one another in defined alignments. The "defined alignment" refers to the rotation of the capsule elements about the longitudinal axis of the capsule and is therefore an azimuthal alignment. Preferably, these structuring elements are in the form of at least one groove in the outer/inner casing surface of the capsule cap/capsule body and, respectively, in the form of at least one guide rail in the inner/outer casing surface of the capsule body/capsule cap. This ensures that when the capsule elements are fitted into one another the prefabricated holes in the capsule cap and capsule body are brought safely into registry. Preferably, the guides used are straight, particularly parallel to the main axis of the capsule. Variants in which the structuring elements guide the movement of the capsule elements along a curved path during the assembly are also possible. This would be achieved for example by a helical guide groove or guide rail.

Another feature of the present invention that may be implemented both independently and in conjunction with the above-mentioned aspects is that the capsule instead of being cylindrical in cross-section has an elliptical cross-section. Preferably the ellipse is one that deviates only slightly from the shape of a circle (the ratio of longitudinal to transverse axis of the ellipse should be less than 75%, preferably between 90% and 85%). An elliptical cross-section of this kind forces a defined azimuthal alignment of the two capsule elements as they are fitted together and/or a defined orientation when a resulting capsule is fitted into a capsule receptacle.

According to a further feature of the present invention, the hole in the outer capsule element is preferably configured as an oblong hole, or an elliptical hole or somewhat larger than the associated hole in the inner capsule element. When the outer hole is formed as an oblong hole or an ellipse, the small diameter of the hole is preferably at least as great as the diameter of the hole in the inner capsule element. The outer capsule element is the one that is formed by the outer wall of the capsule, by means of the capsule body and capsule cap in the assembled state in the region of the capsule casings abutting on one another. As a result of this enlargement of the outer hole relative to the inner one, the tolerances with respect to the accuracy of insertion of the capsule elements are broadened. This ensures that even if they are not pushed together precisely, the entire capsule opening is still available.

Another feature of the present invention is that a capsule filled with a pharmaceutical preparation which comprises a capsule cap and/or a capsule body with prefabricated holes is used in an inhaler, the prefabricated holes being covered at the moment of insertion of the capsule in a capsule chamber of the inhaler and being exposed by the actuation of a pusher in the inhaler.

This makes it possible to provide a capsule-based inhaler preferably using the Bernoulli effect for nebulisation, in which no piercing devices have to be provided to perforate the capsule. The exposing of prefabricated holes offers various advantages over the use of piercing means in the inhaler: as a result of the manufacturing process, e.g. by plastics extrusion, the prefabricated holes are highly reproducible in size and shape from one capsule to another, whereas holes produced by piercing may vary individually depending on the capsule material, capsule size and equipment as well as the piercing position and geometry of the needles, and/or may lead to irregular hole geometries. Moreover, when capsules are pierced, it is possible for a certain spring-back to occur in the capsule surface in the region of the piercing site. The prefabricated holes envisaged here, by contrast, are stable in shape after being exposed and have no protrusions in the capsule material. Such protrusions in the capsule material are formed for example when the capsule wall is pressed in by a piercing device and may possibly lead to the accumulation of, in particular, powdered pharmaceutical preparation and hence to a slightly reduced delivery of the preparation from the capsule on nebulisation. Because of the high precision in the size and shape of the capsule holes which is made possible by the prefabrication of the holes, both the amount and also, in particular, the distribution of the powder expelled from capsules in the airflow in the capsule chamber of an inhaler are more reproducible. The nebulisation of the pharmaceutical preparation itself is thus made more reproducible, particularly compared with inhalers having capsule piercing means.

Another feature of the present invention is that the inhaler for use with capsules having prefabricated hole comprises a pusher and this pusher forms a boundary of the inner space of the capsule chamber, particularly part of the wall of the capsule chamber itself, in order to expose the prefabricated capsule holes. For opening the capsule, therefore, no additional openings need to be formed on the capsule chamber which might adversely affect the flow characteristics during nebulisation. There is no formation of unwanted secondary air or false air besides the air channels required for the nebulisation. The system is stable and reproducible in terms of the flow resistance.

By comparison, when using a piercing device, the associated piercing element has to be introduced into the capsule chamber through one or more openings, which may lead to additional unwanted air flow through these openings during inhalation. Such openings in addition to an air inlet and air outlet for the capsule chamber are not needed in the inhaler according to the invention, if they are not in turn designed to improve the airflow in the capsule chamber.

The use of a pusher to expose prefabricated holes has the additional advantage, over the use of piercing elements, that even after multiple uses no signs or wear or deposits of material are to be expected. By comparison, adverse effects of this kind may occur in inhalers with piercing means that are used repeatedly for piercing, e.g. in inhalers in which after use the old capsule in the capsule chamber is regularly replaced by a new, unused one. Particularly when using powdered pharmaceutical preparations, some of which may be sticky, in addition to wear occurring on the cutting edges or points, there may also be an accumulation of material on the piercing tips. These material depositions may, in the worst case, lead to slight changes in the dose delivered from the inhaler, either as a result of such deposits remaining on the new capsule or as a result of the formation of these deposits from the contents of a newly pierced capsule. Also, these deposits on the piercing tips, like signs of wear on the tips, may affect the geometry of the holes in the capsules and lead to irregularities in the size and shape of the holes, as a result of which the reproducibility of the delivery of the pharmaceutical preparation from the capsule is impaired. In addition, as a result of the clearance required for movement of the capsule in the capsule chamber that is necessary for the nebulisation process, there may be fluctuations in the position of the capsule relative to the piercing tips when the capsule is pierced in the capsule chamber. This leads to fluctuations in the exact position of the holes in the capsule when a plurality of capsules are being pierced.

As a result of the use of a pusher mechanism for exposing prefabricated holes on capsules, all the fluctuations in the shape, size and position of the holes resulting from the use of piercing devices and the consequent fluctuations in the delivery of the pharmaceutical preparation are avoided. The nebulisation of the pharmaceutical preparation is then independent of the mechanism for opening the holes in the capsule. This also means that when brittle capsule material is used, the risk of splintering, which may occur particularly in piercing processes, is minimised. In this way the range of possible capsule materials for use in inhalers is widened.

The use of a sliding mechanism for exposing prefabricated hole has the additional advantage that the same mechanism can be used to expose all kinds of hole arrangements on capsules. For example, in cylindrical arrangements of capsule, capsule chamber and pusher, there may be a plurality of holes on the capsule at different locations relative to its circumference. The size, shape, position and number of holes in a capsule are very variable in this design, particularly when the capsule parts are produced by injection moulding processes. Here, the results of flow simulations matched to the nebulisation of specific pharmaceutical preparations or specific powders may be used to make use of optimum hole structures for capsules for this particular preparation or this particular powder.

According to another feature of the present invention, in a preferred embodiment, the holes prefabricated in the capsule are closed off by an additional component that also belongs to the capsule. In the case of substantially cylindrical capsules with prefabricated holes in the capsule casing, this additional component has an annular structure. This ring is pushed over the capsule from outside, along the longitudinal axis thereof, so as to seal off the holes tightly.

In an alternative embodiment, the at least one hole prefabricated in the capsule is closed off by a component that belongs to the inhaler. Before transfer into a capsule chamber, the at least one substantially cylindrical capsule is stored in a capsule receptacle in the inhaler. This capsule receptacle is substantially in the shape of a cylindrical tube which is of such dimensions as to fit exactly around the cylindrical part of the capsule. The at least one prefabricated hole in the capsule is located in the cylindrical casing region of the capsule and is thus closed off by the wall of the capsule receptacle while the capsule is being stored or held in the inhaler. Preferably, the powder-filled capsule stored in this way has two holes at top and bottom, i.e. one hole at the start and one at the finish of the cylindrical casing region. Preferably, the capsule consists of a capsule body and a capsule cap, both of which have at least one prefabricated hole, while after the capsule body and capsule cap have been pushed into one another the holes remain exposed, i.e. not covered by the respective other capsule element. Alternatively the holes may also be prefabricated after the filling of the capsule and after the assembly of the capsule cap and capsule body outside the inhaler. In the capsules, amounts of powder of between 0.1 milligrams and 100 milligrams of a pure active substance or an active substance mixture may be stored, for delivery later.

The pusher by means of which the holes are exposed is designed as a function of the sealing concept of the prefabricated holes in the capsule. In capsules in which the holes are closed off by a ring as they are inserted in the capsule chamber, the pusher preferably takes the form of a hollow cylinder or a plurality of punches that move laterally past the capsule, that push the ring off the capsule and thus expose the holes. Here again, the pusher (14) in particular forms a boundary of the inner space of the capsule chamber (13).

In the case of capsules that are stored in the inhaler and whose holes are covered by a component of the inhaler that surrounds the capsule at the location of the holes, the pusher is preferably shaped like a piston. Preferably, this piston has the same diameter as the capsule receptacle and forces the capsule out of its capsule receptacle directly into the capsule chamber (which has a larger diameter than the capsule receptacle).

Particularly preferably, the piston is embodied as a hollow piston and comprises the air inlet for the capsule chamber and/or forms a wall region of the capsule chamber after the capsule has been inserted into the capsule chamber. Capsules with prefabricated holes which are closed off by receptacles in the inhaler may be used both in devices for single use (in which case they contain only one capsule) and in multi-dose devices (in which case they have a storage magazine comprising a plurality of capsule receptacles). Also possible are sealing designs in which both one section of the holes is sealed off by a ring and another section of the holes is sealed off by a capsule receptacle. Preferably, in a system of this kind, a pusher pushes the capsule both out of the capsule receptacle and out of the ring.

Another feature of the present invention is that the ring is preferably embodied so that in the fully pushed in position of the pusher it forms a seal between the pusher and the capsule receptacle and/or capsule chamber. For this purpose, the ring consists in particular of an at least partially elastic material such as for example PE, TPFE or silicon. The seal thus formed preferably serves to prevent or reduce flows of secondary air into the capsule chamber (such flows of secondary air might interfere with the production of the Bernoulli effect when using the inhaler). Particularly in the case of pushers that form part of the capsule chamber wall in the pushed-in state, gaps are thus sealed that would otherwise be present between the pusher and the capsule receptacle or between the pusher and the other walls of the capsule chamber.

Alternatively to the pusher mechanism described, the system of inhaler and capsule, particularly in the case of a system for one-time use (single-use system), comprises a pulling mechanism for exposing the prefabricated capsule holes. A pulling mechanism of this kind has the same advantages as the pusher mechanism in terms of the exposing of prefabricated holes. The pulling mechanism is preferably constructed so that the capsule is located in a capsule receptacle and the capsule receptacle is located in the capsule chamber in a state of the system suitable for transporting and storage. To make the system ready for use, the capsule receptacle is pulled out of the capsule chamber, preferably also pulled completely out of the inhaler. A device is provided which prevents the capsule with the capsule receptacle from being pulled out of the capsule chamber and/or prevents the capsule from being released from the capsule receptacle when the capsule receptacle is pulled out.

Preferably, the capsule receptacle is pulled out through a mouth tube on the inhaler. The mouth tube forms the air outlet from the capsule chamber towards the mouth end of the inhaler. This device for retaining the capsule in the capsule chamber preferably contains a bar or crosspiece which at the same time forms the upper boundary of the capsule chamber. This bar or crosspiece preferably passes through the capsule receptacle, in the storage state of the system, on the side opposite an air inlet of the capsule chamber. The capsule receptacle preferably comprises slot-like recesses as a result of which the capsule receptacle is able to slide past the crosspiece as it is pulled out of the inhaler and thus be separated from it. Preferably, the component forming the capsule receptacle in the transporting state of the system comprises a region protruding from the inhaler, on which is formed a gripping surface which the user can grasp in order to pull the capsule receptacle out of the inhaler. Also particularly preferably the component forming the capsule receptacle is configured as a cap which covers the mouth end of the inhaler in the transporting state.

Another feature of the invention is that in the case of systems for single use, the components involved in the respective pushing or pulling mechanism comprise devices that ensure that the respective pushing or pulling movement cannot be reversed non-destructively. In particular, the pusher or the capsule receptacle comprises for this purpose spring arms or other latching elements that lead to a latching of the pusher after it has been pushed in fully, in particular, or in the event of the capsule receptacle being pulled out prevents the capsule receptacle from being non-destructively returned to the capsule chamber.

The systems described above for single use may alternatively also be designed as systems with two capsules. In embodiments of this kind for two capsules the inhaler also comprises two associated two capsule chambers and two capsule receptacles. Depending on the intended use of a system of this kind having two capsules, the two capsules are optionally filled with different formulations and/or different amounts of formulation. A system of this kind comprising an inhaler and two capsules may be used for example in therapies in which two different medical formulations have to be administered simultaneously to a patient. With capsules having different fillings it may be useful to tailor the size of the capsules to the respective amount of filling. In a very particular embodiment of this kind the respective capsule chambers and capsule receptacle are also adapted in size to the respective capsules. Irrespective of the fact that this is an embodiment with two identical or two different capsules, in a system of this kind with two capsules the pushing or pulling mechanism on the inhaler is configured so that with one movement the holes on both capsules are exposed simultaneously. If the system comprises capsule receptacles for example that extend in mouth tubes of the inhaler, and a cap with a gripping surface or a tab for pulling, when the cap is pulled the two capsule receptacles preferably joined together in the region of the cap are pulled out of the inhaler simultaneously.

In capsules in which the holes are exposed by a relative movement of the capsule body and capsule cap into one another, the pusher also acts on one end of the capsule. The effective surface of the pusher is flat or concavely curved so as to fit closely against the end of the capsule and to transmit the force not only at one point (the pole or apex of the capsule end). The pusher for pushing together the capsule elements may be part of the capsule chamber and/or part of the feed mechanism for supplying the capsule from a storage magazine, in the case of an inhaler with a store of several capsules. In particular, the pusher (14) is configured so as to form a boundary of the inner space of the capsule chamber (13). In an inhaler of this kind having a storage magazine, the transporting of the capsule to the capsule chamber may take place for example from a storage shaft in which the capsules are pushed transversely through an opening tapering over a ramp and this tapering opening forces the capsule elements to be pushed further into one another. In such an embodiment, the pusher optionally acts only indirectly on the capsule—namely as a pressure ram at the top of the storage shaft.

In another embodiment with a storage magazine the capsules are forced out of a preliminary position with the pusher into the capsule. As they are pressed into the capsule chamber the capsule cap and capsule body are pushed further into one another in the manner required to open the holes.

Because of the low complexity of a pusher system and the associated low manufacturing costs, a system of this kind comprising a capsule with prefabricated, initially covered holes and a pusher integrated in a capsule chamber, is also suitable for the production of single dose inhalers (disposable items). Particularly in applications where sticky, powdered pharmaceutical preparations are to be provided for inhalation, deposits rapidly form in the capsule chamber, air outlet and mouthpiece, so that frequent changing of such a system is desirable, as by using a disposable product.

Alternatively to the systems described above comprising an inhaler and two-part capsule, the invention described here also comprises a system formed by a capsule that is open at the top and a device for inhaling dry powder. The function of the device is based on vibration of a capsule, i.e. on the Bernoulli effect, and the capsule is open at the top, with or without prefabricated holes, as desired. Prefabricated holes are preferably located in or near the base of the capsule. The capsule open at the top may be filled from a reservoir, i.e. a store of powder for a plurality of dosage units or doses, or a magazine in the form of a store for a plurality of individually measured doses within the device, or the capsules may be filled beforehand with a measured volume of powder. Thus, the device may be both a multi-dose device or a single-dose device. The capsules open at the top may be moved out of their storage state into a vibration chamber of the inhaler or—particularly in the case of a single-dose device—may also be located in the vibration chamber of the inhaler.

By the term "capsule open at the top" is meant, in general terms, a cup-shaped component that is open at one end. The shape of this cup may be as desired, including rectangular, for example, but it is preferably (like the closed capsules of the alternative systems mentioned previously) a substantially cylindrical shape in which, in particular, the closed lower end is rounded off, preferably in a hemispherical configuration, so that there are no corners. Particularly preferably, there is at least one prefabricated hole in the lower region of the cylindrical casing region of the capsule open at the top and the capsule is located in the storage state in the device in a preferably cylindrical tube which fits precisely around the capsule at the site of the hole and thus covers the hole. Preferably, in the case of a pre-filled capsule, in the storage state, the top opening of the capsule is closed off by a flat component that can be pulled away from the capsule opening in order to use the device.

The individual features of the present invention may be used independently of one another or combined with one another.

Further advantages, features, properties and aspects of the present invention will become apparent from the claims and the following description of preferred embodiments by reference to the drawings. In the drawings:

FIG. 1 shows a schematic representation of a capsule according to the invention in different states: a) capsule cap and capsule body before being fitted together, b) capsule cap and capsule body in a first insertion position and c) capsule cap and capsule body in a second insertion position;

FIG. 2 shows a schematic representation of a second embodiment of the capsule according to the invention in different states: a) capsule cap and capsule body before being fitted together, and b) capsule cap and capsule body in a second insertion position;

FIG. 3 shows a schematic representation of a third embodiment of the capsule according to the invention, wherein the capsule cap and capsule body are shown before being fitted together;

FIG. 4 shows a schematic cross-section of a fourth embodiment of the capsule according to the invention, wherein in the first half of the drawing the capsule cap and capsule body are shown before being fitted together and in the second half of the drawing the capsule cap and capsule body are shown after being fitted together.

FIG. 5 shows a schematic cross-section of a fifth embodiment of the capsule according to the invention, wherein in the first half of the drawing the capsule cap and capsule body are shown before being fitted together and in the second half of the drawing the capsule cap and capsule body are shown after being fitted together.

FIG. 11 is a schematic representation of a sixth embodiment of the capsule according to the invention in different states: FIG. 11a shows the capsule cap, capsule body and ring before they are fitted together, FIG. 11b shows the capsule cap separated from the ring and capsule body that have been pushed together, and FIG. 11c shows the capsule cap and capsule body in a second insertion position.

FIG. 12 is a schematic representation of the mode of operation of a fourth embodiment of a single-use inhaler for use with a capsule according to the invention.

FIG. 13 is a schematic representation of a seventh and an eighth embodiment of the capsule according to the invention: FIG. 13a shows the closed capsule with filling, FIG. 13b shows the position of holes in the capsule according to the seventh embodiment and FIG. 13c according to the eighth embodiment.

FIG. 14 is a schematic representation of a ninth embodiment of the capsule according to the invention with the associated mode of operation of the fifth embodiment of an inhaler.

FIG. 15 is a schematic representation of the mode of operation of a sixth embodiment of an inhaler and of the construction of the system comprising a capsule (similar to the sixth or ninth embodiment) and inhaler: FIG. 15a shows a capsule element with an associated annular holder, FIG. 15b shows the tube of the inhaler in which capsule and ring are placed, FIG. 15c shows the closure of the capsule in the tube, FIG. 15d shows an exploded view of the components or groups of components of the inhaler, FIG. 15e shows the same exploded view in schematic longitudinal section, FIG. 15f shows the finished assembled system comprising capsule and inhaler in the transporting state and FIG. 15g shows the system in the state ready for use.

FIG. 16 is a schematic representation of the mode of operation of a seventh embodiment of an inhaler and the construction of the system comprising a capsule (similar to the sixth or ninth embodiment) and inhaler: FIG. 16a shows the insertion of a capsule element into a tube, FIG. 16b shows the filling of the capsule element with powder in schematic longitudinal section through the tube, FIG. 16c shows the closure of the capsule in the tube in schematic longitudinal section through the tube, rotated through 90° compared with FIG. 16b, FIG. 16d shows an exploded view of the components or sets of components of the inhaler, FIG. 16e shows a schematic longitudinal section through the finished assembled system comprising capsule and inhaler in the transporting state and FIG. 16f shows a schematic longitudinal section through the system comprising capsule and inhaler in the state of use.

Figure 17:
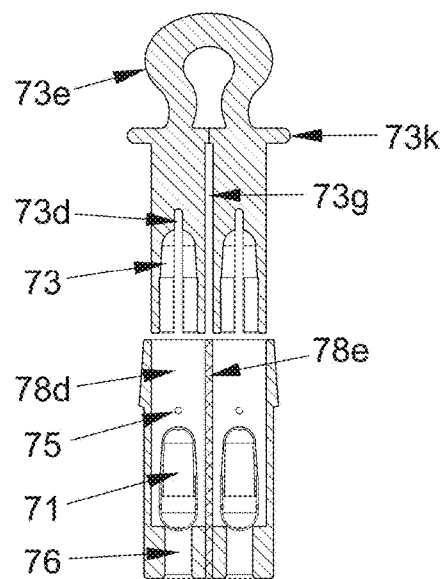

FIG. 17 is a schematic longitudinal section through a system comprising two capsules (similar to the sixth or ninth embodiment) and an inhaler according to an eighth embodiment.

FIG. 18 is a schematic representation of a tenth to fourteenth embodiment of the capsule according to the invention: FIG. 18a shows the capsule with filling, FIG. 18b shows the capsule according to the tenth, FIG. 18c the eleventh, FIG. 18d the twelfth, FIG. 18e the thirteenth and FIG. 18f the fourteenth embodiment.

Figure 19A:
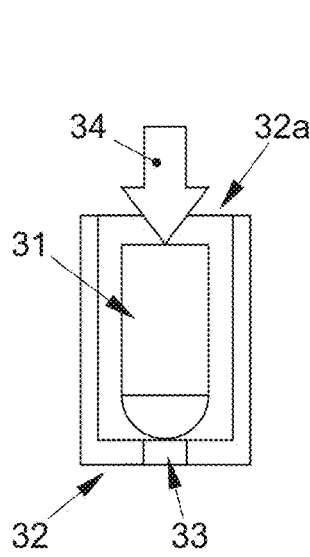
Figure 19B:
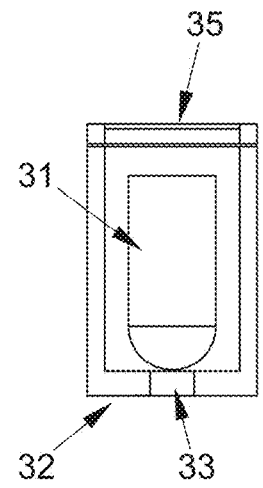
Figure 19C:
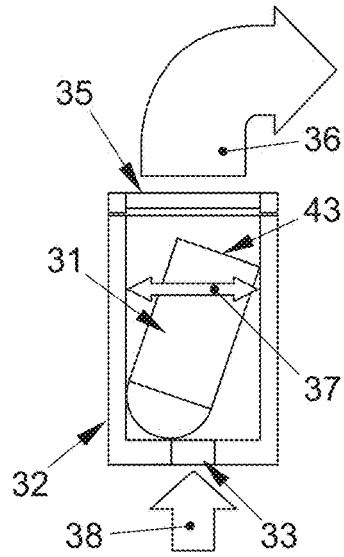

FIG. 19 is a schematic representation of the mode of operation of the ninth embodiment of an inhaler: FIG. 19a shows the filling of the capsule in the capsule chamber in the device, FIG. 19b shows the subsequent closure of the capsule chamber and FIG. 19c shows the behaviour of the capsule when the inhaler is used.

Figure 20A:
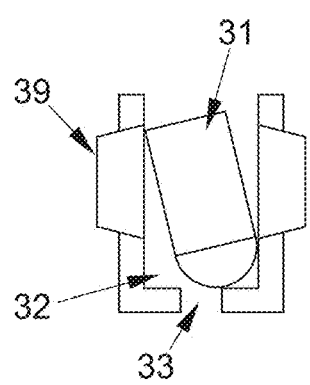
Figure 20B:
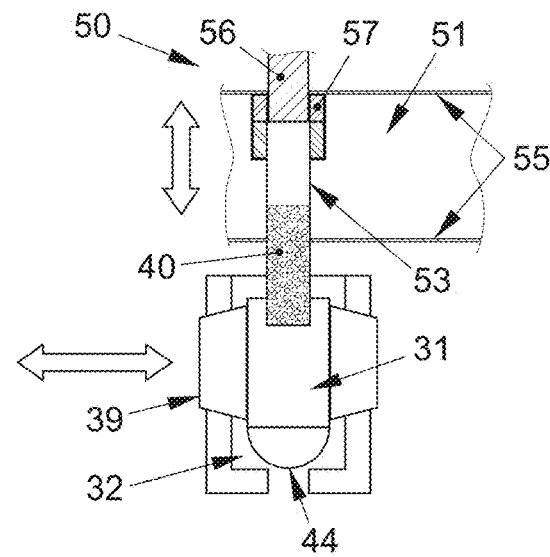

FIG. 20 is a schematic representation of the filling of the capsule in the ninth embodiment of the inhaler: FIG. 20a shows the capsule in the capsule chamber before filling and FIG. 20b during filling.

Figure 21A:
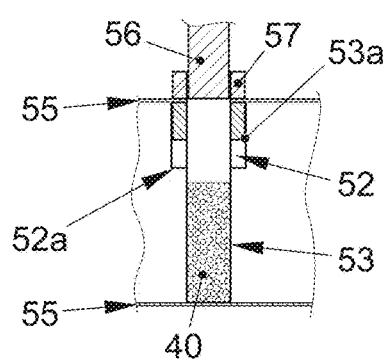
Figure 21B:
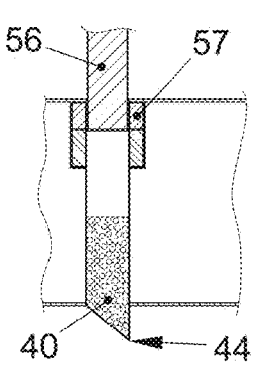
Figure 21C:
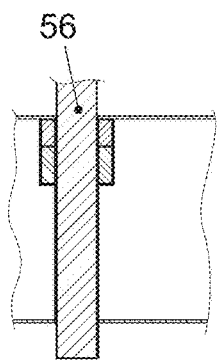

FIG. 21 is a schematic representation of the powder magazine for use in the ninth or tenth embodiment of the inhaler and the emptying of the magazine: FIG. 21a shows a dose of powder in the magazine in the storage state, FIG. 21b at the start of the emptying process and FIG. 21c at the end of the emptying process.

FIG. 22 is a schematic representation of the filling of the capsule in a tenth embodiment of the inhaler: FIG. 22a shows the capsule in the capsule chamber before filling and FIG. 22b during filling.

FIG. 23 is a schematic representation of the mode of operation of the eleventh embodiment of an inhaler: FIG. 23a shows the open capsule with a prefabricated hole, FIG. 23b the open capsule stored in an inhaler and FIG. 23c the open capsule after it has been moved out of its storage state into the capsule chamber of the inhaler.

FIG. 1 schematically shows a capsule according to the invention consisting of a capsule cap (1) and capsule body (2) both of which are cup-shaped and can be fitted into one another telescopically by means of their openings. These and all the subsequent drawings are to be understood as being sketches in which wall thicknesses and similar details are not shown in full or in some cases are not necessarily shown to scale with one another.

The capsules shown in this and subsequent Figures are preferably filled with a powdered medicament preparation. Preferably, the capsule cap (1) and the capsule body (2) are in the form of a cylinder open at one end with a round cross-section and convex, virtually hemispherical at the other, closed end. The capsule cap (1) and capsule body (2) both preferably consist of polypropylene (PP) or polyethylene (PE), particularly preferably high-density polyethylene with a density of between 950 and 1000 kg/m$^3$. Alternatively embodiments are also possible in which the capsule cap (1) and capsule body (2) are made of different materials, for example the capsule body of PP or PE and the capsule cap of gelatine. The capsule sizes are matched to the respective inhalers or the dimensions of the capsule chambers contained therein in which they are to be inserted. Typical lengths of the assembled capsules are for example 9 mm to 22 mm with external diameters of 4 mm to 10 mm. Examples of the capsule dimensions can be found in the disclosure of WO2006/074982 A2 on page 6 lines 6 to 27. The contents of all the lines quoted are to be incorporated in full herein.

With regard to the material design of the capsule, for which all pharmaceutically acceptable plastics may be used, besides the preferred material polyethylene, reference is made in this respect to the disclosure in the application WO2006/074982 A2 on page 5, lines 6 to 31. The contents of these lines are hereby incorporated in full in the present application, including the features.

FIG. 1a shows the two separate capsule elements (1) and (2) with the prefabricated holes (6) and (7) before they are fitted together. In the embodiment shown here, during the telescopic fitting together, the capsule cap (1) is fitted onto the capsule body (2). (The opposite case of inserting the capsule cap (1) into the capsule body (2) is also feasible; in this case all the references to "inside" and "outside" that follow must be reversed). For the embodiment chosen here in which the capsule cap (1) is fitted onto the capsule body (2) the external diameter of the capsule cap (1) in the region of its cup opening is rather larger than the capsule body (2). The external diameter of the capsule body (2) at this point is comparable in size to the internal diameter of the capsule cap (1), while the diameters are matched to one another in terms of their tolerances such that when the capsule elements are joined together they fit into one another in the region of the capsule casing regions with no appreciable gaps. In the representation shown, after the capsule elements have been fitted together, the capsule body (2) thus forms the inner wall of the capsule in the region of the two abutting casing regions of the capsule elements. The capsule is filled with the preferably powder medicament preparation, e.g. by filling the preparation into the capsule body. After the filling, the capsule cap (1) is pushed onto the capsule body (2) up to a first insertion position. The arrow marked "p" in the Figures indicates the direction in which the capsule elements are, or have been, pushed together. It is further intended to symbolise the pressure that has to be applied for this pushing together.

In the first insertion position (cf. FIG. 1b) latching elements on the outer casing region of the capsule body (2) and latching elements on the inner casing region of the capsule cap (1) engage with one another. In all the Figures shown here, these latching elements are shown in the form of annularly encircling projections or beads and grooves or corrugations. Thus, the capsule body (2) in FIG. 1 has for example an outwardly directed encircling bead (5) which in the first insertion position engages in a first annularly encircling corrugation (4) on the inside of the capsule cap (1). The same effect would be achieved by an annular groove in the outer casing region of the capsule body (1), while in the insertion position an annularly encircling projection on the inner casing region of the capsule cap (1) engages in this groove. However, the latching elements do not necessarily have to be of annular configuration, but may also be formed by rather dot-like elevations in the capsule body and matching depressions in the capsule cap, or vice versa. In a preferred embodiment the capsule body comprises a plurality of dot-like, annularly arranged elevations which engage in a corresponding, preferably annularly encircling groove on the outside of the capsule cap. With regard to the design of a somewhat dot-like latching configuration, reference is made here to the disclosure of WO2006/074982 A2 on page 7 line 1 to page 8 line 32. The contents of all the lines quoted are hereby incorporated in full.

In the first insertion position (cf. FIG. 1b) the casing regions of the capsule body (2) and capsule cap (1) preferably overlap such that the casing of the capsule body (2) covers the hole (6) in the capsule cap (1) from the inside and the casing of the capsule cap (1) covers the hole (7) in the capsule body (2) from outside. The capsule is completely closed in this first insertion position.

In the second insertion position (cf. FIG. 1c) the capsule cap (1) and capsule body (2) are pushed so far into one another that the respective holes (6) and (7) are in registry with one another. The capsule is thus "opened" in this second insertion position, in the sense that powder can be expelled from the interior of the capsule. The prefabricated hole (6) in the casing region of the capsule cap (1) that is on the outside here is larger than the hole (7) of the inner casing region of the capsule body (2). The fact that one of the two holes is smaller than the other ensures that even if there are irregularities in fitting the capsule cap (1) and capsule body (2) into one another the hole diameter provided for the expulsion of the powder is not partially covered. The size of the inner hole (7) in this preferred case determines the overall size of the hole in the assembled capsule. In this way, there is no internal step on the hole on the inside of the capsule where powdered material might adhere during the expulsion process. For the second insertion position, similar latching elements to those provided for the first insertion position are provided on the capsule cap (1). Accordingly, in the embodiment shown in FIG. 1 the capsule cap (1) comprises a second corrugation (3) into which the bead (5) or other projecting latching element on the inner casing region of the capsule body (2) can engage. In this way the two holes (6) and (7) are maintained in registry and the capsule elements can no longer move relative to one another even if the capsule is moved. The latching elements needed for the first and second insertion positions may be formed for example by shaping during the injection moulding of the capsule cap (1) and capsule body (2) or may be produced on the components by material deformation. Thus, for example, a bead (5) running around the inside of the capsule body may be accompanied by a corrugation running around the outside.

In addition to the structuring of the capsule elements, which is to be regarded as macroscopic, another embodiment of the capsule according to the invention has a micro- or nanostructure or surface coating on the inside on a capsule element. This is, in particular, the capsule element that forms the outer wall of the capsule when the capsule casings are abutting on one another—the capsule cap (1) in the example of FIG. 1. The microstructure is preferably located on the inside on the casing surface facing the other capsule element. In particular, the microstructure extends over a in an annular region of the inner casing surface, this annular region forming a direct wall of the cavity of the capsule when the capsule is in the first insertion position (FIG. 1a), and abutting on the outer casing surface of the other capsule element (the capsule body (2) in the example shown in FIG. 1) when the capsule is in the second insertion position (FIG. 1c).

This microstructure gives rise to a so-called lotus effect, i.e. it reduces the adhesion of certain materials to this surface. To achieve the optimum effect, the nature of the microstructure must be selected such that it offers the least adhesion properties for the specific pharmaceutical preparation that is to be stored in the corresponding capsule type. As a result, no or very little material from the pharmaceutical preparation, for example powder, adheres to the inner wall of the capsule. This has the effect, particularly in the annular region described, that when the capsule is pushed together from the first to the second insertion position there is no friction caused by material adhering to the wall. Expansion of the microstructure to all the inner wall regions of the capsule is also possible and has the effect that no material is left behind in the capsule as a result of adhesion to the wall when the material is expelled during a nebulisation process.

The microstructure is formed by elevations and/or depressions in the surface. The elevations and/or depressions may take the form of points, hemispheres, planar surfaces, wedges, etc. They may have a random arrangement or may be ordered, e.g. in rows, circles, zigzags, in a meandering shape, etc.

The distance between the elevations on the surface structure is in the range from 0.1 to 200 microns, preferably 0.1 to 100 microns. In the case of powdered pharmaceutical preparations, structural dimensions are preferred which are less than the particles sizes of the powder. Most preferred are heights of elevations or depths of depressions in the range from 0.1 to 50 microns and distances of from 0.1 to 10 microns.

With regard to methods of producing such a microstructure and its properties, reference is made here to the disclosure of WO2004/062716 A1 on page 11 line 1 to page 13 line 13. The contents of these lines are hereby incorporated in the present application in full, including their features.

Preferred methods of applying a microstructure to inner capsule walls are those methods that do not introduce any additional material into the capsules, i.e. those microstructures that may be formed solely in the material that constitutes the respective capsule element. In the preferred case of capsule elements produced by injection moulding, the microstructures have preferably already been reproduced in mirror symmetry in the mould inserts of the injection moulding tools, so to speak, so that the capsule elements are provided with these microstructures and also the prefabricated holes during the first manufacturing step. Alternatively microstructures of this kind may be created on the inner capsule walls by subtractive surface treatment such as etching or galvanic material removal or by subsequent embossing, for example using an expandable punch that is inserted in the main opening of the capsule element.

FIG. 2 shows a second embodiment of a capsule made up of a capsule cap (1) and a capsule body (2). This embodiment differs from the first only in that the capsule cap (1) and capsule body (2) comprise a plurality of prefabricated holes (6*a*) and (6*b*) or (7*a*) and (7*b*) respectively. In the first insertion position (not shown) all these holes are closed off by the other capsule element analogously to the first embodiment. In the second insertion position (FIG. 2*b*) the respective holes (6*a*) and (6*b*) of the capsule cap (1) are in registry with the holes (7*a*) and (7*b*) of the capsule body (2), so that the capsule is opened at a number of places. In the embodiment shown two holes (6*a*, 6*b*) or (7*a*, 7*b*) are formed in the capsule cap (1) and capsule body (2), respectively, which result in two openings in the capsule in the second insertion position. However, any desired number of holes may be provided in this way. Depending on the configuration of the casing regions of the capsule cap (1) and capsule body (2) the holes may be distributed over the circumference and length of the capsule. Particularly preferably, the resulting opened capsule comprises two holes which are located on the casing region of the capsule close to the opposite ends of the capsule, i.e. at a clear spacing from one another, based on the length of the capsule.

FIG. 3 shows a third embodiment of a capsule that may be made up of a capsule cap (1) and a capsule body (2). This embodiment differs from the first only in that the holes (6) and (7) in the capsule cap (1) and capsule body (2) have an elliptical shape instead of a circular one. The longitudinal axes of these ellipses are rotated through 90° relative to one another. This ensures that in the event of irregularities during the pushing together, the openings formed by the covering process always occupy a constant overall surface area. Instead of an elliptical hole shape, correspondingly aligned oblong holes may also be used at this point.

FIGS. 4 and 5 schematically show the capsule body (2) and capsule cap (1) in cross-section and after fitting together, for various embodiments. In order that the respective holes (6) and (7) can be brought cleanly into registry when the capsule cap (1) and capsule body (2) are fitted together the capsule elements have to be fitted into one another in alignment with respect to their circumference. This requires a structure and counter-structure similar to that of a lock and key principle at the edges or respective casing surfaces of the capsule cap (1) and capsule body (2). Moreover, it is advantageous to have a longitudinal guide which ensures that after a controlled first fitting together of the capsule elements, no unwanted rotation of the capsule elements relative to one another can occur. In the embodiment shown in FIG. 4 the capsule cap (1) and capsule body (2) are similarly configured with a slightly elliptical cross-section. The elliptical shape forces the correctly oriented fitting together of the two capsule elements. When the elliptical capsule elements are brought together there are consequently two possible orientations, rotated through 180' relative to one another. Preferably, therefore, one of the two capsule elements, particularly preferably the outer one (thus in this example the capsule cap (1)), should not only comprise the at least one prefabricated hole (6) but should also comprise a duplication of the hole structure offset through 180° along the circumference of the capsule element. Thus, independently of the orientation when two elliptical capsule elements are brought together a hole (6) is always exposed when they are pushed together into the second insertion position.

In the embodiment according to FIG. 5, the outer region of the capsule body (2) in addition to the latching elements (not shown) should have a tongue (8) extending parallel to the longitudinal axis, the contour of which fits a groove (9) that is also provided longitudinally on the inside of the capsule cap (1). The capsule elements can only be pushed together in the azimuthal alignment in which the tongue (8) and the groove (9) engage in one another. The tongue (8) and the groove (9) form a guide along the entire insertion length. If desired, a plurality of tongue and groove pairs at different spacings from one another and/or of different widths may also be arranged on the casing surfaces of the capsule elements.

In an embodiment not shown here, the structural pair comprising the tongue (8) and groove (9) shown may also have a curved configuration as a result of which the pushing together of the capsule elements forces them to rotate relative to one another. This may be advantageous particularly for the objective of covering and exposing a plurality of holes in the capsule.

Figure 6:
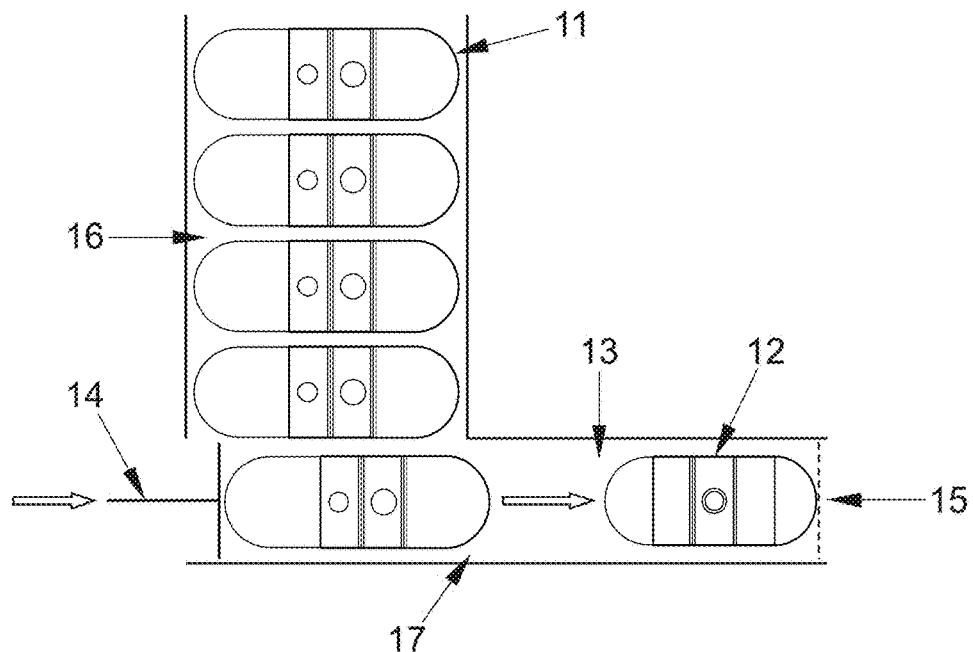
FIG. 6 is a schematic representation of the mode of operation of an inhaler with a storage magazine for use with capsules according to the invention.
Figure 7:
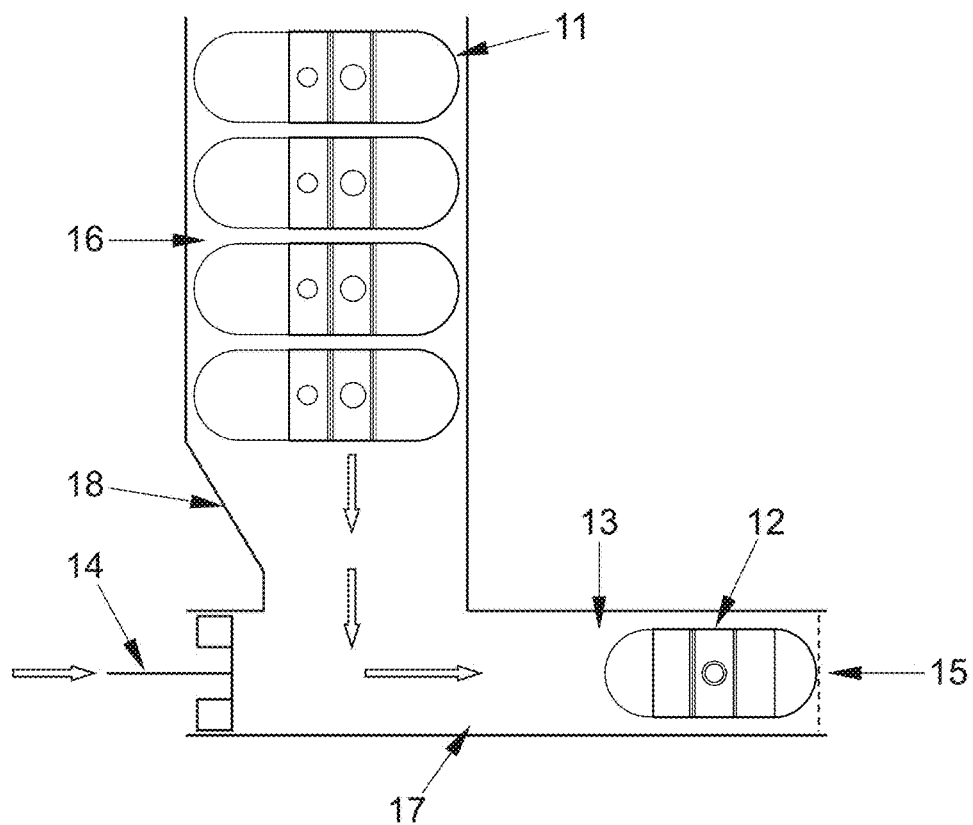
FIG. 7 is a schematic representation of the mode of operation of a second embodiment of an inhaler with a storage magazine for use with capsules according to the invention.
Figure 8A:
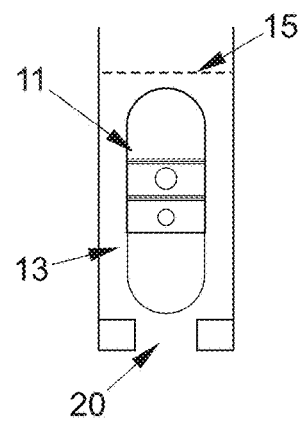
FIG. 8 is a schematic representation of the mode of operation of a single-use inhaler for use with a capsule according to the invention.
Figure 8B:
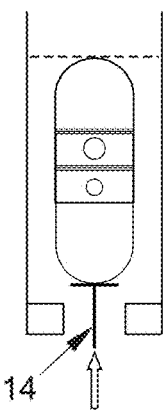
Figure 8C:
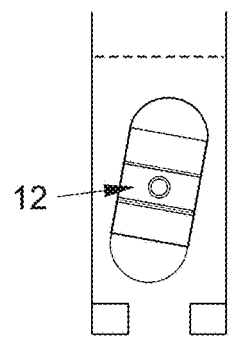

FIG. 6 schematically shows the mode of operation of an inhaler in which a plurality of capsules according to the invention are provided with prefabricated holes. In this embodiment a plurality of capsules (11) are stored in a magazine in the first insertion position (the representation of the capsule (11) in the first insertion position is not operationally faithful in FIGS. 6, 7 and 8 with regard to the position of the holes and should therefore be regarded as being purely schematic). The magazine is shown in the form of a vertical shaft (16) the cross-section of which is matched to the longitudinal extent of the capsule (11), i.e. for example rectangular or slot-shaped with widths that are only slightly greater than the length and diameter of the capsule (11). The capsules that are located in their first latching state are initially stacked in the magazine. The particular capsule (11) being used is conveyed into a channel (17), along which the air stream acting in the inhaler also passes. This conveying may either be based solely on the effect of gravity or may be assisted by spring force applied to the magazine from above. In the channel (17) the capsule (11) is pushed together into the second insertion position by a pusher (14) immediately before the inhaler is used, so that the respective holes of the capsule cap and capsule body are located above one another. The precise bringing together is ensured by corresponding dimensioning. The pusher (14) may comprise an air inlet opening and thus form the wall of the capsule chamber (13) in which the powder is to be expelled from the capsule (12) in the air stream. In this way, the inhalation of the capsule contents may take place immediately after the opening of the capsule. At the same time the pusher (14) must be locked in place by its construction so that together with the boundary of the capsule chamber (13) in the direction of pushing it forms a capsule chamber (13), the length of which is adapted to the length of the capsule (12) in its second insertion position so that the capsule (12) is able to move and vibrate in the air current in accordance with the Bernoulli effect. The pusher (14) may thus assume at least three positions in the channel (17): a first position in which a capsule (11) is conveyed from the magazine into the channel (17), a second position fully inserted in the channel (17), in which the capsule is pushed together into its second insertion position (at the same time it pushes against the bound of the capsule chamber (13) in the direction of the air outlet), and a third position which is slightly retracted relative to the second, in which the pusher forms the boundary of the capsule chamber (13) at the air inlet end during nebulisation. The boundary of the capsule chamber (13) in the direction of the air outlet is preferably formed by a screen (15) or by an aerodynamically suitably shaped component which has only slight flow resistance. Adjoining this boundary of the capsule chamber (13) containing the air inlet is a mouthpiece (not shown) at which the user (not shown either) inhales and thereby generates the air stream required to nebulise the capsule contents.

In order to be able to load the capsule chamber (13) with a new capsule (11) after the pharmaceutical preparation has been expelled from the capsule (12), a means of opening the capsule chamber (13) for removing the used capsule (12) is preferably provided on the inhaler. This means of opening may be formed for example by a closable flap in the wall of the channel (17) on the side of the capsule chamber (13) remote from the shaft (16).

FIG. 7 schematically shows the mode of operation of another embodiment of an inhaler in which a plurality of capsules according to the invention with prefabricated holes are stored. In this embodiment a plurality of capsules (11) are stored in a first insertion position in a shaft-shaped magazine. In this embodiment the shaft (16) comprises at its exit to the channel (17) or to the capsule chamber (13) a tapered portion, one wall of this tapered portion being embodied as an oblique slope or ramp or preferably as a conical guide rail (18). The shaft diameter at the end of the tapered portion or at the shaft exit corresponds to the size of the capsule (12) in the second insertion portion, i.e. in the fully assembled state. By means of pressure exerted on the capsules (11) at the top of the shaft (16)—the pressure is transferred from capsule (11) to capsule (11) from top to bottom—the uniform reduction in the diameter of the shaft forces a reduction in the capsule length, i.e. the oblique slope or ramp or conical guide rail (18) causes the capsule body (2) and capsule cap (1) to be pushed further into one another until, at the exit from the shaft, the capsule (2) is in the second insertion position.

In the embodiment shown in FIG. 7, a pusher (14) is arranged in the channel (17) at the end of the shaft (16) independently of the pushing together of the capsule (11). This pusher (14) has the main task of pushing the capsule (12) into the capsule chamber (13). Other means of transport from the magazine to the capsule chamber (13) are also possible, e.g. through flaps in the wall of the capsule chamber (13). The pusher (14) in this embodiment assumes two main positions: a first position in which the capsule (12) that has already been pushed together can be conveyed from the magazine into the channel (17) and another position in which the pusher forms the boundary of the capsule chamber (13) at the air inlet end during nebulisation and the capsule (12) in the capsule chamber (13) has room to vibrate and/or move.

FIGS. 8, 9 and 10 show schematically, by means of various embodiments, the mode of operation of an inhaler in which a capsule according to the invention with prefabricated holes is already located in a capsule chamber (13). The modes of operation shown here may indeed be applied to the filled capsule chamber of an inhaler with a plurality of stored capsules, but predominantly the embodiments shown here relate to inhalers for single use. The inhalers envisaged here consist, in principle, of only a capsule chamber (13) with a pre-inserted capsule (11), a pusher (14) that can be reset by means of a spring (19) and a mouthpiece with an inhalation channel to which an air outlet from the capsule chamber (13) is connected. The capsule chamber (13) has an air inlet in addition to said air outlet. The boundary of the capsule chamber (13) is preferably formed by a screen (15) or an aerodynamically suitably shaped component or element which presents only low flow resistance.

FIG. 8*a* shows a capsule chamber (13) of this kind with a pre-inserted capsule (11) in the first insertion position. The capsule chamber (13) has an air inlet opening (20) through which in FIG. 8*b* a ram or pusher (14) is inserted with which the capsule (11) is pushed against the screen (15), i.e. against the boundary of the capsule chamber (13) at the air outlet end. By means of further pressure directed towards the air outlet of the capsule chamber (13), the capsule cap (1) and capsule body (2) are pushed further into one another until the capsule (12) has been pushed together to its second insertion position. Then (FIG. 8*c*) the ram or pusher (14) is pulled out of the capsule chamber (13) again, and the pushed-together capsule (12) is ready for inhalation: its holes are open for the expulsion of the preferably powdered material contained therein and it has room to vibrate and/or move in the capsule chamber (13). In the situation of the pre-inserted capsule (11) in the first insertion position as shown in FIG. 8*a*, there is no need for any room for movement for the capsule, or it should be kept as small as possible, to prevent accidental tilting of the capsule as the ram or pusher (14) is inserted.

FIG. 9 shows an inhaler in which the pusher (14) forms part of the capsule chamber (13) in which the air outlet is integrated. The pusher (14) encompasses the boundary of the capsule chamber (13) on the air outlet side. In addition it may also telescopically form part of the side wall of the capsule chamber (13) (cf. FIG. 9); however, embodiments without this feature are also possible.

Figure 9A:
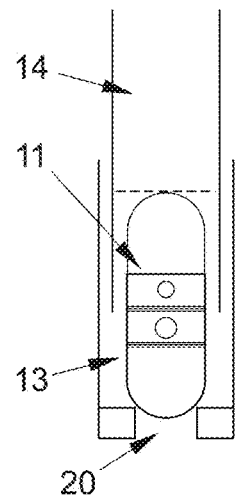
FIG. 9 is a schematic representation of the mode of operation of a second embodiment of a single-use inhaler for use with a capsule according to the invention.

FIG. 9*a* shows a preferably substantially cylindrical capsule chamber (13) with a pre-inserted capsule (11) in the first insertion position. The air inlet opening (20) is in the centre of the side of the capsule chamber (13) opposite the air outlet, i.e. in relation to the drawing, it is at the bottom of the capsule chamber (13). Preferably, the position of the pusher (14) in this situation of the pre-inserted capsule (11) is such that the capsule (11) abuts, at the top of the capsule chamber (13), on the boundary thereof, i.e. preferably on a screen (15) or an aerodynamic element, and penetrates into the air inlet opening (20) with its rounded end region at the bottom in such a way as to close off this opening (20). In this way, for example, during transportation of the inhaler after it has been removed from its outer packaging, contamination is presented from entering the capsule chamber.

Figure 9B:
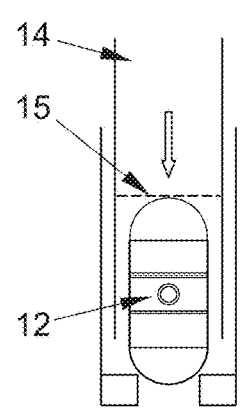

In FIG. 9*b*, the capsule (11) is pressed against its abutment in the region of the air inlet by means of the pusher (14), or more precisely by means of the boundary of the capsule chamber (13) that belongs to it, such that the capsule cap and capsule body are pushed further into one another until the second insertion position of the capsule (12) is achieved. In this embodiment the pusher (14) has not only a pushing surface in the direction of the capsule (11) but also wall regions projecting into the capsule chamber (13). The capsule chamber (13) is formed to some extent from two hollow cylinders pushed into one another with their openings, thus producing at the sides a double wall which is formed from the longitudinal wall (13*a*) of the capsule chamber (13) and the inner longitudinal wall (14*a*) of the pusher (14) inserted therein. The length of the inserted longitudinal wall (14*a*) must be matched to the length of the capsule (12) in the second insertion position so that the pusher (14) can be pushed far enough into the capsule chamber (13). After the capsule (12) has been pushed together the pusher (14) has to be pulled back into its starting position and locked in place so that the length of the capsule chamber (13) is firmly fixed for the movement of the capsule during inhalation and is thus also defined. Preferably, to prevent secondary air during inhalation, a sliding seal is formed or inserted between the pushed-in longitudinal wall (14*a*) of the pusher (14) and the longitudinal wall (13*a*) of the capsule chamber (13) that receives it.

Preferably, the inhaler according to the mode of operation shown in FIG. 9 consists of two components, besides the capsule (11), which are fitted telescopically into one another in order to expose the holes in the capsule (11) and are pulled apart again for the subsequent use of the inhaler: a component which contains the part of the capsule chamber (13) having the air inlet, and another component that contains the part of the capsule chamber (13) having the air outlet, the inhalation channel and preferably also the mouthpiece attached thereto. Preferably, both components are made in one piece from injection moulded plastics, for example. Depending on the configuration of the gripping surfaces on the outside of the inhaler, one of the two components in this embodiment may be referred to as the "pusher": either the inhaler is configured so as to be held at the bottom and the mouthpiece is pushed in as schematically shown in FIG. 9*b*, or it is configured to held at a top part comprising the mouthpiece and the other component is pushed in.

Figure 9C:
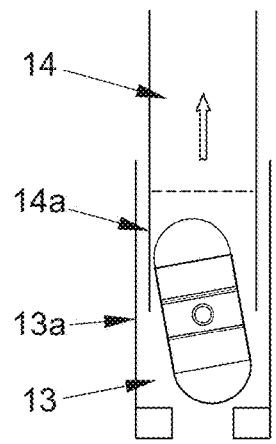
Figure 10A:
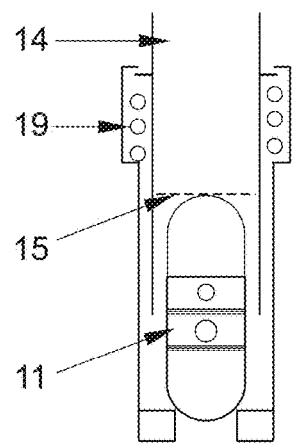
FIG. 10 is a schematic representation of the mode of operation of a third embodiment of a single-use inhaler for use with a capsule according to the invention.
Figure 10B:
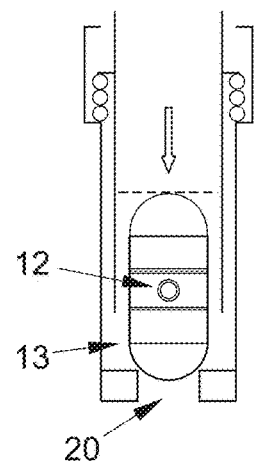
Figure 10C:
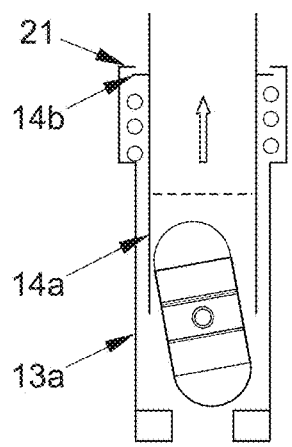

FIGS. 10*a*, 10*b* and 10*c* show an inhaler corresponding to the one shown in FIGS. 9*a*, 9*b* and 9*c*, the inhaler in FIG. 10 differing from the previous ones only in that it comprises a spring (19) which causes the two components to be reset after being pushed together into one another. In this embodiment the pusher (14) has an outer projection (14*b*) with which the spring (19) can be compressed counter to spring force when the pusher (14) is pushed into the capsule chamber (13). When the external pressure on the pusher (14) has ended, the spring (19) forces the pusher (14) back outwards beyond its projection (14*b*), as far as is permitted by an abutment edge (21) which belongs to the holder for the spring (19) in the inhaler and limits the maximum extension of the spring (19).

FIG. 11 schematically shows another embodiment of a capsule according to the invention consisting of a capsule cap (1), capsule body (2) and a ring (22). The capsule cap (1) and capsule body (2) are both also cup-shaped analogously to the embodiment shown in FIG. 1 and can be telescopically fitted into one another through their openings, while in this respect aspects described with reference to FIG. 1 are also valid here. For reasons of easier filling, the Example shown in FIG. 11, unlike the other examples of representations, shows an embodiment in which the capsule cap (1) is pushed into the capsule body (2). However, embodiments with a cap pushed on externally are also possible). The capsule body (2) with a larger hole (7) compared with the capsule cap (1) thus forms the outer wall of the capsule in the region of the two abutting casing regions of the capsule elements, the capsule casing regions of the two capsule elements comprise structured portions which interact with one another analogously to the previous examples.

FIG. 11*a* shows the two separate capsule elements (1) and (2) with the prefabricated holes (6) and (7) before they are fitted into one another and before they are joined with the ring (22).

FIG. 11*b* shows the capsule body (2) after joining with the ring (22). The ring (22) covers the hole (7) in the capsule body (2). This is preferably the situation in which the preferably powdered pharmaceutical preparation is transferred into the capsule body (2) which is then closed off with the capsule cap as shown in FIG. 11*c*. In this design, the capsule cap (1) may be pushed into the capsule body (2) directly until the final insertion position is reached.

FIG. 11*c* shows the assembled capsule (11) in which, analogously to the example in FIG. 1, the capsule cap (1) and capsule body (2) are latched to one another by means of latching elements (3) and (5). The prefabricated holes (6) and (7) overlap in this assembled capsule, but the resulting hole is covered by the ring (22) in this state. The capsule (11) may be stored thus or inserted in a suitable inhaler. Alternatively to the capsule (11) shown here, in this design, with the prefabricated holes (7) sealed off by means of another, for example annular, component, the capsule elements may also be configured so that after the assembly a hole (7) in the capsule body (2) does not necessarily have to be in registry with a hole (6) in the capsule cap, but in each case the capsule casing of the other capsule element in the assembled state of the capsule (11) is so short that it leaves the respective hole exposed. In this alternative embodiment (not shown) the capsule body (2) comprises a prefabricated hole (7), the capsule cap (1) has a hole (6) that fits this hole (7) and the casing of the capsule cap (1) in the assembled state of the capsule ends above the hole (7) and leaves it exposed.

FIG. 12 schematically shows the mode of operation of an inhaler the capsule chamber (13) of which is already filled with a capsule (11) according to the invention, the prefabricated holes of which are closed off from the outside by a ring, according to the principle illustrated by the embodiment in FIG. 11. In similar manner to the modes of operation shown in FIGS. 8, 9 and 10, the embodiment shown here preferably relates to a single-use inhaler.

FIG. 12 shows, similarly to FIG. 9, an inhaler in which the pusher (14) forms part of the capsule chamber (13) in which the air outlet is integrated. The pusher (14) encompasses the boundary of the capsule chamber (13) at the air outlet end. In addition, the pusher (14) telescopically forms part of the side wall of the capsule chamber (13). The internal diameter of the pushed-in longitudinal wall (14a) thus obtained is less than the external diameter of the ring (22) which closes off the prefabricated holes (6) and (7) on the capsule (11). At the same time, the diameter of the pushed-in longitudinal wall (14a) is greater than the diameter of the substantially cylindrical capsule (12) without a ring (22).

In FIG. 12b the pusher (14) is moved towards the air inlet which is located on the capsule chamber (13) at the bottom of the Figure. The lower edge of the pushed-in longitudinal wall (14a) abuts on the ring (22). As a result preferably the entire capsule (11) is initially pressed downwards so that the rounded-off lower end of the capsule (11) is introduced into the air inlet opening (20) at the bottom of the capsule chamber in such a way that the capsule as a whole is aligned upwardly and at the same time abuts on the lower abutment point, so to speak (an additional but not essential feature). As further pressure is applied to the pusher (14) from above, the ring (22) is pushed downwards on the outer casing of the capsule (12). A receptacle (23) for the ring (22) is formed or inserted in the capsule chamber (13) at the bottom. The lower edge of the inserted longitudinal wall (14a) of the pusher (14) pushes the ring (22) into this receptacle (23) over small latching elements (23a) which secure the ring (22) in its new position in the receptacle (23). In this position of the ring (22) the ring (22) has been separated from the capsule (12) and the prefabricated holes (6) and (7) located above one another are exposed.

In another embodiment (not shown in the Figure) the receptacle (23) comprises a groove that accommodates the ring (22) and forms a projection on the inside of the ring (22). By means of this projection the capsule (12) is detached from the ring (22) as the ring (22) is pressed into the groove towards the capsule chamber (13). The configuration of the projection is then preferably such that analogously to the air inlet opening in the previous embodiment it forms the lower abutment point for the capsule (12) in the capsule chamber (13).

In FIG. 12c the pusher (14) is pulled back somewhat towards the air outlet, thus giving the capsule (12) room for manoeuvre for its vibration and/or movement. The capsule is thus made ready for the delivery of the pharmaceutical preparation contained therein.

In another embodiment, a spring (19) is arranged on the pusher (14) analogously to the embodiment shown in FIG. 10, this spring (19) causing the pusher to be reset after actuation.

FIG. 13 schematically shows another embodiment of a capsule according to the invention. FIG. 13a shows the capsule as a whole with its filling. The capsule is substantially cylindrical with hemispherical upper and lower ends. The closed capsule (71) contains inside it a measured dose of the powder (40).

In FIG. 13b, holes 42a and 42b have been provided in the hemispherical upper end or cover and in the lower end or base of the capsule. For expelling the powder, particularly using the Bernoulli effect in an inhaler, at least one hole is required in the base and at least one hole in the cover of the capsule. It is also possible to use more than one hole in the base and cover. The hole sizes are preferably between 0.01 and 5 mm in diameter, preferably between 0.5 and 1.5 mm. The holes are preferably circular but may also be oval, square or of any other shape. The holes may be shaped in the injection moulding process, drilled with conventional drills or lasers, punched or formed in any other way, before the capsule is filled with powder.

In FIG. 13c the holes (72) have been placed in the parallel walls or in the cylindrical casing region of the closed capsule 71. In this way the powder can be more easily stored in the capsule with prefabricated holes as the capsule can be stored in precisely fitting manner in a cylindrical tube which then tightly seals the capsule in the casing region.

FIGS. 13b and 13c simply show variants in which the holes (42a, 42b and 72) are formed either in the hemispherical regions or in the cylindrical regions of the capsule (71). In addition, however, variants of a capsule (71) with a total of at least two holes (42a, 42b and 72) are possible, in which the hole or holes (42a, 42b or 72) is or are provided on one side of the capsule (71) in the hemispherical region and the hole or holes (42a, 42b or 72) is or are located on the other side of the capsule (71) in the cylindrical casing region. The at least two holes (42a, 42b and 72) may, moreover, be arranged offset by 180° C. or other angular units, in relation to the circular circumference of the capsule (71). Also, many variations in the distribution of varying numbers of holes (42a, 42b and 72) on the capsule (71) are also possible; for example, there may be only one hole (42a, 42b or 72) on one side (the bottom, in relation to FIG. 13b) and at least two holes (42a, 42b or 72) on the other side (the top).

Figure 14A:
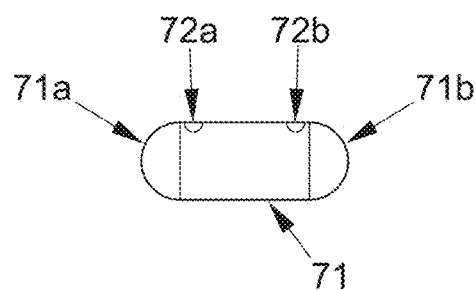
FIG. 14a shows the capsule with prefabricated holes.
Figure 14B:
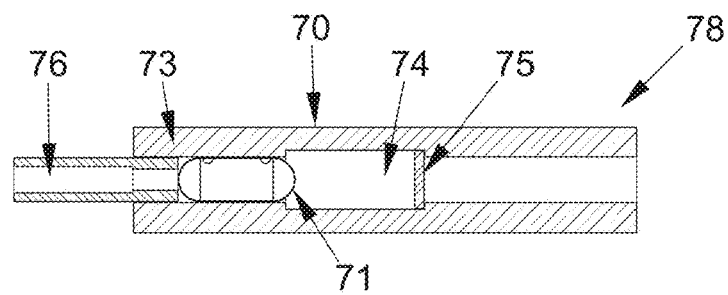
FIG. 14b shows the capsule stored in an inhaler and FIG. 14c shows the capsule after being moved from its storage state into the capsule chamber of the inhaler.

FIG. 14 schematically shows the mode of operation of a device (70) or inhaler in which a capsule (71) (FIG. 14a) with two prefabricated holes (72a, 72b) is stored in the device in such a way that the holes (72a, 72b) are closed off in the storage state (FIG. 14b) and the capsule (71) for using the device is pushed out of the storage state into a capsule chamber (74) (corresponding to the capsule chamber (13) in previous embodiments).

FIG. 14a shows the otherwise closed capsule (71) with prefabricated holes (72a, 72b). The capsule (71) is substantially cylindrical with hemispherical ends (71a, 71b). The holes (72a, 72b) are located in the parallel walls of the capsule or in the casing region of the capsule close to the hemispherical ends in each case. Analogously, in this context, capsules according to other embodiments may be used, particularly according to the capsule (11) without a ring (22) shown in FIG. 11c or the capsule shown in FIG. 13c.

FIG. 14b shows the capsule in its storage position in a device (70). In this storage position the capsule (71) is held firmly in a tube (73). This prevents powder from escaping from the capsule (71) as the inner wall of the tube covers the holes (72a, 72b). A capsule chamber (74) is formed within the device (70). The capsule chamber (74) is directly adjacent to the tube (73) and has a rather larger, preferably circular diameter than the tube (73). The capsule chamber (74) is delimited by a bar (75) or some other preferably aerodynamically shaped component in the air outlet region.

Figure 14C:
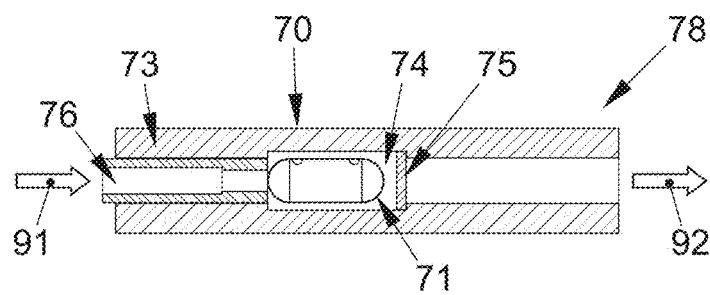

In FIG. 14c the device (70) is ready for use, i.e. it is in the state of use. The capsule (71) has been pushed through the inlet (76) into the capsule chamber (74). For this purpose, a piston shaped pusher has been inserted into the tube (73) on the side of the capsule (71) opposite the capsule chamber (74). The pushing surface of the pusher delimits the capsule chamber (74) on the side opposite the air exit, in the state of use. For use, the user breathes in through a mouthpiece (78) in the direction of the arrow (92) in the figure. Air enters the device (70) in the direction of the arrow (91) in the figure through the inlet (76), or through an air guide in the pusher which is preferably in the form of a hollow piston. In the air stream the capsule (71) vibrates in the capsule chamber (74), while the powder is expelled from the capsule (71) through the holes (72a, 72b).

In another embodiment, not shown, the capsule is already stored in the vibration chamber or capsule chamber (74) and the capsule (71) is enveloped in a preferably tubular film. The film fits closely against the cylindrical casing region of the capsule (71) and closes off the holes (72). Preferably, the materials of the film and capsule wall may be selected so that the preferably elastic and/or easily flexible film fits tightly against the capsule wall by electrostatic attraction. At one end point the capsule (71) is preferably not fixedly enclosed by the film and at the other end it projects significantly beyond the capsule (71) and/or is connected to a pull strip. This film portion projecting at the end of the capsule and/or the pull strip is located in the air inlet, in the transporting state of the inhaler, such that at this point part of the film and/or of a pull strip protrudes from the inhaler. Before the inhaler is used the film is pulled off by means of this protruding part and/or this pull strip through the air inlet of the capsule which does not fit through the air inlet. As a result the holes (72) are exposed, the capsule (71) is given full room to manoeuvre in the capsule chamber (74) and the inhaler is ready for use.

Alternatively, the protruding part of the film or the pull strip may also be located in the mouth piece of the inhaler and may be pulled out of the system through the mouth tube. Generally, the opening through which the film is pulled out of the system may also be closed off in the transporting state. In the embodiment in which the protruding film portion or the pull strip is located in the mouth tube, the mouth tube may for example be closed off by a cap fitted to the mouthpiece (78) which has to be removed before the film can be pulled out.

FIG. 15 schematically shows the construction of another embodiment of a system comprising an inhaler and capsule, the mode of operation of the system being similar to that shown in FIG. 14. The partial images 15a to 15f at the same time schematically show the sequence of the assembly of the system. First of all FIG. 15a a capsule body (2) with at least one prefabricated hole is inserted in a ring (22) which exactly surrounds the capsule body (2) in the region of its at least one prefabricated hole and thus seals the hole. Optionally, the ring (22) comprises on the inside one or preferably more small projections which, when the capsule body (2) and ring (22) are joined together define a lower position of the capsule body (2) in the ring (22), so that the capsule body (2) cannot move downwards within the ring and/or a fit is formed between the capsule body (2) and ring (22) by means of which the capsule body (2) is retained in the ring (22). Features from this embodiment relating to the ring (22) may be transferred analogously to the ring (2) from the embodiment according to FIGS. 11 and 12. FIG. 15b shows how the capsule body (2) in the ring (22) is inserted in a tube (73) from below. The tube (73) in this embodiment forms the capsule receptacle. Preferably, the ring (22) latches from inside with the tube (73) in a first latching position, e.g. in which an encircling bead (22a) or other type of latching element engages from inside the tube (73) in a corresponding recess. The tube (73) is open at its upper end so that the capsule body (2), the opening of which faces upwards when inserted in the tube (73), can be filled with powder (40) from above through the upper opening of the tube (73). FIG. 15c then shows how, after being filled with powder (40) (not shown), the capsule cap (1), which preferably also comprises at least one prefabricated hole, is inserted in the tube (73) from above and thus inside the tube (73) closes off the capsule body (2), or the capsule (71) is assembled in the tube (73). The tube (73) meanwhile surrounds the capsule cap (1) in precisely fitting manner, preferably with an upper collar (73a) so that the at least one hole (72b) in the capsule cap (1) is covered or sealed by the tube (73).

Figures 15A, 15B, 15C:
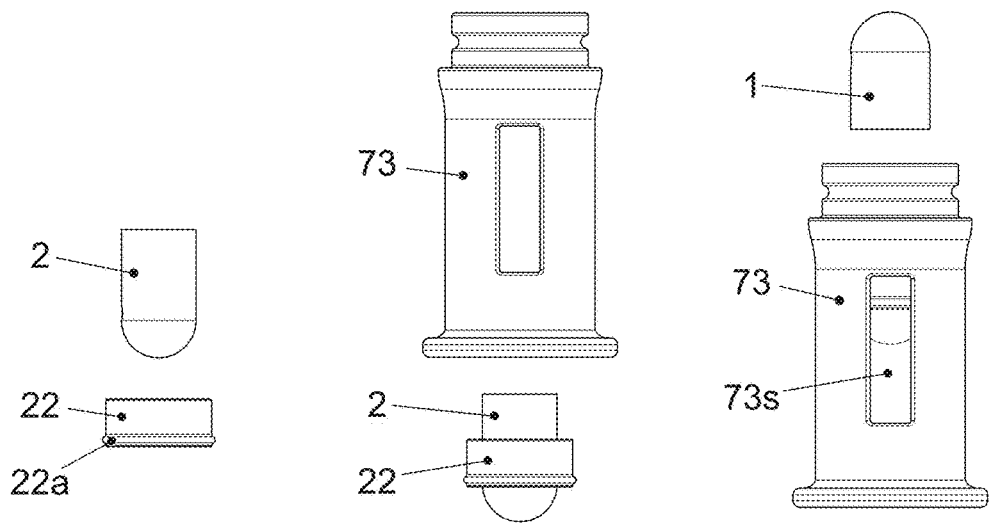
Figure 15D:
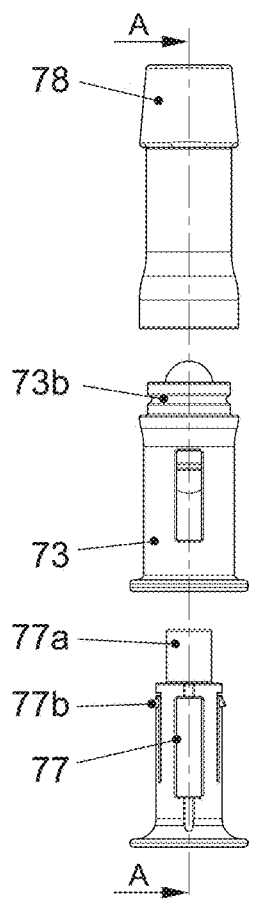
Figure 15E:
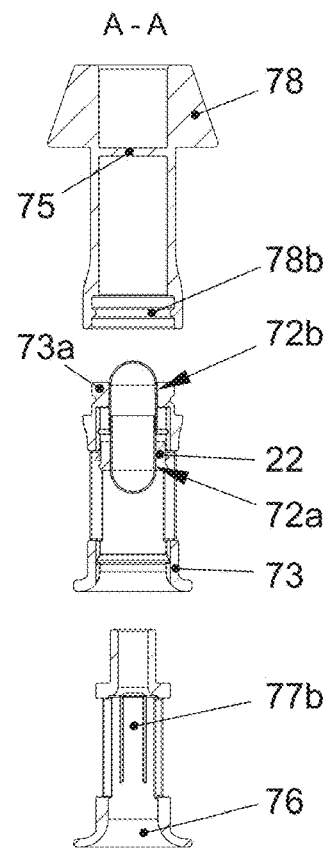

FIG. 15d and FIG. 15e show now the other components of the inhaler—mouthpiece (78) and pusher (77)—are assembled with the unit consisting of the tube (73), powder-filled capsule (71) and ring (22); the mouthpiece (78), which is preferably formed in one piece, contains the capsule chamber (74) and a bar (75) as a boundary at the top inside the capsule chamber (74). The mouthpiece is placed on the tube (73) from above, thereby latching with the tube (73). For this purpose, latching elements alternating with one another are formed on the mouthpiece (78) and tube (73), e.g. in the form of an annular bead (78b) mounted at the bottom inside the mouthpiece, this bead engaging in an equally annular corrugation (73b) on the outside, at the top of the tube (73). On the opposite side to the mouthpiece, i.e. from the bottom, in the figure, a pusher (77) is inserted in the tube (73). The pusher (77) contains an inlet (76) through which air can flow into the capsule chamber (74) later during use of the inhaler. Preferably, the pusher at (77) is embodied as a hollow piston and/or the inlet (76) is formed by a radially symmetrical passage along the main axis of the pusher (77). The pusher (77) comprises a tapered portion (77a) at its upper end, which is of such dimensions that it is able to penetrate into the ring (22).

Figure 15F:
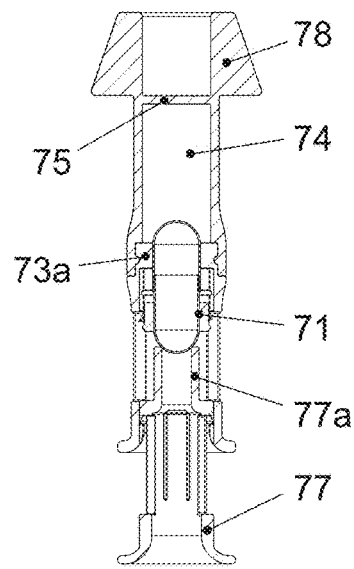

FIG. 15f shows, in schematic longitudinal section, the finished assembled system comprising the capsule (71) and inhaler in the transporting state: the capsule (71) has been pre-installed in the inhaler so that its prefabricated holes (72a), (72b) are covered or sealed off by the ring (22) and/or by the inside of the tube (73) (in the embodiment shown, having a total of two prefabricated holes (72a), (72b), one hole (72a) is sealed off by the ring (22) and one hole (72b) is sealed off by the inside of the tube). The pusher (77) projects with its lower end out of the inhaler. In order to activate the inhaler, i.e. to change the device form the transporting state to usage state, the pusher is pressed into the device at its end protruding from the bottom of the device. Preferably the lower end of the pusher (77) is broadened for this purpose so that when it is pressed with the hand it fits comfortably against the ball of the user's or patient's thumb. As it slides in, the pusher (77) preferably abuts with an annularly shaped contact surface against the capsule (71) from below and pushes the latter—as a result of it being held in the ring 22—initially together with the ring (22) further in the direction of the capsule chamber (74), until the ring (22) latches in a second latching position. As the pusher (77) is pushed further into the tube (73) the pusher (77) enters the ring (22) and with its tapered portion (77a) pushes the capsule (71) out of its close-fitting holder in the ring (22) into the capsule chamber (74). The tapered portion (77a) is preferably designed to be such a length that the tapered region of the pusher (77) can be pushed through the ring (22) and through the collar (73a) of the tube (73) until the upper edge of the pusher (77) forms the lower boundary of the capsule chamber (74). Preferably, in the pushed-in state (usage state of the inhaler, cf. FIG. 15g) the upper edge of the pusher (77) lies flush against the upper edge of the tube (73). The gap which is formed in the base of the capsule chamber (74) between the upper edge of the pusher (77) and the collar (73a) at the top of the tube (73) depending on the design of the system—e.g. as a result of a capsule cap (1) which is larger in diameter than the capsule body (2) and tapered portion (77a)—is preferably sealed by the ring (22) to prevent the ingress of secondary air. For this purpose the ring (22) consists of an at least partially elastic material and in this pushed-in state (cf. FIG. 15g) of the pusher (77) it seals off the pusher (77) against the tube (73) underneath the collar (73a).

Figure 15G:
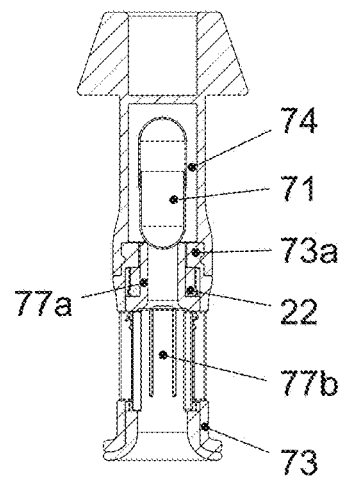

The inhaler is then ready for use, as shown in FIG. 15g: The holes (72a), (72b) are exposed and the capsule (71) has room for manoeuvre in the capsule chamber (74), as required for the vibratory movement according to the Bernoulli effect. Preferably, at least one and preferably two spring arms (77b) are formed on the side of the pusher (77), which engage in corresponding recesses (73f) on the inside of the tube (73) in the pushed-in state. By their engagement inside the tube these spring arms (77b) prevent the pusher (77) from being pulled out of the device. It is thus made clear to the user that this is a device for one-time use.

FIG. 16 schematically shows the construction of another embodiment of a system comprising an inhaler and a powder-filed capsule (71), in which, in particular, a capsule according to the embodiments shown in FIG. 11 or FIG. 14 can be used. The partial images (16a) to (16e) at the same time schematically show the sequence of assembly of the system.

First of all (FIG. 16a) a capsule body (2) with at least one prefabricated hole is inserted from above in a tube (73) which in this embodiment is essentially open only at one end, forming the capsule receptacle. The tube (73) surrounds the capsule body (2) in the region of its at least one prefabricated hole in closely fitting manner and thereby seals off the hole in the capsule body (2). The opening at one end of the capsule body (2) meanwhile faces upwards, i.e. in the direction from which the capsule body (2) has been inserted in the tube (73). Depending on the configuration of the capsule receptacle it is advantageous to insert the capsule (71) into it in correctly oriented manner. In the embodiment shown here the capsule receptacle comprises for example two longitudinally extending slots (73d) the function of which will be explained in more detail by means of the description of FIG. 16f. To ensure that the holes (72a, 72b) are sealed off by the insertion of the capsule (71) in the capsule receptacle, the capsule (71) is preferably inserted in the tube (73) in oriented manner such that the holes (72a, 72b) are not located in the region of the slots (73d). To predefine the orientation of the capsule (71) as it is inserted in the capsule receptacle, the technique described with reference to FIGS. 4 and 5 may be used. Thus, the capsule (71) and the interior of the capsule receptacle may, for example, be slightly elliptical in configuration in their short diameter. Alternatively, capsules (71) or the interior of the capsule receptacle may comprise corresponding pairs of longitudinally extending tongues and grooves: for example a longitudinal groove or longitudinal channel on the outer wall of the capsule (71) in conjunction with a longitudinally extending tongue inside the capsule receptacle.

FIG. 16b shows the filling of the capsule body (2) inside the tube (73) with powder (40) which is introduced into the opening at one end of the capsule body (2) from above. Then (FIG. 16c) the capsule cap (1) is introduced into the tube (73) from the same direction, i.e. from above, in the drawing, so that the capsule (71) is closed off inside the tube (73). FIG. 16d shows how the other components of the inhaler— mouthpiece (78) and bar (75)—are assembled with the unit consisting of the tube (73) and powder filled capsule (71): the tube (73) is inserted from above (now shown in FIG. 16d, upside down compared with FIG. 16c) through an opening in the mouthpiece (78), preferably up to a lower stop formed by the capsule chamber (74). The end from which the tube (73) is inserted is the mouth end of the mouthpiece, i.e. the end where the patient using the inhaler places their lips. After the insertion of the tube (73) in the mouthpiece (78), a bar (75) is pushed in through a guide provided laterally on the mouthpiece. The bar (75) subsequently forms the upper boundary of the capsule chamber (74) located in the mouthpiece (78). Before the insertion of the bar (75) the tube (73) has been inserted in the mouthpiece oriented so that two slots (73d) provided on the tube abut on the mouthpiece (78) inside the passage and thus allow room for the insertion of the rod (73). In this way the bar (75) can be introduced into the mouthpiece (78) so that, without being impeded by the tube (73), it penetrates through the mouthpiece (78) preferably transversely through the main axis of the device from one outer wall to the other. The oriented insertion of the tube (73) into the mouthpiece (78) is preferably predetermined by the external shape of both components. Thus, the embodiment shown comprises, for example, a mouthpiece (78) with an essentially oval or trapezoidal cross-section from the mouth end of the mouthpiece (78). The tube (73) is formed in its upper region— remote from the capsule receptacle—preferably in the form of a cap which completely covers the mouthpiece at its end destined for the mouth. This cap structure of the tube (73) forms the counterpart to the substantially oval or trapezoidal shape of the mouth end of the mouth piece (78), so as to provide orientation during insertion, as the result of the oval shape or the preferential axis of a non-circular symmetry. The cap structure of the tube (73) shown in FIG. 16 also has the additional advantage that at the mouth end the outer surfaces of the mouthpiece (78) in the regions where the patient places his lips, are covered by the tube (73) in the transporting state. Thus, even if the device is removed from its outer packaging much too early, it is ensured that the regions for lip contact remain free from contamination until the device is used.

The bar (75) forms the upper boundary of the capsule chamber (74) inside the mouthpiece (78). Apart from the bar (75), all the other components of the capsule chamber (74) are formed in one piece by the mouthpiece (78). At the lower end of the capsule chamber (74), i.e. at its end opposite the bar (75) and the mouthpiece opening, the mouthpiece comprises an inlet (76) which, in the embodiment shown, is formed as a central passage along the main axis of the system.

The inhaler shown here preferably consists of only three parts—mouthpiece (78), tube (73) and bar (75), all of which can be cheaply manufactured by plastics extrusion, so that an inhaler of this design is highly suitable for single use, i.e. as a disposable item to be discarded after one use.

FIG. 16e shows the system of inhaler and capsule (71) in the assembled state which in this case also corresponds to the transporting state. The prefabricated holes (72a, 72b) (not shown) in the capsule (71) are closed off by the inner wall of the tube (73). For capsules (71) wherein one capsule element, e.g. the capsule cap (1), has a larger external diameter than the accessible part of the other capsule element, e.g. the capsule body (2), the tube (73) has a corresponding variation in the internal diameter: the capsule element with the smaller diameter is located further inside the tube (73) than the capsule element with the larger diameter, and the internal diameter of the tube (73) is adapted to the external configuration of the capsule (71) accordingly, so that it also becomes broader stepwise from the inside to the outside. Thus in the transporting state the capsule (71) is enclosed in the system with no appreciable room for movement. For secure fitting of the tube (73) in the form of a cap on the mouthpiece (78), the tube preferably comprises in its upper region spring arms (73f) which press against the inner wall of the mouth tube (78d) from inside, in the transporting state, which forms the air outlet from the capsule chamber (74) at the mouth end of the mouthpiece (78). Preferably the mouth tube (78d) and the capsule chamber (74) have the same diameter.

In order to use the inhaler the tube (73) is pulled out of the mouthpiece (78), as shown in FIG. 16f. The slots (73d) in the tube (73) enable the tube (73) to be pulled past the bar (75). The bar (75) inserted in the mouthpiece (78) and extending transversely through the mouthpiece opening ensures that the capsule (71) remains in the capsule chamber (74) in the mouthpiece (78) and cannot be pulled out again with the tube (73). If the tube (73) is pulled out of the mouthpiece (78), the spring arms (73f) which have previously been compressed in the mouth tube (78d) preferably spread out in an outward direction such that the tube (73) cannot be reinserted in the mouthpiece (78) without destroying it (without auxiliary means). In this way the user is shown that the device is a disposable item or one way product. To make it easier for the user to pull the tube (73) of the out of mouthpiece (78), the tube (73) preferably comprises a gripping aid (73e). This gripping aid may for example be formed, as shown in FIG. 16d, by rifling on the outer lateral surface in the cap region of the tube (73) or (not shown) by a strap. This strap is preferably located centrally at the top of the cap region of the tube (73), i.e. at the opposite end to the insertion opening for the capsule (71), and contains an opening which is of such a size as to allow the user to place a finger (preferably the index finger) in the opening in order to pull the tube (73) out of the mouthpiece (78). To enable the mouthpiece to be held comfortably with the fingers of the other hand at the same time, it is preferably provided with a gripping surface (78c) which, at the moment of sliding the tube (73) out, presents the mouthpiece (78) from slipping in the hand or between the fingers. This gripping surface (78c) is preferably formed by a plurality of rounded elevations or bumps which are located in particular in the centre on the outside of two sides of the mouthpiece (78) underneath the preferably widened region for the placement of the lips.

FIG. 17 shows a system comprising an inhaler and two capsules (71). The functions in this embodiment correspond to those of the embodiment of FIG. 16, except that two capsules (71) are provided in individual capsule chambers (74). All features interacting with the capsules (71) are thus duplicated: the inhaler comprises two capsule chambers (74) with two inlets (76), to rods (75) and to tubes (73) with slots (73d). In the transporting state the walls of the tubes (73) enclose the capsule (71) such that the prefabricated holes (72) in the capsules are closed off. The two tubes (73) in the embodiment shown are preferably connected in a terminal region (73k) so as to be part of a cap which closes off the opening of the mouthpiece (78) in the transporting state, analogously to the embodiment in FIG. 16. A gripping aid (73e) is formed on this cap, which in FIG. 17 is shown as a strap with an opening. Before the inhalation, the user pulls the cap away from the mouthpiece (78) using the strap and thus arrives at the state shown in FIG. 17. The holes (72) on the capsule (71) are then opened after the tubes (73) have been removed from the capsule chambers (74) and the capsules (71) have the movement required for the desired vibration. The flow channels through the two capsule chambers are preferably not connected to one another. The inhaler thus comprises two mouth tubes (78d) which are separated from one another by a central wall (78e). The mouth tubes (78d) run parallel and open side by side in a preferably externally oval mouthpiece (78). The two tubes (73) are inserted in closely fitting manner in the two mouth tubes (78d) in the transporting state of the device, while a spacing (73g) is provided between the tubes to allow room for the central wall (78e).

Depending on the intended use of the inhaler the two capsules (71) may be identical or different in terms of their filling and/or external configuration. The use of a device with two identical capsules (71) has the advantage that double the formulation dose can be delivered with a single disposable device, thus saving the cost of disposable materials. The use of a device in which two capsules (71) with different fillings are stored is suitable particularly for use in therapies in which two active substances are administered simultaneously which, in some cases, cannot be stored in stable manner in a single formulation. A device of this kind ensures that the two active substances are taken in the correct proportion with one another. This rules out the possibility, for example, of a user taking the same preparation twice instead of taking two different preparations in one dosage cycle.

The capsules (71) and their associated capsule chambers (74), mouth tubes (78d) and tubes (73) may be adapted to the active substance or formulation dose for this purpose, for example they may be of different sizes or have different diameters and/or lengths.

FIG. 18 schematically shows further embodiments of a capsule according to the invention. FIG. 18a shows a capsule 31 with an open end (43) (upper end) and with a closed lower end (44) which contains powder (40) inside it. FIG. 18b shows the external shape of this capsule (31) without prefabricated holes. The capsule is substantially cylindrical with a hemispherical lower end (44). The upper end is preferably open but, particularly in the case of pre-filled capsules, it is possible to close it off for storage by means of a film or the like. Compared with the embodiments described previously the capsule (31) consists of only one capsule element, so to speak, namely the capsule body.

Figure 18A:
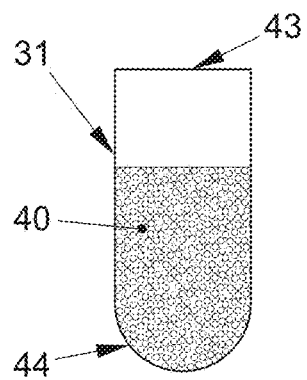
Figure 18B:
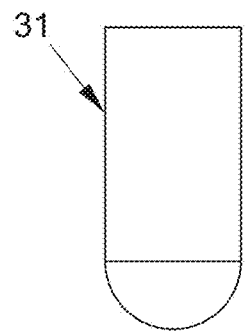
Figure 18C:
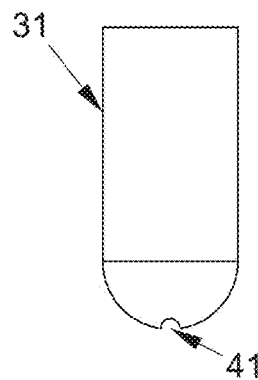
Figure 18D:
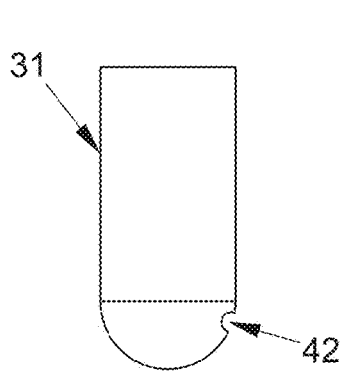
Figure 18E:
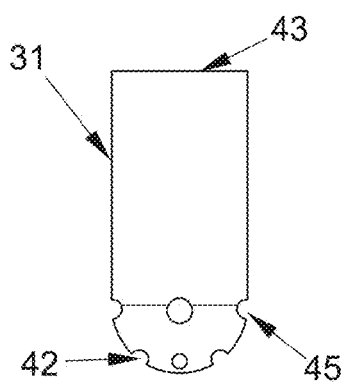
Figure 18F:
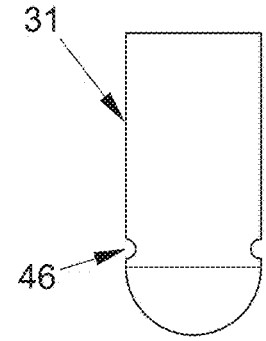

It has been found that when a hole (41) is formed in the capsule (31) as shown in FIG. 18c in the middle of the dome at the lower end (44), the dosage of powder delivered is increased but the inhalable fraction of the expelled powder is reduced. In order to increase the dosage delivered and the inhalable fraction introduced into the user's lungs, a hole (42) may be provided as in FIG. 18*d* in the lateral region of the hemispherical lower end 44.

Preferably, a plurality of holes (42), some of different sizes, are provided. A capsule (31) with a hole structure according to FIG. 18*e* has proved particularly advantageous. In this capsule (31) two groups of holes (42, 45) are distributed over the lower hemispherical end (44) of the capsule (31): a first group of holes (42) is located in a ring around the apex of the lower hemispherical end (44) and a second group of holes (45) are located in a ring further away from the apex, preferably close to or on the transition line from the capsule region with a hemispherical wall and the region with the cylindrical, i.e. parallel wall. Preferably, the holes (42, 45) are arranged in their groups equidistantly on the rings formed by them. Preferably each group of holes (42, 45) comprises 1-8 individual holes (42, 45) with hole sizes with diameters in the range from 0.01 mm to 5 mm, particularly preferably in the range from 0.1 mm to 1.5 mm. Particularly preferably, the holes (45) in the second group are bigger than the holes (42) in the first group. Most particularly preferred is a capsule (31) having four holes (42) with a diameter of 0.4±0.1 mm for the first group and four holes (45) with a diameter of 0.9±0.1 mm for the second group. With a capsule (31) of this kind opened at the top and having eight holes (42, 45) according to FIG. 18*e*, in laboratory tests for nebulising powder from capsules in vibration chambers a significantly higher inhalable fraction was achieved than with conventional field capsules having a total of only two holes. In addition, these tests demonstrated the effect that the inhalable fraction of the powder from the capsule (31) with the eight holes was less dependent on the flow rate of the air flow applied than in the conventional capsule. [By comparison the use of an open, multiply perforated capsule in a corresponding inhaler is considered.] Thus, when using the multiply perforated capsule (31) open at the top, the size of the fraction of powder breathes in by the user (or patient, in the case of a medical use under consideration here) from the capsule (31) is comparatively more independent of the breathing in process than when a conventional capsule is used.

FIG. 18*f* shows another preferred embodiment of the capsule (31) in which the hole (46) is provided in the lower cylindrical casing region close to the hemispherical region of the lower end (44) of the capsule (31). In this figure the hole (46) is thus formed in the parallel walls of the open capsule (31). In this way the powder (40) can more easily be stored in the capsule (31) with prefabricated holes (46) as the capsule can be stored in tight fitting manner in a cylindrical tube which then tightly seals the capsule (31) in the casing region (there is more on this subject in the discussion of FIG. 23). Thus after the capsule (31) has been filled the prefabricated hole can be closed off. The provision of more than one hole (46) as shown in FIG. 18*f* is also possible, e.g. in the form of two opposing holes (46).

The holes (41, 42, 46) may be formed beforehand during the injection moulding process, may be drilled with conventional drills or using lasers, punched or formed by some other suitable method before the capsule (31) is filled with powder (40).

FIG. 19 schematically shows the mode of operation of a device or inhaler in which an open capsule is filled inside the device as for example according to one of the embodiments in FIG. 18 and an air current is generated for example by the patient breathing in, setting the capsule in motion or vibration, as a result of which the powder is expelled from the capsule.

In FIG. 16*a* the capsule (31) is held inside a chamber (32) (corresponding to the capsule chamber (13) or the capsule chamber (74) in previous embodiments), the chamber comprising an inlet hole (33) in its base (corresponding to the air inlet opening (20) in previous embodiments) and is open at its upper end (32*a*). The capsule (31) is filled with powder (40) in the device (not shown) in the direction of the arrow (34). The powder (40) may be stored in a powder reservoir and may be measured into the capsule (31) by means of a measuring chamber, or it may be stored in the form of pre-measured doses in a corresponding magazine for individual dosage units and transferred as required into the open capsule (31).

In FIG. 19*b* a screen (35) or a mesh or other preferably aerodynamically shaped component is placed on the upper end of the chamber (32). This screen (35) or other component is there to hold the filled capsule (31) in position. At the same time it defines the room for movement of the capsule (31) in the chamber (32) in the upward direction.

FIG. 19*c* shows the capsule when the device is used. In FIG. 19*c* air enters through the hole (33) in the direction of the arrow (38) and passes through the screen (35) and flows in the direction of the arrow (36) into the patient's mouth. When the air flows along the capsule (31) the latter vibrates as shown by the arrow (37) and releases powder from its interior through the open end (43) and, in the case of embodiments with prefabricated holes (41, 42, 46), through the holes (41, 42, 46) as well.

FIG. 20 schematically shows how the capsule (31) open at the top can be filled in an inhaler according to the mode of operation explained with reference to FIG. 19. The embodiment under consideration here is the one where the capsule (31) is filled from a magazine (50) in which individual units of the powder (40), or individual powder doses, are stored individually in measured amounts. (An embodiment in which the capsule (31) open at the top is filled directly from a powder reservoir using a measuring device is not described in detail here. Any desired metering method for powder from multidose powder reservoirs that are available in the prior art may be used for this purpose.)

FIG. 20*a* shows the capsule (31) open at the top, in the chamber (32), in a state in which it has the room for movement required for vibration. In this embodiment, two movable cheeks (39) are set into the wall of the chamber (32) which in this state form part of the inner wall of the chamber (32). Without a flow of air in the chamber (32) the capsule (31) is located in a slightly tilted position in the chamber (32). In FIG. 20*b* the chamber (32) is shown during the filling of the capsule (31). For this purpose the cheeks (39) are pushed so far into the interior of the chamber (32) that they hold the capsule (31) in an upright position from both sides (the direction of the horizontal arrows represents the movement of the cheeks (39). The capsule (31) is thus able to align itself with its lower hemispherical end (44) on the inlet hole (33) in the centre of the bottom of the chamber (32) so that its upper opening faces straight upwards. Other alignment means such as for example a cheek (39) that presses the capsule (31) against a wall of the chamber (32) are alternatively possible. FIG. 20*b* shows how the capsule (31) is filled from above with powder (40) from a magazine (50)—which is shown only in part in the figures. The magazine (50) is configured so as to comprise a plurality of receptacles (52) for individually measured powdered doses. Preferably the magazine (50) is in the form of an in particular annular carrier (51) with receptacles (52) arranged equidistantly thereon, which are embodied as passages parallel to the axis of the annular carrier (51). Inserts (53) are preferably set into the receptacles, in which the powder is located in the form of measured dosage units. The individual dosage units are sealed in the storage state, preferably by film-like seals (55) applied particularly to both flat sides of the carrier (51), closing off the upper and lower openings of the receptacles (52). In order to transfer a unit of the powder (40) from the magazine (50) into the capsule (31) that is open at the top a technique similar to dosing by means of a pipette is used: in this embodiment a punch (56) with an associated punch ring (57) is placed on the respective receptacles (52) from which the powder is to be transferred into the capsule (31) and is pressed towards the capsule (32). Details of this procedure are illustrated in FIGS. 21*a*-*c*. FIG. 21*a* shows the punch (56) placed on the receptacle (52) with the punch ring (57) before the start of the movement for expelling the powder from the receptacle (52). The insert (53) in which the powder (40) is contained is preferably in the form of a cylindrical tube on the inside. On the outside, this tube has a projection (53*a*) at its upper end, while in the comparatively longer lower part the insert (53) has a smooth cylindrical outer wall with a smaller diameter than the projection (53*a*).

In the first part of this movement (illustrated in FIG. 21*b*) the punch (56) and punch ring (57) move together as a result of pressure from above. The punch ring (57) presses the insert (53) on the projection (53*a*) into the receptacle (52) or inside the receptacle (52) and downwards until the lower edge of the projection (53*a*) meets an abutment (52*a*) in the receptacle (52). Underneath this projection (52*a*) the receptacle 52 surrounds the longer lower region of the insert (53) preferably in a sliding fit. The punch ring (57), the projection (53*a*) and hence the entire insert (53) have now arrived at the end of their downward movement. The insert (53) preferably has a point at its lower end and in particular it is in the form of a hollow needle or cannula with a bevelled point with which it pierces the lower film (55) as it moves downwards. The film is thereby pierced so far or moves sideways to such an extent that there is no longer any foil material in front of the lower opening of the insert (53).

As the movement continues the punch (56) then moves independently of the punch ring (57) and slides downwards inside the insert (53) and forces the powder (40) completely out of the insert (53) as shown in FIG. 21 *c* and hence into the upwardly open capsule (31) located underneath. The interior of the insert (53) and the exterior of the punch (56) are of such dimensions as to ensure a sliding fit.

FIG. 22 schematically shows an embodiment of an inhaler wherein a capsule (31) open at the top is pushed into a filling chamber (32*b*) to fill said capsule with powder (40) from the chamber (32). This mechanism may for example be embodied so that the pusher (not shown) used to move the capsule (31) presses the capsule (31) against the wall of the filling chamber (32*b*) so that the capsule (31) is aligned upwards and is located axially underneath the respective receptacle (52) for the powder units in the magazine (50). The capsule (31) is then filled as described with reference to FIG. 22 and then returned to the chamber (32). After the filling, the powder (40) is then expelled through the screen (35) by an air current which is formed as the patient breathes in through the mouthpiece (67). The expulsion takes place analogously to the previous embodiments (cf. in particular FIG. 19). Inhalers with magazines (50) of this kind are preferably equipped with a mechanism for moving the magazine (50) onwards stepwise, which, after a receptacle (52) has been emptied, causes the next receptacle (52) to be positioned above the new capsule (31) that is to be filled. This stepwise advance may be activated for example by an actuation lever which may also trigger other processes such as, for example, movement of the capsule (31) into the filling chamber (32*b*), or may be coupled to the movement of a cap mounted on the mouthpiece (67). In both cases, the mechanism is designed so that the punch (56) with the punch ring (57) is pulled out of the magazine (50) before it is moved on.

In a stepwise advance of the magazine (50) by means of an actuating lever, the receptacle (52)—as an alternative to the axial alignment shown—may also be arranged radially in the annular carrier (51), to suit the particular mechanism used.

With regard to the constructions of the advance of a magazine (50) by means of an actuating lever reference will hereby be made to the disclosure of WO 2008 138628 with reference to FIGS. 9 and 16 used therein on page 20 line 7 to pages 23 line 17 and page 25 line 1 to page 26 line 11. The contents of these quoted lines are hereby incorporated in full for the later inclusion of features as well. In addition to the previously mentioned mechanism for the stepwise advance, the inhaler according to the invention may comprise a counter or an indicator showing the remaining doses, a device for locking the device when the last available powder dose has been reached and/or means for reinserting the pushed-out inserts (53) when the magazine (50) is advanced. With regard to the locking of the device when the last dose is reached, reference may be made for example to the disclosure of WO 2008 138628 on page 29 line 33 to page 30 line 3 and with regard to the reinsertion of the inserts, reference may be made to the disclosure of WO 2008 138628 with reference to FIG. 17 used therein, on page 31 lines 19 to 32. The contents of these quoted lines are also hereby incorporated in full.

Another technique which may be used here for stepwise advance of the magazine (50) is to couple it to the movement of a cap on the mouthpiece (67). Using a coupling of this kind the inhaler may be made user friendly so that the user or patient has only to open the cap on the mouthpiece in order to use the inhaler (67), and can then place the device directly to their lips for inhalation and after inhalation has taken place they need only close the cap once more. With regard to the construction of the advance of a magazine (50) by means of the movement of a cap which covers the mouthpiece (67) in the closed state, reference may be made by way of example to the disclosure of WO 2007 134793 with reference to FIGS. 1 and 4 used therein on page 8 line 28 to page 9 line 31, page 11 line 22 to page 12 line 36 and page 14 line 4 to page 16 line 31. The contents of these quoted lines are hereby incorporated in full, for the subsequent inclusion of features as well.

FIG. 23 schematically shows the mode of operation of a advice (60) or inhaler in which a capsule (31) (FIG. 23*a*) with a prefabricated hole (46) is stored in the device such that the hole (46) is closed off in the storage state (FIG. 23*b*), and for use of the device the capsule (31) is moved out of the storage state into a vibration chamber (65) (corresponding to the capsule chamber (13) in previous embodiments).

FIG. 23*a* shows the capsule (31) open at the top, with a prefabricated hole (46) in the parallel wall close to the hemispherical bottom of the capsule. The capsule is pre-filled with a measured dose of powder (not shown).

In FIG. 23*b* a capsule (31) is firmly stored in a cylindrical tubes (62) in the device (60). A pusher (64) with an inlet holds the capsule (31) in position a flat component (63) prevents the powder in the capsule (31) from falling out before use. It may project out of the device so that the user can pull it directly or pull a tab or the like until the capsule (31) is released inside. Preferably the flat component (63) should not be fully removed from the device (60), so as not to form an additional opening through which secondary air can penetrate into the interior of the device (60). Preferably the material of the flat component (63) should be selected so that when it abuts on the upper edge of the capsule (31) it can form a hard/soft seal, i.e. the underside of the flat component (63) facing the capsule (31) should have a certain elasticity, for example when the capsule (31) is a sold material. The device (60) comprises a vibration chamber (65) having a screen or rod (66) at its upper end. A mouthpiece (67) is arranged at right angles to the vibration chamber (65) but other orientations of the mouthpiece (67) such as for example on an axis with the vibration chamber, are also possible.

In FIG. 23c the capsule (31) has been pushed into the vibration chamber (65) after the flat component (63) has first of all being pulled out of the path and the pusher (64) with inlet as shown has been pushed into the device (60). For use, the user inhales through the mouthpiece (67), taking in air and power in the direction of the arrow (69). The air enters the device (60) through the inlet on the pusher (64) and in the direction of the arrow (68). The capsule (31) vibrates in the chamber (65), the vibration expelling the powder from the capsule (31) through the hole (46).

Some preferred components, compounds and/or formulations of the pharmaceutical preparations for use in the capsules and/or inhalers according to the invention are listed below. The compounds listed may be used per se or combined with one another in preparations.

In the compounds mentioned below, W is a pharmacologically active substance and is selected (for example) from among the betamimetics, anticholinergics, corticosteroids, PDE4-inhibitors, LTD4-receptor (CysLT1, CysLT2, CysLT3) antagonists, EGFR-inhibitors, dopamine-agonists, H1-antihistamines, PAF-antagonists, SYK-inhibitors, PDE3 inhibitors, lipoxin A4 derivatives, FPRL1 modulators, LTB4-receptor (BLT1, BLT2) antagonists, histamine H1 receptor antagonists, histamine H4 receptor antagonists, PI3 kinase inhibitors, inhibitors of non-receptor tyrosine kinases such as for example LYN, LCK, SYK, ZAP-70, FYN, BTK or ITK, inhibitors of MAP kinases such as for example p38, ERK1, ERK2, JNK1, JNK2, JNK3 or SAP, inhibitors of the NF—KB signal pathway such as for example IKK kinase inhibitors, iNOS inhibitors, MRP4 inhibitors, leukotriene biosynthesis inhibitors such as for example 5-lipoxygenase (5-LO) inhibitors, cPLA2 inhibitors, leukotriene A4 hydrolase inhibitors or FLAP inhibitors, non-steroidal anti-inflammatory agents (NSAIDs), CRTH2 antagonists, DP1-receptor modulators, thromboxane receptor antagonists, chemokine receptor antagonists of CCR1, CCR2, CCR2A, CCR2B, CCR4, CCR5, CCR6, CCR7, CCR8, CCR9, CCR10, CCR11, CXCR1, CXCR2, CXCR3, CXCR4, CXCR5, CXCR6, CX3CR1, neurokinin (NK1, NK2) antagonists, sphingosine 1-phosphate receptor modulators, modulators of adenosine receptors, modulators of purinergic receptors such as for example P2X7, histone deacetylase (HDAC) activators, bradykinin (BK1, BK2) antagonists, TACE inhibitors, mucoregulators, PPAR gamma agonists, Rho kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, TNFα antagonists, GABAa receptor antagonists, immunotherapeutics, substances to counter swelling of the airways and antitussive substances. Moreover, double or triple combinations of W may be formed. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an anticholinergic.

Examples of betamimetics which may be used here preferably include compounds which are selected from among arformoterol, carmoterol, formoterol, indacaterol, salmeterol, albuterols, bambuterol, bitolterol, broxaterol, carbuterol, clenbuterol, fenoterol, hexoprenaline, ibuterol, isoetharine, isoprenaline, levosalbutamol, mabuterol, meluadrine, metaproterenol, milveterol, orciprenaline, pirbuterol, procaterol, reproterol, rimiterol, ritodrine, salmefamol, soterenol, sulphonterol, terbutaline, tiaramide, tolubuterol, zinterol, and 6-hydroxy-8-{1-hydroxy-2-[2-(4-methoxy-phenyl)-1,1-dimethyl-ethylamino]-ethyl}-4H-benzo[1,4]oxazin-3-one 8-{2-[2-(2,4-difluoro-phenyl)-1,1-dimethyl-ethylamino]-1-hydroxy-ethyl}-6-hydroxy-4H-benzo[1,4]oxazin-3-one 8-{2-[2-(3,5-difluoro-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 8-{2-[2-(4-fluoro-phenyl)-1,1-dimethyl-ethylamino]-1-hydroxy-ethyl}-6-hydroxy-4H-benzo[1,4]oxazin-3-one N-(5-{2-[3-(4,4-diethyl-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[3-(4,4-diethyl-6-fluoro-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[3-(4,4-diethyl-6-methoxy-2-oxo-4H-benzo[d][1,3]oxazin-1-yl)-1,1-dimethyl-propylamino]-1-hydroxy-ethyl}-2-hydroxy-phenyl)-methanesulphonamide N-(5-{2-[1,1-dimethyl-3-(2-oxo-4,4-dipropyl-4H-benzo[d][1,3]oxazin-1-yl)-propylamino]-1-hydroxy-ethyl}-2-hydroxy-phenyl)-methanesulphonamide 8-{2-[1,1-dimethyl-3-(2-oxo-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(6-methyl-2-oxo-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(2-oxo-5-trifluoromethyl-2,3-dihydro-benzoimidazol-1-yl)-propylamino]-1-hydroxy-ethyl}-6-hydroxy-4H-benzo[1,4]oxazin-3-one 8-{2-[1,1-dimethyl-3-(3-methyl-2-oxo-2,3-dihydro-benzoimidazol-1-yl)-propylamino]-1-hydroxy-ethyl}-6-hydroxy-4H-benzo[1,4]oxazin-3-one N-[2-hydroxy-5-((1R)-1-hydroxy-2-{2-[4-(2-hydroxy-2-phenyl-ethylamino)-phenyl]-ethylamino}-ethyl)-phenyl]-formamide 8-hydroxy-5-((1R)-1-hydroxy-2-{2-[4-(6-methoxy-biphenyl-3-ylamino)-phenyl]-ethylamino}-ethyl)-1H-quinolin-2-one 8-hydroxy-5-[(1R)-1-hydroxy-2-(6-phenethylamino-hexylamino)-ethyl]-1H-quinolin-2-one 5-[(1R)-2-(2-{4-[4-(2-Amino-2-methyl-propoxy)-phenylamino]-phenyl}-ethylamino)-1-hydroxy-ethyl]-8-hydroxy-1H-quinolin-2-one
[3-(4-{6-[(2R)-2-hydroxy-2-(4-hydroxy-3-hydroxymethyl-phenyl)-ethylamino]-hexyloxy}-butyl)-5-methyl-phenyl]-urea
4-((1R)-2-{6-[2-(2,6-dichloro-benzyloxy)-ethoxy]-hexylamino}-1-hydroxy-ethyl)-2-hydroxymethyl-phenol
3-(4-{6-[(2R)-2-hydroxy-2-(4-hydroxy-3-hydroxymethyl-phenyl)-ethylamino]-hexyloxy}-butyl)-benzenesulphonamide
3-(3-{7-[(2R)-2-hydroxy-2-(4-hydroxy-3-hydroxymethyl-phenyl)-ethylamino]-heptyloxy}-propyl)-benzenesulphonamide
4-((1R)-2-{6-[4-(3-Cyclopentanesulfonyl-phenyl)-butoxy]-hexylamino}-1-hydroxy-ethyl)-2-hydroxymethyl-phenol
N-1-Adamantanyl-2-{3-[(2R)-2-({(2R)-2-hydroxy-2-[4-hydroxy-3-(hydroxymethyl)phenyl]ethyl}amino)propyl]phenyl}acetamide
(1R)-5-{2-[6-(2,2-difluoro-2-phenyl-ethoxy)-hexylamino]-1-hydroxy-ethyl}-8-hydroxy-1 H-quinolin-2-one
(R,S)-4-(2-{[6-(2,2-difluoro-4-phenylbutoxy)hexyl]amino}-1-hydroxy-ethyl)-2-(hydroxymethyl)phenol
(R,S)-4-(2-{[6-(2,2-difluoro-2-phenylethoxy)hexyl]amino}-1-hydroxy-ethyl)-2-(hydroxymethyl)phenol
(R,S)-4-(2-{[4,4-difluoro-6-(4-phenylbutoxy)hexyl]amino}-1-hydroxy-ethyl)-2-(hydroxymethyl)phenol
(R,S)-4-(2-{[6-(4,4-difluoro-4-phenylbutoxy)hexyl]amino}-1-hydroxy-ethyl)-2-(hydroxymethyl)phenol
(R,S)-5-(2-{[6-(2,2-difluoro-2-phenylethoxy)hexyl]amino}-1-hydroxy-ethyl)-8-hydroxychinolin-2(1H)-one
(R,S)-[2-({6-[2,2-difluoro-2-(3-methylphenyl)ethoxy]hexyl}amino)-1-hydroxyethyl]-2-(hydroxymethyl)phenol
4-(1R)-2-{[6-(2,2-difluoro-2-phenylethoxy)hexyl]amino}-1-hydroxyethyl)-2-(hydroxymethyl)phenol
(R,S)-2-(Hydroxymethyl)-4-(1-hydroxy-2-{[4,4,515-tetrafluor-6-(3-phenylpropoxy)-hexyl]amino}ethyl)phenol
(R,S)-[5-(2-{[6-(2,2-difluoro-2-phenylethoxy)hexyl]amino}-1-hydroxy-ethyl)-2-hydroxyphenyl]formamide
(R,S)-4-[2-({6-[2-(3-Bromophenyl)-2,2-difluoroethoxy]hexyl}amino)-1-hydroxyethyl]-2-(hydroxymethyl)phenol
(R,S)—N-[3-(1,1-difluoro-2-{[6-({2-hydroxy-2-[4-hydroxy-3-(hydroxymethyl)phenyl]-ethyl}amino)hexyl]oxy}ethyl)phenyl]-urea
3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione
(R,S)-4-[2-({6-[2,2-difluoro-2-(3-methoxyphenyl)ethoxy]hexyl}amino)-1-hydroxyethyl]-2-(hydroxymethyl)phenol
5-((1R)-2-{[6-(2,2-difluoro-2-phenylethoxy)hexyl]amino}-1-hydroxyethyl)-8-hydroxyquinolin-2(1H)-one
4-((1R)-2-{[4,4-difluoro-6-(4-phenylbutoxy)hexyl]amino}-1-hydroxy-ethyl)-2-(hydroxymethyl)phenol
(R,S)-4-(2-{[6-(3,3-difluoro-3-phenylpropoxy)hexyl]amino}-1-hydroxy-ethyl)-2-(hydroxymethyl)phenol
(R,S)-(2-{[6-(2,2-difluoro-2-phenylethoxy)-4,4-difluorohexyl]amino}-1-hydroxyethyl)-2-(hydroxymethyl)phenol
(R,S)-4-(2-{[6-(2,2-difluoro-3-phenylpropoxy)hexyl]amino}-1-hydroxy ethyl)-2-(hydroxymethyl)phenol
3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide
N-(2-diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide
7-[2-(2-{3-[2-(2-Chlor-phenyl)-ethylamino]-propylsulfanyl}-ethylamino)-1-hydroxy-ethyl]-4-hydroxy-3H-benzothiazol-2-one optionally in the form of their racemates, enantiomers, diastereomers and optionally in the form of the pharmacologically acceptable acid addition salts, solvates or hydrates thereof. Preferably, according to the invention, the acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of anticholinergics which may be used here preferably include compounds which are selected from among: tiotropium salts, preferably the bromide salt, oxitropium salts, preferably the bromide salt, flutropium salts, preferably the bromide salt, ipratropium salts, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthen-9-carbonyloxy)-1-azoniabicyclo[2,2,2]octane-salts. In the above-mentioned salts the cations are the pharmacologically active constituents. As $X^-$ anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide,
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide,
tropenol 9-fluoro-fluorene-9-carboxylate methobromide,
scopine 9-hydroxy-fluorene-9-carboxylate methobromide,
scopine 9-fluoro-fluorene-9-carboxylate methobromide;
tropenol 9-methyl-fluorene-9-carboxylate methobromide,
scopine 9-methyl-fluorene-9-carboxylate methobromide,
cyclopropyltropine benzilate methobromide,
cyclopropyltropine 2,2-diphenylpropionate methobromide,
cyclopropyltropine 9-hydroxy-xanthene-9-carboxylate methobromide,
cyclopropyltropine 9-methyl-fluorene-9-carboxylate methobromide,
cyclopropyltropine 9-methyl-xanthene-9-carboxylate methobromide,
cyclopropyltropine 9-hydroxy-fluorene-9-carboxylate methobromide,
cyclopropyltropine methyl 4,4'-difluorobenzilate methobromide,
tropenol 9-hydroxy-xanthene-9-carboxylate methobromide,
scopine 9-hydroxy-xanthene-9-carboxylate methobromide,
tropenol 9-methyl-xanthene-9-carboxylate-methobromide, scopine 9-methyl-xanthene-9-carboxylate-methobromide,
tropenol 9-ethyl-xanthene-9-carboxylate methobromide,
tropenol 9-difluoromethyl-xanthene-9-carboxylate methobromide,
scopine 9-hydroxymethyl-xanthene-9-carboxylate methobromide.

The above-mentioned compounds may also be used as salts within the scope of the present invention, while instead of the methobromide, the metho-X salts may be used wherein X may have the meanings given hereinbefore for X.

Compounds which may be used as corticosteroids are preferably those selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, tipredane and pregna-1,4-diene-3.20-dione, 6-fluoro-11-hydroxy-16,17-[(1-methylethylidene)bis(oxy)]-21-[[4-[(nitrooxy)methyl]benzoyl]oxy], (6α,11β,16α)-(9Cl) (NCX-1024),
16,17-butylidenedioxy-6,9-difluoro-11-hydroxy-17-(methylthio)androst-4-en-3-one (RPR-106541),
(S)-fluoromethyl 6,9-difluoro-17-[(2-furanylcarbonyl)oxy]-11-hydroxy-16-methyl-3-oxo-androsta-1,4-diene-17-carbothionate,
(S)-(2-oxo-tetrahydro-furan-3S-yl) 6,9-difluoro-11-hydroxy-16-methyl-3-oxo-17-propionyloxy-androsta-1,4-dien-17-carbothionate,
cyanomethyl 6alpha,9alpha-difluoro-11beta-hydroxy-16alpha-methyl-3-oxo-17alpha-(2,2,3,3-tetramethylcyclopropylcarbonyl)oxy-androsta-1,4-diene-17beta-carboxylate,
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, apremilast, arofyllin, atizoram, oglemilastum, tetomilast, and
5-[(N-(2,5-dichloro-3-pyridinyl)-carboxamid]-8-methoxy-quinoline (D-4418),
5-N-(3.5-dichloro-1-oxido-4-pyridinyl)-carboxamid]-8-methoxy-2-(trifluoromethyl)-quinoline (D-4396 (Sch-351591)),
N-(3,5-dichloropyrid-4-yl)-[1-(4-fluorobenzyl)-5-hydroxy-indol-3-yl]glyoxylic acid amide (AWD-12-281 (GW-842470)),
9-[(2-fluorophenyl)methyl]-N-methyl-2-(trifluoromethyl)-9H-purin-6-amine (NCS-613),
4-[(2R)-2-[3-(cyclopentyloxy)-4-methoxyphenyl]-2-phenylethyl]-pyridine (CDP-840),
N-[(3R)-3,4,6,7-tetrahydro-9-methyl-4-oxo-1-phenylpyrrolo[3.2.1-jk][1.4]benzodiazepin-3-yl]-4-pyridinecarboxamide (PD-168787),
4-[6,7-diethoxy-2.3-bis(hydroxymethyl)-1-naphthalenyl]-1-(2-methoxyethyl)-2(1H)-pyridinone (T-440),
2-[4-[6,7-diethoxy-2,3-bis(hydroxymethyl)-1-naphthalenyl]-2-pyridinyl]-4-(3-pyridinyl)-1(2H)-phthalazinone (T-2585),
(3-(3-cyclopenyloxy-4-methoxybenzyl)-6-ethylamino-8-isopropyl-3H-purine (V-11294A),
beta-[3-(cyclopentyloxy)-4-methoxyphenyl]-1,3-dihydro-1,3-dioxo-2H-isoindole-2-propanamide (CDC-801),
imidazo[1,5-a]pyrido[3.2-e]pyrazin-6(5H)-one, 9-ethyl-2-methoxy-7-methyl-5-propyl-(D-22888),
5-[3-(cyclopentyloxy)-4-methoxyphenyl]-3-[(3-methylphenyl)methyl], (3S,5S)-2-piperidinone (HT-0712),
4-[1-[3,4-bis(difluoromethoxy)phenyl]-2-(3-methyl-1-oxido-4-pyridinyl)ethyl]-alpha,alpha-bis(trifluoromethyl)-benzenemethanol (L-826141),
N-(3,5-dichloro-1-oxo-pyridin-4-yl)-4-difluoromethoxy-3-cyclopropylmethoxybenzamide,
(−)p-[(4aR*.10bS*)-9-ethoxy-1,2,3,4,4a,10b-hexahydro-8-methoxy-2-methylbenzo[s][1.6]naphthyridin-6-yl]-N,N-diisopropylbenzamide,
(R)-(+)-1-(4-bromobenzyl)-4-[(3-cyclopentyloxy)-4-methoxyphenyl]-2-pyrrolidone,
3-(cyclopentyloxy-4-methoxyphenyl)-1-(4-N'-[N-2-cyano-S-methyl-isothioureido]benzyl)-2-pyrrolidone,
cis[4-cyano-4-(3-cyclopentyloxy-4-methoxyphenyl)cyclohexane-1-carboxylic acid],
2-carbomethoxy-4-cyano-4-(3-cyclopropylmethoxy-4-difluoromethoxyphenyl)cyclohexan-1-one,
cis[4-cyano-4-(3-cyclopropylmethoxy-4-difluoromethoxyphenyl)cyclohexan-1-ol],
(R)-(+)-ethyl[4-(3-cyclopentyloxy-4-methoxyphenyl)pyrrolidin-2-ylidene]acetate,
(S)-(−)-ethyl[4-(3-cyclopentyloxy-4-methoxyphenyl)pyrrolidin-2-ylidene]acetate,
9-cyclopentyl-5.6-dihydro-7-ethyl-3-(2-thienyl)-9H-pyrazolo[3,4-c]-1,2,4-triazolo[4.3-a]pyridine,
9-cyclopentyl-5,6-dihydro-7-ethyl-3-(tert-butyl)-9H-pyrazolo[3,4-c]-1,2,4-triazolo[4.3-a]pyridine,
optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

EGFR-inhibitors which may be used are preferably compounds selected from among cetuximab, trastuzumab, panitumumab (=ABX-EGF), Mab ICR-62, gefitinib, canertinib, erlotinib, and
4-[(3-chloro-4-fluorophenyl)amino]-6-{[4-(morpholin-4-yl)-1-oxo-2-buten-1-yl]-amino}-7-cyclopropylmethoxy-quinazoline,
4-[(3-chloro-4-fluorophenyl)amino]-6-{[4-(N,N-diethyl-amino)-1-oxo-2-buten-1-yl]-amino}-7-cyclopropyl-methoxy-quinazoline,
4-[(3-chloro-4-fluorophenyl)amino]-6-{[4-(N,N-dimethyl-amino)-1-oxo-2-buten-1-yl]amino}-7-cyclopropyl-methoxy-quinazoline,
4-[(R)-(1-phenyl-ethyl)amino]-6-{[4-(morpholin-4-yl)-1-oxo-2-buten-1-yl]amino}-7-cyclopentyloxy-quinazoline,
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline,
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline,
4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline,
4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline,
4-[(3-chloro-4-fluorophenyl)amino]-6-{[4-(N,N-dimethyl-amino)-1-oxo-2-buten-1-yl]amino}-7-cyclopentyloxy-quinazoline,
4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline,
4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline,
4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline,
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline,
4-[(3-chloro-4-fluorophenyl)amino]-6-{[4-(N,N-dimethyl-amino)-1-oxo-2-buten-1-yl]amino}-7-((R)-tetrahydro-furan-3-yloxy)-quinazoline,
4-[(3-chloro-4-fluorophenyl)amino]-6-{[4-(N,N-dimethyl-amino)-1-oxo-2-buten-1-yl]amino}-7-((S)-tetrahydro-furan-3-yloxy)-quinazoline,
4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline,
4-[(3-chloro-4-fluorophenyl)amino]-6-{[4-(N-cyclopropyl-N-methyl-amino)-1-oxo-2-buten-1-yl]amino}-7-cyclopentyloxy-quinazoline,
4-[(3-chloro-4-fluorophenyl)amino]-6-{[4-(N,N-dimethyl-amino)-1-oxo-2-buten-1-yl]amino}-7-[(R)-(tetrahydro-furan-2-yl)methoxy]-quinazoline,
4-[(3-chloro-4-fluorophenyl)amino]-6-{[4-(N,N-dimethyl-amino)-1-oxo-2-buten-1-yl]amino}-7-[(S)-(tetrahydro-furan-2-yl)methoxy]-quinazoline,
4-[(3-ethynyl-phenyl)amino]-6,7-bis-(2-methoxy-ethoxy)-quinazoline,
4-[(3-chloro-4-fluorophenyl)amino]-7-[3-(morpholin-4-yl)-propyloxy]-6-[(vinylcarbonyl)amino]-quinazoline,
4-[(R)-(1-phenyl-ethyl)amino]-6-(4-hydroxy-phenyl)-7H-pyrrolo[2.3-d]pyrimidine,
3-cyano-4-[(3-chloro-4-fluorophenyl)amino]-6-{[4-(N,N-dimethylamino)-1-oxo-2-buten-1-yl]amino}-7-ethoxy-quinoline,
4-{[3-chloro-4-(3-fluoro-benzyloxy)-phenyl]amino}-6-(5-{[(2-methanesulphonyl-ethyl)amino]methyl}-furan-2-yl)quinazoline,
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline,
4-[(3-chloro-4-fluorophenyl)amino]-6-{[4-(morpholin-4-yl)-1-oxo-2-buten-1-yl]-amino}-7-[(tetrahydrofuran-2-yl)methoxy]-quinazoline,
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline,
4-[(3-ethynyl-phenyl)amino]-6-{[4-(5.5-dimethyl-2-oxo-morpholin-4-yl)-1-oxo-2-buten-1-yl]amino}-quinazoline,
4-[(3-chloro-4-fluoro-phenyl)amino]-6-[2-(2,2-dimethyl-6-oxo-morpholin-4-yl)-ethoxy]-7-methoxy-quinazoline,
4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline,
4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline,
4-[(3-chloro-4-fluoro-phenyl)amino]-6-{2-[4-(2-oxo-morpholin-4-yl)-piperidin-1-yl]-ethoxy}-7-methoxy-quinazoline,
4-[(3-chloro-4-fluoro-phenyl)amino]-6-[1-(tert.-butyloxycarbonyl)-piperidin-4-yloxy]-7-methoxy-quinazoline,
4-[(3-chloro-4-fluoro-phenyl)amino]-6-(trans-4-amino-cyclohexan-1-yloxy)-7-methoxy-quinazoline,
4-[(3-chloro-4-fluoro-phenyl)amino]-6-(trans-4-methanesulphonylamino-cyclohexan-1-yloxy)-7-methoxy-quinazoline,
4-[(3-chloro-4-fluoro-phenyl)amino]-6-(tetrahydropyran-3-yloxy)-7-methoxy-quinazoline,
4-[(3-chloro-4-fluoro-phenyl)amino]-6-(1-methyl-piperidin-4-yloxy)-7-methoxy-quinazoline,
4-[(3-chloro-4-fluoro-phenyl)amino]-6-{1-[(morpholin-4-yl)carbonyl]-piperidin-4-yl-oxy}-7-methoxy-quinazoline,
4-[(3-chloro-4-fluoro-phenyl)amino]-6-{1-[(methoxymethyl)carbonyl]-piperidin-4-yl-oxy}-7-methoxy-quinazoline,
4-[(3-chloro-4-fluoro-phenyl)amino]-6-(piperidin-3-yloxy)-7-methoxy-quinazoline,
4-[(3-chloro-4-fluoro-phenyl)amino]-6-[1-(2-acetylamino-ethyl)-piperidin-4-yloxy]-7-methoxy-quinazoline,
4-[(3-chloro-4-fluoro-phenyl)amino]-6-(tetrahydropyran-4-yloxy)-7-ethoxy-quinazoline,
4-[(3-chloro-4-fluoro-phenyl)amino]-6-((S)-tetrahydrofuran-3-yloxy)-7-hydroxy-quinazoline,
4-[(3-chloro-4-fluoro-phenyl)amino]-6-(tetrahydropyran-4-yloxy)-7-(2-methoxy-ethoxy)-quinazoline,
4-[(3-chloro-4-fluoro-phenyl)amino]-6-{trans-4-[(dimethylamino)sulphonylamino-cyclohexan-1-yloxy}-7-methoxy-quinazoline,
4-[(3-chloro-4-fluoro-phenyl)amino]-6-{trans-4-[(morpholin-4-yl)carbonylamino-cyclohexan-1-yloxy}-7-methoxy-quinazoline,
4-[(3-chloro-4-fluoro-phenyl)amino]-6-{trans-4-[(morpholin-4-yl)sulphonylamino-cyclohexan-1-yloxy}-7-methoxy-quinazoline,
4-[(3-chloro-4-fluoro-phenyl)amino]-6-(tetrahydropyran-4-yloxy)-7-(2-acetylamino-ethoxy)-quinazoline,
4-[(3-chloro-4-fluoro-phenyl)amino]-6-(tetrahydropyran-4-yloxy)-7-(2-methanesulphonylamino-ethoxy)-quinazoline,
4-[(3-chloro-4-fluoro-phenyl)amino]-6-{1-[(piperidin-1-yl)carbonyl]-piperidin-4-yloxy}-7-methoxy-quinazoline,
4-[(3-chloro-4-fluoro-phenyl)amino]-6-(1-aminocarbonylmethyl-piperidin-4-yloxy)-7-methoxy-quinazoline,
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline,
4-[(3-chloro-4-fluoro-phenyl)amino]-6-(trans-4-ethansulphonylamino-cyclohexan-1-yloxy)-7-methoxy-quinazoline,
4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline,
4-[(3-chloro-4-fluoro-phenyl)amino]-6-[1-(2-methoxy-acetyl)-piperidin-4-yloxy]-7-(2-methoxy-ethoxy)-quinazoline,
4-[(3-chloro-4-fluoro-phenyl)amino]-6-(cis-4-acetylamino-cyclohexan-1-yloxy)-7-methoxy-quinazoline,
4-[(3-ethynyl-phenyl)amino]-6-[1-(tert.-butyloxycarbonyl)-piperidin-4-yloxy]-7-methoxy-quinazoline,
4-[(3-ethynyl-phenyl)amino]-6-(tetrahydropyran-4-yloxy]-7-methoxy-quinazoline,
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline,
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline,
4-[(3-chloro-4-fluoro-phenyl)amino]-6-{cis-4-[(morpholin-4-yl)carbonylamino-cyclohexan-1-yloxy}-7-methoxy-quinazoline,
4-[(3-chloro-4-fluoro-phenyl)amino]-6-{1-[2-(2-oxopyrrolidin-1-yl)ethyl]-piperidin-4-yloxy}-7-methoxy-quinazoline,
4-[(3-chloro-4-fluoro-phenyl)amino]-6-{1-[(morpholin-4-yl)carbonyl]-piperidin-4-yloxy}-7-(2-methoxy-ethoxy)-quinazoline,
4-[(3-ethynyl-phenyl)amino]-6-(1-acetyl-piperidin-4-yloxy)-7-methoxy-quinazoline,
4-[(3-ethynyl-phenyl)amino]-6-(1-methyl-piperidin-4-yloxy)-7-methoxy-quinazoline,
4-[(3-ethynyl-phenyl)amino]-6-(1-methanesulphonyl-piperidin-4-yloxy)-7-methoxy-quinazoline,
4-[(3-chloro-4-fluoro-phenyl)amino]-6-(1-methyl-piperidin-4-yloxy)-7(2-methoxy-ethoxy)-quinazoline,
4-[(3-chloro-4-fluoro-phenyl)amino]-6-(1-isopropyloxycarbonyl-piperidin-4-yloxy)-7-methoxy-quinazoline,
4-[(3-chloro-4-fluoro-phenyl)amino]-6-(cis-4-methyl-amino-cyclohexan-1-yloxy)-7-methoxy-quinazoline,
4-[(3-chloro-4-fluoro-phenyl)amino]-6-{cis-4-[N-(2-methoxy-acetyl)-N-methyl-amino]-cyclohexan-1-yloxy}-7-methoxy-quinazoline,
4-[(3-ethynyl-phenyl)amino]-6-(piperidin-4-yloxy)-7-methoxy-quinazoline,
4-[(3-ethynyl-phenyl)amino]-6-[1-(2-methoxy-acetyl)-piperidin-4-yloxy]-7-methoxy-quinazoline,
4-[(3-ethynyl-phenyl)amino]-6-{1-[(morpholin-4-yl)carbonyl]-piperidin-4-yloxy}-7-methoxy-quinazoline,
4-[(3-chloro-4-fluoro-phenyl)amino]-6-{1-[(cis-2,6-dimethyl-morpholin-4-yl)carbonyl]-piperidin-4-yloxy}-7-methoxy-quinazoline,
4-[(3-chloro-4-fluoro-phenyl)amino]-6-{1-[(2-methyl-morpholin-4-yl)carbonyl]-piperidin-4-yloxy}-7-methoxy-quinazoline,
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline,
4-[(3-chloro-4-fluoro-phenyl)amino]-6-{1-[(N-methyl-N-2-methoxyethyl-amino)carbonyl]-piperidin-4-yloxy}-7-methoxy-quinazoline,
4-[(3-chloro-4-fluoro-phenyl)amino]-6-(1-ethyl-piperidin-4-yloxy)-7-methoxy-quinazoline,
4-[(3-chloro-4-fluoro-phenyl)amino]-6-{1-[(2-methoxyethyl)carbonyl]-piperidin-4-yloxy}-7-methoxy-quinazoline,
4-[(3-chloro-4-fluoro-phenyl)amino]-6-{1-[(3-methoxypropyl-amino)-carbonyl]-piperidin-4-yloxy}-7-methoxy-quinazoline,
4-[(3-chloro-4-fluoro-phenyl)amino]-6-[cis-4-(N-methanesulphonyl-N-methyl-amino)-cyclohexan-1-yloxy]-7-methoxy-quinazoline,
4-[(3-chloro-4-fluoro-phenyl)amino]-6-[cis-4-(N-acetyl-N-methyl-amino)-cyclohexan-1-yloxy]-7-methoxy-quinazoline,
4-[(3-chloro-4-fluoro-phenyl)amino]-6-(trans-4-methyl-amino-cyclohexan-1-yloxy)-7-methoxy-quinazoline,
4-[(3-chloro-4-fluoro-phenyl)amino]-6-[trans-4-(N-methanesulphonyl-N-methyl-amino)-cyclohexan-1-yloxy]-7-methoxy-quinazoline,
4-[(3-chloro-4-fluoro-phenyl)amino]-6-(trans-4-dimethyl-amino-cyclohexan-1-yloxy)-7-methoxy-quinazoline,
4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline,
4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline,
4-[(3-chloro-4-fluoro-phenyl)amino]-6-(1-methanesulphonyl-piperidin-4-yloxy)-7-methoxy-quinazoline,
4-[(3-chloro-4-fluoro-phenyl)amino]-6-(1-cyano-piperidin-4-yloxy)-7-methoxy-quinazoline,
3-cyano-4-[(3-chloro-4-fluorophenyl)amino]-6-{[4-(N,N-dimethylamino)-1-oxo-2-buten-1-yl]amino}-7-ethoxy-quinoline;
[4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline,
4-[(3-chloro-4-fluoro-phenyl)amino]-7-(2-{4-[(S)-(2-oxo-tetrahydrofuran-5-yl)-carbonyl]-piperazin-1-yl}-ethoxy)-6-[(vinylcarbonyl)amino]-quinazoline,
4-[(3-chloro-4-fluoro-phenyl)amino]-7-[2-((S)-6-methyl-2-oxo-morpholin-4-yl)-ethoxy]-6-[(vinylcarbonyl)amino]-quinazoline,
4-[(3-chloro-4-fluoro-phenyl)amino]-7-[4-((R)-6-methyl-2-oxo-morpholin-4-yl)-butyloxy]-6-[(vinylcarbonyl)amino]-quinazoline,
4-[(3-chloro-4-fluoro-phenyl)amino]-7-[4-((S)-6-methyl-2-oxo-morpholin-4-yl)-butyloxy]-6-[(vinylcarbonyl)amino]-quinazoline, and
4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of EGFR inhibitors are preferably compounds selected from among:
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-{[4-(N,N-dimethyl-amino)-1-oxo-2-buten-1-yl]amino}-7-((S)-tetrahydro-furan-3-yloxy)-quinazoline 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxy-carbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methane-sulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxyquinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulfonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulfonylamino]-cyclohexan-1-yloxy}-7-methoxy-quinazoline, 4-[(3-chloro-4-fluoro-phenyl)amino]-6-(tetrahydropyran-4-yloxy)-7-(2-acetylaminoethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonyl-methyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulfonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulfonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methyl-amino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethylamino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxy-ethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methyl-amino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethyl-amino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, 3-cyano-4-[(3-chloro-4-fluorophenyl)amino]-6-{[4-(N,N-dimethylamino)-1-oxo-2-buten-1-yl]amino}-7-ethoxy-quinoline

[4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline 4-[(3-chloro-4-fluoro-phenyl)amino]-7-[2-((S)-6-methyl-2-oxo-morpholin-4-yl)-ethoxy]-6-[(vinylcarbonyl)amino]-quinazoline 4-[(3-chloro-4-fluoro-phenyl)amino]-7-[4-((R)-6-methyl-2-oxo-morpholin-4-yl)-butyloxy]-6-[(vinylcarbonyl)amino]-quinazoline 4-[(3-chloro-4-fluoro-phenyl)amino]-7-[4-((S)-6-methyl-2-oxo-morpholin-4-yl)-butyloxy]-6-[(vinylcarbonyl)amino]-quinazoline 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropylmethoxy-quinazoline cetuximab, trastuzumab, ABX-EGF, Mab ICR-62, gefitinib, canertinib and erlotinib, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Dopamine receptor agonists used here are preferably compounds selected from among bromocriptin, cabergolin, alpha-dihydroergocryptin, lisuride, pergolide, pramipexol, roxindol, topinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

PAF-antagonists used here are preferably compounds selected from among lexipafant and 4-(2-chlorophenyl)-9-methyl-2-[3(4-morpholinyl)-3-propanon-1-yl]-6H-thieno-[3.2-f]-[1.2.4]triazolo[4.3-a][1.4]diazepine, 6-(2-chlorophenyl)-8.9-dihydro-1-methyl-8-[(4-morpholinyl)carbonyl]-4H.7H-cyclo-penta-[4.5]thieno-[3.2-f][1.2.4]triazolo[4.3-a][1.4]diazepine, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTB4-receptor antagonists used here are preferably compounds selected from among for example amebulant (=ethyl [[4-[[3-[[4-[1-(4-hydroxyphenyl)-1-methylethyl]phenoxy]methyl]phenyl]methoxy]phenyl]iminomethyl]-carbamate), optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used here are preferably compounds selected from among montelukast, pranlukast, zafirlukast, and (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio) propoxy]-2-propylphenoxy]butyric acid (MN-001),1-(((R)-(3-(2-(6,7-difluoro-2-quinolinyl)ethenyl)phenyl)-3-(2-(2-hydroxy-2-propyl)phenyl)thio) methylcyclopropaneacetic acid, 1-(((1(R)-3(3-(2-(2,3-dichlorothieno[3.2-b]pyridin-5-yl)-(E)-ethenyl)phenyl)-3-(2-(1-hydroxy-1-methylethyl)phenyl)propyl)thio) methyl)cyclopropaneacetic acid, [2-[[2-(4-tert-butyl-2-thiazolyl)-5-benzofuranyl]oxymethyl]phenyl]acetic acid, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4-receptor antagonists are optionally capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Histamine H1 receptor antagonists that may be used are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorophenoxamine, dimenhydrinate, diphenhydramine, promethazine, ebastine, olopatadine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists that may be used are preferably compounds such as e.g. (5-chloro-1H-indol-2-yl) (4-methyl-1-piperazinyl)-methanone (JNJ-7777120), optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Inhibitors of non-receptor tyrosine kinases that may be used such as for example LYN, LCK, SYK, ZAP-70, FYN, BTK or ITK are preferably compounds selected from among
2-[(2-aminoethyl)amino]-4-[(3-bromophenyl)amino]-5-pyrimidinecarboxamide;
2-[[7-(3,4-dimethoxyphenyl)imidazo[1,2-c]pyrimidin-5-yl] amino]-3-pyridinecarboxamide;
6-[[5-fluoro-2-[3,4,5-trimethoxyphenyl)amino]-4-pyrimidinyl]amino]-2,2-dimethyl-2H-pyrido[3.2-b]-1,4-oxazin-3 (4H)-one;
N-[3-bromo-7-(4-methoxyphenyl)-1,6-naphthyridin-5-yl]-1,3-propanediamine,
7-(4-methoxyphenyl)-N-methyl-1,6-naphthyridin-5-amine;
N-[7-(4-methoxyphenyl)-1,6-naphthyridin-5-yl]-1,3-propanediamine;
N-[7-(2-thienyl)-1,6-naphthyridin-5-yl-1,3-propanediamine;
N-[7-[4-(dimethylamino)phenyl]-1,6-naphthyridin-5-yl]-1,2-ethanediamine;
N-[7-(4-methoxyphenyl)-2-(trifluoromethyl)-1,6-naphthyridin-5-yl]-1,3-propanediamine;
N-[7-(4-methoxyphenyl)-3-phenyl-1,6-naphthyridin-5-yl]-1,3-propanediamine;
N-(7-phenyl-1,6-naphthyridin-5-yl)-1,3-propanediamine;
N-[7-(3-fluorophenyl)-1,6-naphthyridin-5-yl]-1,3-propanediamine;
N-[7-(3-chlorophenyl)-1,6-naphthyridin-5-yl]-1,3-propanediamine;
N-[7-[3-(trifluoromethoxy)phenyl]-1,6-naphthyridin-5yl]-1,3-propanediamine;
N-[7-(4-fluorophenyl)-1,6-naphthyridin-5-yl]-1,3-propanediamine;
N-[7-(4-fluorophenyl)-1,6-naphthyridin-5-yl]-1,3-propanediamine;
N-[7-(4-chlorophenyl)-1,6-naphthyridin-5-yl]-1,3-propanediamine;
N-[7-(4'-methyl[1,1'-biphenyl]-4-yl)-1,6-naphthyridin-1,3-propanediamine;
N-[7-[4-(dimethylamino)phenyl]-1,6-naphthyridin-5-yl]-1,3-propanediamine;
N-[7-[4-(diethylamino)phenyl]-1,6-naphthyridin-5-yl]-1,3-propanediamine;
N-[7-[4-(4-morpholinyl)phenyl]-1,6-naphthyridin-5-yl]-1,3-propanediamine;
N-[7-[4-[[2-(dimethylamino)ethyl]methylamino]phenyl]-1,6-naphthyridin-5-yl]-1,3-propanediamine;
N-[7-(4-bromophenyl)-1,6-naphthyridin-5-yl]-1,3-propanediamine;
N-[7-(4-methylphenyl)-1,6-naphthyridin-5-yl]-1,3-propanediamine;
N-[7-[4-(methylthio)phenyl]-1,6-naphthyridin-5-yl]-1,3-propanediamine;
N-[7-[4-(1-methylethyl)phenyl]-1,6-naphthyridin-5-yl]-1,3-propanediamine;
7-[4-(dimethylamino)phenyl]-N-methyl-1,6-naphthyridin-5-amine;
7-[4-(dimethylamino)phenyl]-N,N-dimethyl-1,6-naphthyridin-5-amine;
N-[7-[4-(dimethylamino)phenyl]-1,6-naphthyridin-5-yl]-1,4-butanediamine;
N-[7-[4-(dimethylamino)phenyl]-1,6-naphthyridin-5-yl]-1,5-pentanediamine;
3-[[7-[4-(dimethylamino)phenyl]-1,6-naphthyridin-5-yl] oxy]-1-propanol;
4-[5-(4-aminobutoxy)-1,6-naphthyridin-7-yl]-N,N-dimethyl-benzenamine;
4-[[7-[4-(dimethylamino)phenyl]-1,6-naphthyridin-5-yl] amino]-1-butanol;
N-[7-[4-(dimethylamino)phenyl]-1,6-naphthyridin-5-yl]-N-methyl-1,3-propanediamine;
N-[7-[4-(dimethylamino)phenyl]-1,6-naphthyridin-5-yl]-N'-methyl-1,3-propanediamine;
N-[7-[4-(dimethylamino)phenyl]-1,6-naphthyridin-5-yl]-N,N'-dimethyl-1,3-propanediamine;

1-amino-3-[[7-[4-(dimethylamino)phenyl]-1,6-naphthyridin-5-yl]amino]-2-propanol;
N-[7-[4-(dimethylamino)phenyl]-1,6-naphthyridin-5-yl]-2,2-dimethyl-1,3-propanediamine;
7-[4-(dimethylamino)phenyl]-N-(3-pyridinylmethyl)-1,6-naphthyridin-5-amine;
N-[(2-aminophenyl)methyl]-7-[4-(dimethylamino)phenyl]-1,6-naphthyridin-5-amine;
N-[7-[6-(dimethylamino)[1,1'-biphenyl]-3-yl]-1,6-naphthyridin-5-yl]-1,3-propanediamine;
N-[7-[3-chloro-4-(diethylamino)phenyl]-1,6-naphthyridin-5-yl]-1,3-propanediamine;
N-[7-[4-(dimethylamino)-3-methoxyphenyl]-1,6-naphthyridin-5-yl]-1,3-propanediamine;
N-[7-[4-(diethylamino)phenyl]-3-methyl-1,6-naphthyridin-5-yl]-1,3-propanediamine;
N-[7-(3'-fluoro[1,1'-biphenyl]-3-yl)-1,6-naphthyridin-5-yl]-1,2-ethanediamine,
N-[7-(4-methoxyphenyl)-1,6-naphthyridin-5-yl]-1,6-naphthyridine-1,3-propanediamine;
N,N'-bis(3-aminopropyl)-7-(4-methoxyphenyl)-2,5-diamine;
N-[7-(4-methoxyphenyl)-2-(phenylmethoxy)-1,6-naphthyridin-5-yl]-1,6-naphthyridine-1,3-propanediamine;
N5-(3-aminopropyl)-7-(4-methoxyphenyl)-N2-(phenylmethyl)-2,5-diamine;
N-[7-(2-naphthalenyl)-1,6-naphthyridin-5-yl]-1,3-propanediamine;
N-[7-(2'-fluoro[1,1'-biphenyl]-4-yl)-1,6-naphthyridin-5-yl]-1,3-propanediamine;
N-[7-(3.4,5-trimethoxyphenyl)-1,6-naphthyridin-5-yl]-1,3-propanediamine;
N-[7-(3,4-dimethylphenyl)-1,6-naphthyridin-5-yl]-1,3-propanediamine;
1-amino-3-[[7-(2-naphthalenyl)-1,6-naphthyridin-5-yl]amino]-2-propanol;
1-amino-3-[[7-(2'-fluoro[1,1'-biphenyl]-4-yl)-1,6-naphthyridin-5-yl]amino]-2-propanol;
1-amino-3-[[7-(4'-methoxy[1,1'-biphenyl]-4-yl)-1,6-naphthyridin-5-yl]amino]-2-propanol;
1-amino-3-[[7-(3.4,5-trimethoxyphenyl)-1,6-naphthyridin-5-yl]amino]-2-propanol;
1-amino-3-[[7-(4-bromophenyl)-1,6-naphthyridin-5-yl]amino]-2-propanol;
N-[7-(4'-methoxy[1,1'-biphenyl]-4-yl)-1,6-naphthyridin-5-yl]-2,2-dimethyl-1,3-propanediamine;
1-[[7-[4-(dimethylamino)phenyl]-1,6-naphthyridin-5-yl]amino]-2-propanol;
2-[[2-[[7-[4-(dimethylamino)phenyl]-1,6-naphthyridin-5-yl]amino]ethyl]thio]-ethanol;
7-[4-(dimethylamino)phenyl]-N-(3-methyl-5-isoxazolyl)-1,6-naphthyridin-5-amine;
7-[4-(dimethylamino)phenyl]-N-4-pyrimidinyl-1,6-naphthyridin-5-amine;
N-[7-[4-(dimethylamino)phenyl]-1,6-naphthyridin-5-yl]-1,3-cyclohexanediamine;
N,N-dimethyl-4-[5-(1-piperazinyl)-1,6-naphthyridin-7-yl]-benzenamine;
4-[5-(2-methoxyethoxy)-1,6-naphthyridin-7-yl]-N,N-dimethyl-benzenamin;
1-[7-[4-(dimethylamino)phenyl]-1,6-naphthyridin-5-yl]-4-piperidinol;
1-[7-[4-(dimethylamino)phenyl]-1,6-naphthyridin-5-yl]-3-pyrrolidinol;
7-[4-(dimethylamino)phenyl]-N-(2-furanylmethyl)-1,6-naphthyridin-5-amine;
7-[4-(dimethylamino)phenyl]-N-[3-(1H-imidazol-1-yl)propyl]-1,6-naphthyridin-5-amine;
1-[7-[4-(dimethylamino)phenyl]-1,6-naphthyridin-5-yl]-4-piperidinecarboxamide;
1-[3-[[7-[4-(dimethylamino)phenyl]-1,6-naphthyridin-5-yl]amino]propyl]-2-pyrrolidinone;
N-[3'-[5-[(3-aminopropyl)amino]-1,6-naphthyridin-7-yl][1,1'-biphenyl]-3-yl]-acetamide;
N-[7-(4'-fluoro[1,1'-biphenyl]-4-yl)-1,6-naphthyridin-5-yl]-1,3-propanediamine;
N-[4'-[5-[(3-aminopropyl)amino]-1,6-naphthyridin-7-yl][1,1'-biphenyl]-3-yl]-acetamid;
N-[7-[4-(1,3-benzodioxol-5-yl)phenyl]-1,6-naphthyridin-5-yl]-1,3-propanediamine;
N-[7-[4-(2-thienyl)phenyl]-1,6-naphthyridin-5-yl]-1,3-propanediamine;
N-[7-[4-fluoro-3-(trifluoromethyl)phenyl]-1,6-naphthyridin-5-yl]-1,3-propanediamine;
N-[7-[4-(3-pyridinyl)phenyl]-1,6-naphthyridin-5-yl]-1,3-propanediamine;
N-[7-(1,3-benzodioxol-5-yl)-1,6-naphthyridin-5-yl]-1,3-propanediamine;
N-[7-(6-methoxy-2-naphthalenyl)-1,6-naphthyridin-5-yl]-1,3-propanediamine;
7-[4-(dimethylamino)phenyl]-N-(4-pyridinylmethyl)-1,6-naphthyridin-5-amine;
3-[[7-[4-(dimethylamino)phenyl]-1,6-naphthyridin-5-yl]methylamino]-propanenitrile;
7-[4-(dimethylamino)phenyl]-N-[1-(phenylmethyl)-4-piperidinyl]-1,6-naphthyridin-5-amine;
N-[7-[4-(dimethylamino)phenyl]-1,6-naphthyridin-5-yl]-1,2-cyclohexanediamin,
N-[7-[4-(dimethylamino)phenyl]-1,6-naphthyridin-5-yl]-1,2-cyclohexanediamine,
(1R,2S)-rel-.,N-[7-[4-(dimethylamino)phenyl]-1,6-naphthyridin-5-yl]-1,2-benzenedimethanamine;
N-[7-[4-(diethylamino)phenyl]-1,6-naphthyridin-5-yl]-1,4-butanediamine;
N-[7-[3'.5'-bis(trifluoromethyl)[1,1'-biphenyl]-4-yl]-1,6-naphthyridin-5-yl].3-propanediamine;
N-[7-(3'-methoxy[1,1'-biphenyl]-4-yl)-1,6-naphthyridin-5-yl]-1,3-propanediamine;
N-[7-(3'-fluoro[1,1'-biphenyl]-4-yl)-1,6-naphthyridin-5-yl]-1,3-propanediamine;
4-[[7-[4-(dimethylamino)phenyl]-1,6-naphthyridin-5-yl]oxy]-1-butanol;
N-[7-[4-(dimethylamino)phenyl]-1,6-naphthyridin-5-yl]-1,4-cyclohexanediamine;
7-[4-(dimethylamino)phenyl]-N-(2.2.6.6-tetramethyl-4-piperidinyl)-1,6-naphthyridin-5-amine;
N-[7-[3-bromo-4-(dimethylamino)phenyl]-1,6-naphthyridin-5-yl]-1,3-propanediamine;
N-[7-(1-methyl-1H-indol-5-yl)-1,6-naphthyridin-5-yl]-1,3-propanediamine;
N-[7-[3-(trifluoromethyl)phenyl]-1,6-naphthyridin-5-yl]-1,3-propanediamine;
N-[7-[4-(trifluoromethyl)phenyl]-1,6-naphthyridin-5-yl]-1,3-propanediamine;
N-[7-(3-bromo-4-methoxyphenyl)-1,6-naphthyridin-5-yl]-1,3-propanediamine;
N-[7-[4-[[3-(dimethylamino)propyl]methylamino]phenyl]-1,6-naphthyridin-5-yl]-1,4-cyclohexanediamine;
N-[7-[4-[[2-(dimethylamino)ethyl]methylamino]phenyl]-1,6-naphthyridin-5-yl]-1,4-cyclohexanediamine;
N-[7-[4-(dimethylamino)-3-methoxyphenyl]-1,6-naphthyridin-5-yl]-1,4-cyclohexanediamine;

N-[7-[4-(4-morpholinyl)phenyl]-1,6-naphthyridin-5-yl]-1,4-cyclohexanediamine;

N-[7-[3-bromo-4-(4-morpholinyl)phenyl]-1,6-naphthyridin-5-yl]-1,4-cyclohexanediamine;

4-[[7-[4-[[2-(dimethylamino)ethyl]methylamino]phenyl]-1,6-naphthyridin-5-yl]oxy]-cyclohexanol;

N-[7-[3-bromo-4-(4-morpholinyl)phenyl]-1,6-naphthyridin-5-yl]-1,3-propanediamine;

N,N-dimethyl-4-[5-(4-methyl-1-piperazinyl)-1,6-naphthyridin-7-yl]-benzenamine;

4-[[7-[4-[[3-(dimethylamino)propyl]methylamino]phenyl]-1,6-naphthyridin-5-yl]oxy]-cyclohexanol;

N-[7-[4-[[2-(dimethylamino)ethyl]methylamino]phenyl]-1,6-naphthyridin-5-yl]-1,4-butanediamine;

1,1-dimethylethyl[3-[[5-[(3-aminopropyl)amino]-7-(4-methoxyphenyl)-1,6-naphthyridin-2-yl]amino]propyl]-carbamate, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

MAP kinase inhibitors used are preferably compounds selected from among:

bentamapimod (AS-602801),
doramapimod (BIRB-796),
5-carbamoylindole (SD-169),
6-[(aminocarbonyl)(2,6-difluorophenyl)amino]-2-(2,4-difluorophenyl)-3-pyridinecarboxamide (VX-702),
alpha-[2-[[2-(3-pyridinyl)ethyl]amino]-4-pyrimidinyl]-2-benzothiazoleacetonitrile (AS-601245),
9,12-epoxy-1H-diindolo[1,2,3-fg:3',2',1'-kl]pyrrolo[3,4-i][1.6]benzodiazocine-10-carboxylic acid (CEP-1347),
4-[3-(4-chlorophenyl)-5-(1-methyl-4-piperidinyl)-1H-pyrazole-4-yl]-pyrimidine (SC-409), optionally in the form of the racemates, enantiomers, diastereomers thereof and optionally in the form of the pharmacologically acceptable acid addition salts, solvates or hydrates thereof.

iNOS-inhibitors used are preferably compounds selected from among: S-(2-aminoethyl)isothiourea, aminoguanidine, 2-aminomethylpyridine, 5,6-dihydro-6-methyl-4H-1,3-thiazin-2-amine (AMT), L-canavanine, 2-iminopiperidine, S-isopropylisothiourea, S-methylisothiourea, S-ethylisothiourea, S-methyltiocitrulline, S-ethylthiocitrulline, L-NA (N$^\omega$-nitro-L-arginine), L-NAME (N$^\omega$-nitro-L-argininemethylester), L-NMMA (N$^\omega$-monomethyl-L-arginine), L-NIO (N$^\omega$-iminoethyl-L-ornithine), L-NIL (N$^\omega$-iminoethyl-lysine), (S)-6-acetimidoylamino-2-amino-hexanoic acid (1H-tetrazol-5-yl)-amide (SC-51), N-[[3-(aminomethyl)phenyl]methyl]-ethanimidamide (1400W), (S)-4-(2-acetimidoylamino-ethylsulphanyl)-2-amino-butyric acid (GW274150), 2-[2-(4-methoxy-pyridin-2-yl)-ethyl]-3H-imidazo[4,5-b]pyridine (BYK191023), 2-((R)-3-amino-1-phenyl-propoxy)-4-chloro-5-fluorobenzonitrile, 2-(((1R,3S)-3-amino-4-hydroxy-1-thiazol-5-yl-butylsulphanyl)-6-trifluoromethyl-nicotinonitrile, 2-((1R,3S)-3-amino-4-hydroxy-1-thiazol-5-yl-butylsulphanyl)-4-chloro-benzonitrile, 2-((1R,3S)-3-amino-4-hydroxy-1-thiazol-5-yl-butylsulphanyl)-5-chloro-benzonitrile, (2S,4R)-2-amino-4-(2-chloro-5-trifluoromethyl-phenylsulphanyl)-4-thiazol-5-yl-butan-1-ol, 2-((1R,3S)-3-amino-4-hydroxy-1-thiazol-5-yl-butylsulphanyl)-5-chloro-nicotinonitrile, 4-((S)-3-amino-4-hydroxy-1-phenyl-butylsulphanyl)-6-methoxy-nicotinonitrile, substituted 3-phenyl-3,4-dihydro-1-isoquinolinamine such as e.g. (1S,5S,6R)-7-chloro-5-methyl-2-aza-bicyclo[4.1.0]hept-2-en-3-ylamine (ONO-1714), (4R,5R)-5-ethyl-4-methyl-thiazolidin-2-ylideneamine, (4R,5R)-5-ethyl-4-methyl-selenazolidin-2-ylideneamine, 4-aminotetrahydrobiopterine, (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330), 3-(2,4-difluoro-phenyl)-6-[2-(4-imidazol-1-ylmethyl-phenoxy)-ethoxy]-2-phenyl-pyridine (PPA250), methyl 3-{[(benzo[1,3]dioxol-5-ylmethyl)-carbamoyl]-methyl}-4-(2-imidazol-1-yl-pyrimidin-4-yl)-piperazine-1-carboxylate (BBS-1), (R)-1-(2-imidazol-1-yl-6-methyl-pyrimidin-4-yl)-pyrrolidin-2-carboxylate (2-benzo[1,3]dioxol-5-yl-ethyl)-amide (BBS-2) and the pharmaceutical salts, prodrugs or solvates thereof.

As iNOS-inhibitors within the scope of the present invention it is also possible to use antisense oligonucleotides, particularly those antisense oligonucleotides that bind iNOS-coding nucleic acids. For example, WO 01/52902 describes antisense oligonucleotides, particularly antisense oligonucleotides that bind iNOS coding nucleic acids, for modulating the expression of iNOS.

MRP4-inhibitors used are preferably compounds selected from among N-acetyl-dinitrophenyl-cysteine, cGMP, cholates, diclofenac, dehydroepiandrosterone 3-glucuronide, dehydroepiandrosterone 3-sulphate, dilazep, dinitrophenyl-S-glutathione, estradiol 17-beta-glucuronide, estradiol 3,17-disulphate, estradiol 3-glucuronide, estradiol 3-sulphate, estrone 3-sulphate, flurbiprofen, folate, n5-formyl-tetrahydrofolate, glycocholate, glycolithocholic acid sulphate, ibuprofen, indomethacin, indoprofen, ketoprofen, lithocholic acid sulphate sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulphinepyrazone, taurochenodeoxycholate, taurocholate, taurodeoxycholate, taurolithocholate, topotecan, trequinsin, zaprinast and dipyridamole, optionally in the form of the racemates, enantiomers and diastereomers thereof and the pharmacologically acceptable acid addition salts and hydrates thereof.

The leukotriene biosynthesis inhibitors used such as for example those selected from among the 5-lipoxygenase (5-LO) inhibitors, cPLA2 inhibitors, leukotriene A4 hydrolase inhibitors or FLAP inhibitors, are preferably compounds selected from among zileuton, tipelukast, licofelone, darapladib, optionally in the form of the racemates, enantiomers and diastereomers thereof and the pharmacologically acceptable acid addition salts and hydrates thereof.

Non-steroidal anti-inflammatories (NSAIDs) that may be used are preferably compounds selected from among piroxicam, diclofenac, naproxen, flurbiprofen, fenoprofen, ketoprofen, ibuprofen, nimesulide, indomethacin, sulindac, azapropazone, phenylbutazone, aspirin; meloxicam, celecoxib, rofecoxib, valdecoxib, lumarocoxib, parecoxib, tenoxicam and etoricoxib, optionally in the form of the racemates, enantiomers and diastereomers thereof and optionally in the form of the pharmacologically acceptable acid addition salts, prodrugs, solvates or hydrates thereof.

CRTH2 antagonists used are preferably compounds selected from among ramatroban and laropiprant, optionally in the form of the racemates, enantiomers and diastereomers thereof and optionally in the form of the pharmacologically acceptable acid addition salts, prodrugs, solvates or hydrates thereof.

DP1-receptor modulators used are preferably compounds selected from among 7-[(1R,2R,3S,5S)-2-[[(5-hydroxybenzo[b]thien-3-yl)carbonyl]amino]-6,6-dimethylbicyclo[3.1.1]hept-3-yl], (5Z)-5-heptenoic acid (S-5751), laropiprant, and 2-[[4-[(1R,2S,3R,5R)-5-chloro-2-[(3S)-3-cyclohexyl-3-hydroxy-1-propyn-1-yl]-3-hydroxycyclopentyl]butyl]thio]-acetic acid (TS-002), optionally in the form of the racemates, enantiomers and diastereomers thereof and optionally in the form of the pharmacologically acceptable acid addition salts, prodrugs, solvates or hydrates thereof.

Thromboxane receptor antagonists used here are preferably compounds selected from among seratrodast, N-[[(1,1-dimethylethyl)amino]carbonyl]-2-[(4-methylphenyl)amino]-5-nitro-benzenesulphonamide (BM-573), (+/−)-sodium[2-(4-chlorophenylsulphonylaminomethyl)-indan-5-yl]acetate monohydrate (Z-335) and 2-[[[4-[[(4-chlorophenyl)sulphonyl]amino]butyl][[3-[[4-(1-methylethyl)-2-thiazolyl]methoxy]phenyl]methyl]amino]sulphonyl]-benzoic acid (KP-496), optionally in the form of the racemates, enantiomers and diastereomers thereof and optionally in the form of the pharmacologically acceptable acid addition salts, prodrugs, solvates or hydrates thereof.

Chemokine receptor antagonists that may be used are preferably compounds selected from among N-[5-chloro-2-[2-[(2R)-4-[(4-fluorophenyl)methyl]-2-methyl-1-piperazinyl]-2-oxoethoxy]phenyl]-urea hydrochloride (1:1) (BX-471), 2, N-[(1S,2S,4R)-4-(aminocarbonyl)-1-[(3-fluorophenyl)methyl]-2,7-dihydroxy-7-methyloctyl]-quinoxalinecarboxamide (CP-481715), (4,6-dimethyl-5-pyrimidinyl)[4-[(3S)-4-[(1R)-2-methoxy-1-[4-(trifluoromethyl)phenyl]ethyl]-3-methyl-1-piperazinyl]-4-methyl-1-piperidinyl]-methanone (Sch-417690), 2-hydroxy-N,N-dimethyl-3-[[2-[[(1R)-1-(5-methyl-2-furanyl)propyl]amino]-3,4-dioxo-1-cyclobuten-1-yl]amino]-benzamide (SCH-527123) and 1,4,8,11-tetraazacyclotetradecane, 1,1'-[1,4-phenylenebis(methylene)]bis, hydrochloride (1:8) (AMD-3100), optionally in the form of the racemates, enantiomers and diastereomers thereof and optionally in the form of the pharmacologically acceptable acid addition salts, prodrugs, solvates or hydrates thereof.

Neurokinin (NK1 or NK2) antagonists that may be used are preferably compounds selected from among: saredutant, nepadutant and figopitant, optionally in the form of the racemates, enantiomers and diastereomers thereof and optionally in the form of the pharmacologically acceptable acid addition salts, prodrugs, solvates or hydrates thereof.

Sphingosine1-phosphate receptor modulators that may be used are preferably compounds such as e.g. sonepcizumab, optionally in the form of the racemates, enantiomers and diastereomers thereof and optionally in the form of the pharmacologically acceptable acid addition salts, prodrugs, solvates or hydrates thereof.

Mucoregulators that may be used are preferably compounds selected from among: 3-[2-oxo-2-[2-[[3-(trifluoromethyl)phenyl]amino]-3-pyridinyl]ethyl]-1(3H)-isobenzofuranone (MSI-2216), erdosteine, fluorovent, talniflumate, fudosteine, optionally in the form of the racemates, enantiomers and diastereomers thereof and optionally in the form of the pharmacologically acceptable acid addition salts, prodrugs, solvates or hydrates thereof.

PPAR gamma agonists that may be used are preferably compounds selected from among: rosiglitazone, ciglitazone, pioglitazone and N-[2-[2-[(3-fluorophenyl)imino]-4-[4-(4-morpholinyl)phenyl]-3(2H)-thiazolyl]ethyl]-N'-methyl-urea (SMP-028), optionally in the form of the racemates, enantiomers and diastereomers thereof and optionally in the form of the pharmacologically acceptable acid addition salts, prodrugs, solvates or hydrates thereof.

Rho kinase inhibitors that may be used are preferably compounds such as e.g. Fasudil, optionally in the form of the racemates, enantiomers and diastereomers thereof and optionally in the form of the pharmacologically acceptable acid addition salts, prodrugs, solvates or hydrates thereof.

Adenosine receptor modulators that may be used are preferably compounds selected from among 4-(3,4-dichlorophenyl)-5-(4-pyridinyl)-2-thiazolamine (CGH-2466), 3-ethyl-3,9-dihydro-1-propyl-8-[1-[[3-(trifluoromethyl)phenyl]methyl]-1H-pyrazol-4-yl]-1H-purine-2,6-dione (CVT-6883), N-(4-cyanophenyl)-2-[4-(2.3.6.9-tetrahydro-2,6-dioxo-1,3-dipropyl-1H-purin-8-yl)phenoxy]-acetamide (MRS-1754), optionally in the form of the racemates, enantiomers and diastereomers thereof and optionally in the form of the pharmacologically acceptable acid addition salts, prodrugs, solvates or hydrates thereof.

Bradykinin receptor antagonists that may be used are preferably compounds selected from among icatibant and 1-piperazinepentanaminium, delta-amino-4-[[4-[[[2,4-dichloro-3-[[(2,4-dimethyl-8-quinolinyl)oxy]methyl]phenyl]sulphonyl]amino]tetrahydro-2H-pyran-4-yl]carbonyl]-N,N,N-trimethyl-ε-oxo, chloride, hydrochloride (1:1:1), (deltaS)-(MEN-16132), optionally in the form of the racemates, enantiomers and diastereomers thereof and optionally in the form of the pharmacologically acceptable acid addition salts, prodrugs, solvates or hydrates thereof.

Endothelin antagonists that may be used are preferably compounds selected from among actelion-1, ambrisentan, sitaxsentan, N-(2-acetyl-4.6-dimethylphenyl)-3-[[(4-chloro-3-methyl-5-isoxazolyl)amino]sulphonyl]-2-thiophenecarboxamide (TBC-3214) and bosentan, optionally in the form of the racemates, enantiomers and diastereomers thereof and optionally in the form of the pharmacologically acceptable acid addition salts, prodrugs, solvates or hydrates thereof.

Interleukin 1-beta converting enzyme (ICE) inhibitors that may be used are preferably compounds selected from among pralnacasan and N-(4-amino-3-chlorobenzoyl)-3-methyl-L-valyl-N-[(2R,3S)-2-ethoxytetrahydro-5-oxo-3-furanyl]-L-prolinamide (=VX-765), optionally in the form of the racemates, enantiomers and diastereomers thereof and optionally in the form of the pharmacologically acceptable acid addition salts, prodrugs, solvates or hydrates thereof.

Toll-like receptor (TLR) modulators that may be used are preferably compounds selected from among resiquimod, heplisav, resatorvid (TAK-242), optionally in the form of the racemates, enantiomers and diastereomers thereof and optionally in the form of the pharmacologically acceptable acid addition salts, prodrugs, solvates or hydrates thereof.

HMG-CoA Reductase inhibitors that may be used are preferably compounds selected from among lovastatin, simvastatin, pravastatin, fluvastatin and avorvastatin, optionally in the form of the racemates, enantiomers and diastereomers thereof and optionally in the form of the pharmacologically acceptable acid addition salts, prodrugs, solvates or hydrates thereof.

VLA-4 antagonists that may be used are preferably compounds selected from among natalizumab, valategrast, optionally in the form of the racemates, enantiomers and diastereomers thereof and optionally in the form of the pharmacologically acceptable acid addition salts, prodrugs, solvates or hydrates thereof.

SHIP agonists that may be used are preferably compounds selected from among 2,3,4,4a,5,6,6a,11,11a,11b-decahydro-4,4,6a,7,11b-pentamethyl, (4aS,6aR,11aR,11bS)-1 H-benzo[a]fluoren-9-ol (AQX-MN100) and MN-106, optionally in the form of the racemates, enantiomers and diastereomers thereof and optionally in the form of the pharmacologically acceptable acid addition salts, prodrugs, solvates or hydrates thereof.

Anti-TNF-antibodies which may be used here are preferably compounds selected from among infliximab, adalimumab, golimumab, cytoFab and etanercept.

Substances to counter swelling of the airways that may be used are preferably compounds selected from among phenylephrine, phenylpropanolamine, pseudophedrine, oxymetazoline, epinephrine, naphazoline, xylometazoline, propylhexedrine and Ilevodesoxyephedrine, optionally in the form of the racemates, enantiomers and diastereomers thereof and optionally in the form of the pharmacologically acceptable acid addition salts, prodrugs, solvates or hydrates thereof.

Antitussive substances that may be used are preferably compounds selected from among hydrocodone, caramiphen, carbetapentane and dextramethorphan, optionally in the form of the racemates, enantiomers and diastereomers thereof and optionally in the form of the pharmacologically acceptable acid addition salts, prodrugs, solvates or hydrates thereof.

Preferred lipoxin A4 derivatives which may be used here are preferably compounds selected from among
7,9,11,13-eicosatetraenoic acid, 5,6,15-trihydroxy, (5S,6R,7E,9E,11Z,13E,15R)-(15-epi-lipoxin a4),
7,9,11,13-eicosatetraenoic acid, 16-(4-fluorophenoxy)-5,6,15-trihydroxy, (5S,6R,7E,9E,11Z,13E,15S)-(ATL-1),
aspirin-triggered lipoxin A(4) and analogues,
protectin D1 (4,7,11,13,15,19-docosahexaenoic acid, 10,17-dihydroxy, (4Z,7Z,10R,11E,13E,15Z,17S,19Z)—,
resolvin E1 (6,8,10,14,16-eicosapentaenoic acid, 5,12,18-trihydroxy, (5S,6Z,8E,10E,12R,14Z,16E,18R)—) and
benzo-lipoxin A4 analogues,
optionally in the form of the racemates, enantiomers and diastereomers thereof and optionally in the form of the pharmacologically acceptable acid addition salts, prodrugs, solvates or hydrates thereof.

Preferred FPRL1-modulators which may be used here are preferably compounds such as e.g. methyl 5(S),6(R),7-trihydroxyl)eptanoate, optionally in the form of the racemates, enantiomers and diastereomers thereof and optionally in the form of the pharmacologically acceptable acid addition salts, prodrugs, solvates or hydrates thereof.

Preferred PI3 kinase antagonists which may be used here are preferably compounds selected from among
5-(quinoxalin-6-ylmethylene)thiazolidine-2,4-dione (AS-605240),
2-[(6-amino-9H-purin-9-yl)methyl]-5-methyl-3-(2-methylphenyl)-4(3H)-quinazolinone (C-87114),
2-methyl-2-[4-[3-methyl-2-oxo-8-(quinoline-3-yl)-2,3-dihydroimidazo[4,5-c]quinolin-1-yl]phenyl]propionitrile (BEZ-235),
optionally in the form of the racemates, enantiomers and diastereomers thereof and optionally in the form of the pharmacologically acceptable acid addition salts, prodrugs, solvates or hydrates thereof.

Preferred CCR5 antagonists which may be used here are preferably compounds selected from among maraviroc (4,4-difluoro-N-[(1S)-3-[(3-exo)-3-[3-methyl-5-(1-methylethyl)-4H-1,2,4-triazol-4-yl]-8-azabicyclo[3.2.1]oct-8-yl]-1-phenylpropyl]-cyclohexanecarboxamide), CCR5mAb004,
vicriviroc ((4.6-dimethyl-5-pyrimidinyl)[4-[(3S)-4-[(1R)-2-methoxy-1-[4-(trifluoromethyl)phenyl]ethyl]-3-methyl-1-piperazinyl]-4-methyl-1-piperidinyl]-methanone)
and
nifeviroc (N-[1-[[(3S.4R)-1-(cyclopentylcarbonyl)-4-hydroxy-4-phenyl-3-pyrrolidinylyl]methyl]-4-piperidinyl]-N-2-propen-1-yl-(4-nitrophenyl)methyl ester-carbaminic acid),
optionally in the form of the racemates, enantiomers and diastereomers thereof and optionally in the form of the pharmacologically acceptable acid addition salts, prodrugs, solvates or hydrates thereof.

Preferred CXCR1 or CXCR2 antagonists which may be used here are preferably compounds such as e.g. 3-[[3-[(dimethylamino)carbonyl]-2-hydroxyphenyl]amino]-4-[[(R)-1-(5-methylfuran-2-yl)propyl]amino]cyclobut-3-ene-1,2-dione (SCH-527123),
optionally in the form of the racemates, enantiomers and diastereomers thereof and optionally in the form of the pharmacologically acceptable acid addition salts, prodrugs, solvates or hydrates thereof.

Preferred substances, according to the invention, are the acid addition salts of the above mentioned MAP kinase inhibitors, iNOS inhibitors, MRP4 inhibitors, leukotriene biosynthese inhibitors, non-steroidal anti-inflammatory agents (NSAIDs), CRTH2 antagonists, DP1-receptor modulators, thromboxane receptor antagonists, chemokine receptor antagonists, neurokinin (NK1 or NK2) antagonists, sphingosine1-phosphate receptor modulators, mucoregulators, PPAR gamma agonists, Rho kinase inhibitors, adenosine receptor modulators, bradykinin receptor antagonists, endothelin antagonists, interleukin 1-beta converting enzyme (ICE) inhibitors, toll-like receptor (TLR) modulators, HMG-CoA reductase inhibitors, VLA-4 antagonists, SHIP agonists, anti-TNF-antibodies, substances to combat swelling of the airways, antitussive substances, lipoxin A4 derivatives, PI3 kinase antagonists, FPRL1-modulators, CCR5 antagonists, CXCR1 or CXCR2-antagonists also selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LIST OF REFERENCE NUMERALS 1 capsule cap
2 capsule body
3 corrugation (on capsule cap)
4 corrugation (on capsule cap)
5 bead (on capsule body)
6, 6a, 6b hole (on capsule cap)
7, 7a, 7b hole (on capsule body)
8 tongue (on capsule body)
9 groove (on capsule cap)
11 capsule in the first insertion position (holes covered)
12 capsule in the second insertion position (holes exposed)
13 capsule chamber
13a longitudinal wall (of the capsule chamber)
14 pusher
14a pushed in longitudinal wall (on the pusher)

14b projection (on the pusher)
15 screen
16 shaft
17 channel
18 guide rail
19 spring
20 air inlet opening
21 abutment edge
22 ring
22a bead (on the ring)
23 receptacle for ring
23a latching element (on receptacle for ring)
31 capsule (open at the top)
32 chamber
32a top (of the chamber)
32b fill chamber
33 inlet hole
34 arrow (indicates direction of filling)
35 screen
36 arrow (airflow towards the patient)
37 arrow (direction of vibration)
38 arrow (airflow)
39 cheek
40 powder
41 hole (axially at the bottom in the capsule, in capsule open at the top)
42 hole (laterally at the bottom in the hemispherical region, in capsule open at the top)
42a hole (laterally at the bottom of the closed capsule)
42b hole (laterally at the top of the closed capsule)
43 open end (in capsule open at the top)
44 lower end (in capsule open at the top)
45 hole (laterally at the bottom, in capsule open at the top)
46 hole (in capsule open at the top)
50 magazine
51 carrier
52 receptacle (in magazine)
52a step (in receptacle)
53 insert
53a step (on insert)
53b point (on insert)
55 seal
56 punch
57 punch ring
60 device
62 tube
63 flat component
64 pusher with inlet
65 vibration chamber
66 bar
67 mouthpiece
68 arrow (airflow at the inlet)
69 arrow (direction of suction)
70 device
71 capsule (closed)
71a,b hemispherical ends (of the closed capsule)
72, 72a, 72b prefabricated holes
73 tube
73a collar (on tube)
73b corrugation (on the outside of collar of the tube)
73d slot (on the tube)
73e gripping aid (on the tube)
73f spring arm (on the tube)
73g spacing (between tubes)
73k terminal region
73s recess (in wall of tube)
74 capsule chamber
75 bar
76 inlet
77 pusher
77a tapered portion (on the pusher)
77b spring arm (on the pusher)
78 mouthpiece
78b bead (on the lower inner edge of the mouthpiece)
78c gripping surface (on the mouthpiece)
78d mouth tube (in the mouthpiece)
78e centre wall (in the mouthpiece)
91 arrow (in the direction of flow of air at the inlet)
92 arrow (in the direction of breathing in)

The invention claimed is:

1. A capsule for use as a reservoir for a powdered pharmaceutical preparation in an inhaler, the capsule comprising:
a capsule body (2) having an open end; and a capsule cap (1) having an open end, where the capsule body (2) and capsule cap (1) are sized and shaped to fit into one another telescopically by way of the respective open ends so as to form a cavity, and to result in the capsule having an elongate length, a central tubular section, and opposing rounded ends, wherein at least one of the capsule body (2) and the capsule cap (1) comprise at least one prefabricated hole (7, 6); and
an annular component (22) in sliding engagement with, and sliding along at least a portion of, an exterior of at least one of the capsule body (2) and the capsule cap (1) such that, as the annular component (22) slides longitudinally along the elongate length of the at least one of the capsule body (2) and the capsule cap (1), in at least one longitudinal position the at least one hole is sealed off,
wherein each of the capsule cap (1) and the capsule body (2) comprise at least one prefabricated hole (6, 7), which are positioned such that that there is a telescopic insertion position of the capsule body (2) and capsule cap (1) in which the prefabricated holes (7, 6) are in registry with one another.

2. The capsule according to claim 1, wherein each of the capsule body (2) and the capsule cap (1) is of cup-shaped configuration comprising a capsule casing which forms a cylindrically or elliptically encircling wall.

3. The capsule according to claim 2, wherein the at least one prefabricated hole (7, 6) extends through the encircling wall.

4. The capsule according to claim 3, further comprising respective alignment elements disposed on the capsule casings of the capsule body (2) and capsule cap (1) on regions of the capsule casings that abut on one another such that the capsule body (2) and capsule cap (1) may be fitted into one another only in a defined alignment.

5. The capsule according to claim 1, wherein the prefabricated holes (7, 6) are positioned such that there is an alternative telescopic insertion position of the capsule body (2) and capsule cap (1) where the prefabricated holes (7, 6) are covered and thus the cavity in the capsule (11) is closed off.

6. The capsule according to claim 5, wherein the capsule body (2) and capsule cap (1) each comprise two prefabricated holes (7a, 7b, 6a, 6b) in upper and lower regions thereof such that in the telescopic insertion position the capsule (12) comprises a first pair of prefabricated holes in registration with one another at one end of the capsule and a second pair of prefabricated holes in registration with one another at an opposite end of the capsule.

7. The capsule according to claim 5, wherein each of the capsule body (2) and capsule cap (1) comprise latching elements operating to at least one of: (i) permit telescoping movement of the capsule body (2) and capsule cap (1) from an initial position through the alternative telescopic insertion position, but resists any telescoping movement once the telescopic insertion position has been reached; and (ii) prevent separation of the capsule body (2) and capsule cap (1) once the telescopic insertion position has been reached.

8. The capsule according to claim 1, wherein the capsule body (2) telescopes within the capsule cap (1), and the prefabricated hole of the capsule body (2) is at least one of: (i) larger than the prefabricated hole of the capsule cap (1); (ii) an oblong hole; and (iii) an elliptical hole.

9. The capsule according to claim 1, wherein at least one of:
at least one of the capsule body (2) and capsule cap (1) are made from a plastics material, polyethylene, polycarbonate, polyester, polypropylene or polyethylene terephthalate, and
the capsule body (2) and capsule cap (1) are formed in an injection moulding process such that the prefabricated holes (6, 7) are formed in the same injection moulding process.

10. An inhaler, comprising:
a capsule for a powdered pharmaceutical preparation, the capsule comprising: (i) a capsule body (2) having an open end; and (ii) a capsule cap (1) having an open end, where the capsule body (2) and capsule cap (1) are sized and shaped to fit into one another telescopically by way of the respective open ends so as to form a cavity, and to result in the capsule having an elongate length, a central tubular section, and opposing rounded ends, wherein at least one of the capsule body (2) and the capsule cap (1) comprise at least one prefabricated hole (7, 6); and
a capsule chamber (74) for receiving the capsule (71), wherein the capsule chamber (74) comprises an air inlet and an air outlet leading towards a mouthpiece (78); and
a pusher (77), which when actuated causes movement of an annular component (22) in sliding engagement with, and sliding along at least a portion of, an exterior of at least one of the capsule body (2) and the capsule cap (1), such that, as the pusher (77) causes the annular component (22) to slide longitudinally along the elongate length of the at least one of the capsule body (2) and the capsule cap (1), in the at least one longitudinal position the at least one prefabricated hole is sealed off and in at least one other longitudinal position the at least one prefabricated hole (6, 7, 72a, 72b) is exposed
wherein each of the capsule cap (1) and the capsule body (2) comprise at least one prefabricated hole (6, 7), which are positioned such that that there is a telescopic insertion position of the capsule body (2) and capsule cap (1) in which the prefabricated holes (7, 6) are in registry with one another.

11. The inhaler of claim 10, wherein:
the at least one prefabricated hole (6, 7) is positioned such that that there is a first telescopic insertion position of the capsule body (2) and capsule cap (1) where the prefabricated holes (7, 6) are covered and thus the cavity in the capsule (11) is closed off;
the prefabricated holes are positioned such that that there is a second telescopic insertion position of the capsule body (2) and capsule cap (1) in which the prefabricated holes (7, 6) are in registry with one another; and
the pusher (14) operates such that the capsule cap (1) moves relative to the capsule body (2) such that the second telescopic insertion position is reached.

12. The inhaler of claim 10, wherein the pusher (77) operates such that the annular component can be moved on, or separated from, the capsule (71), so that at least one prefabricated hole (6, 7, 72a, 72b) is exposed.

13. The inhaler of claim 12, wherein after actuation of the pusher (77) the annular component forms a seal between the pusher (77) and the capsule chamber (74).

14. The inhaler of claim 10, wherein the pusher (14) cooperates with a spring (19) such that after actuation the pusher (14) returns to an original position.

15. The inhaler of claim 10, wherein the pusher (77) comprises at least one latching element, including at least one spring arm (77b), which latches with another component of the inhaler when the pusher (77) is fully actuated such that the pusher (77) cannot be non-destructively pushed back into an original position.

16. An inhaler, comprising:
a capsule for a powdered pharmaceutical preparation, the capsule comprising: (i) a capsule body (2) having an open end; and (ii) a capsule cap (1) having an open end, where the capsule body (2) and capsule cap (1) are sized and shaped to fit into one another telescopically by way of the respective open ends so as to form a cavity, and to result in the capsule having an elongate length, a central tubular section, and opposing rounded ends, wherein at least one of the capsule body (2) and the capsule cap (1) comprise at least one prefabricated hole (7, 6);
a capsule receptacle (73) for storing the capsule before use, the capsule receptacle being in sliding engagement with an exterior of at least one of the capsule body (2) and the capsule cap (1) such that the at least one prefabricated hole (7,6) is sealed when the capsule is disposed therein;
a capsule chamber (74) in axial alignment with the capsule receptacle (73) and receiving the capsule (71) from the capsule receptacle (73) as the capsule (71) slides longitudinally through the capsule receptacle (73) into the capsule chamber (74); and
a pusher (77) that moves the capsule (71) out of the capsule receptacle and into the capsule chamber (74), such that as the exterior of at least one of the capsule body (2) and the capsule cap (1) slides longitudinally along and out of the capsule receptacle (73), the at least one prefabricated hole (7,6) is unsealed.

17. The inhaler of claim 16, wherein after the capsule (71) has been moved into the capsule chamber (74) the pusher (77) at least one of: (i) forms a wall region of the capsule chamber (74); and (ii) forms an air inlet for the capsule chamber (74) is formed in the pusher (77).

18. The inhaler of claim 16, wherein the pusher (77) comprises at least one latching element, including at least one spring arm (77b), which latches with another component of the inhaler when the pusher (77) is fully actuated such that the pusher (77) cannot be non-destructively pushed back into an original position.

19. An inhaler, comprising:
a capsule for a powdered pharmaceutical preparation, the capsule comprising: (i) a capsule body (2) having an open end; and (ii) a capsule cap (1) having an open end, where the capsule body (2) and capsule cap (1) are sized and shaped to fit into one another telescopically by way of the respective open ends so as to form a cavity, and to result in the capsule having an elongate length, a central tubular section, and opposing rounded ends, wherein at least one of the capsule body (2) and the capsule cap (1) comprise at least one prefabricated hole (72a, 72b); and a capsule receptacle (73) for storing the capsule before use, the capsule receptacle being in sliding engagement with an exterior of at least one of the capsule body (2) and the capsule cap (1) such that the at least one prefabricated hole (7,6) is sealed when the capsule is disposed therein; and a capsule chamber (74) in which the capsule receptacle is at least partly arranged in a coaxial and sliding relationship, such that when the capsule receptacle (73) is removed by sliding out from the capsule chamber (74) the exterior of at least one of the capsule body (2) and the capsule cap (1) slides longitudinally along and out of the capsule receptacle (73), the at least one prefabricated hole (7,6) is unsealed, and the capsule (71) remains in the capsule chamber (74).

20. The inhaler of claim 19, further comprising a mouthpiece (78) with a mouth tube (78d) that connects the capsule chamber (74) to an air outlet, the air outlet being an opening located in a centre of an end of the mouthpiece (78) that is next to a user's mouth during use, wherein a component that forms the capsule receptacle extends through the mouth tube (78d).

21. The inhaler of claim 19, further comprising at least one of a tongue, pin or bar (75) that delimits the capsule chamber (13, 74) and extends through a component that forms the capsule receptacle, wherein the component comprises a recess through which the tongue, pin or bar (75) slides during relative movement between the component and the capsule chamber (13, 74).

22. The inhaler of claim 19, further comprising a mouthpiece (78) having one end that is closest to a user's mouth during use forming an opening that is connected to the capsule chamber (13, 74) in a middle of the one end, wherein a component that forms the capsule receptacle is embodied as a cap which, in a transporting state of the inhaler, closes off the opening at the one end such that areas to which the user places his lips when using the inhaler are covered.

23. The inhaler of claim 19, wherein a component that forms the capsule receptacle comprises elements including spring arms, which prevent the capsule receptacle from being non-destructively reinserted in the capsule chamber (13, 74) after being fully removed from the capsule chamber (13, 74).

24. The inhaler of claim 19, wherein:

the capsule includes a flexible film surrounding the capsule such that in a transporting state of the inhaler the film closes off the at least one prefabricated hole (72, 72a, 72b), where at least one of: (i) part of the film protrudes beyond the capsule (11, 74) at one end of the capsule (11, 74), and (ii) the film is connected to a pull strip; and an the inhaler further comprises an opening such that the film can be pulled out of the inhaler by at least one of the protruding part and the pull strip through the opening, whereupon the at least one prefabricated hole (72, 72a, 72b) is exposed.

25. A process for manufacturing an inhaler according to claim 19, characterised in that the capsule body (2) which is open at one end is inserted in an annular component and/or the capsule receptacle, the capsule body (2) is filled with a measured amount of powdered pharmaceutical preparation, the capsule body is then closed off with a capsule cap (1) and the annular component and/ or the capsule receptacle is assembled with the other components of the inhaler.

26. The process for manufacturing an inhaler according to claim 25, characterised in that after the assembly of the components of the inhaler the system is in a state for transporting or storage, in which the holes of the capsule (71) formed by the capsule body (2) and capsule cap (1) are closed off, and by pushing or pulling a component of the inhaler or system the system is converted into a state ready for use, the holes of the capsule being exposed by this pushing or pulling and/or the capsule (71) being moved into a capsule chamber (74).

27. The inhaler of claim 19, further comprising:

a further capsule (11, 71) for another powdered pharmaceutical preparation, the further capsule comprising: (i) a capsule body (2) having an open end; and (ii) a capsule cap (1) having an open end, which can be fitted into one another telescopically by way of the respective open ends so as to form a cavity, wherein at least one of the capsule body (2) and the capsule cap (1) comprise at least one prefabricated hole (7, 6);

a further capsule chamber (13, 74) for receiving the further capsule (11, 71), wherein the further capsule chamber (13, 74) comprises an air inlet and an air outlet leading towards the mouthpiece (78).

28. The inhaler of claim 27, wherein the powdered pharmaceutical preparation and the other powdered pharmaceutical preparation are at least one of: (i) different formulations, and (ii) different amounts of formulation.

* * * * *